United States Patent
Yu et al.

(10) Patent No.: US 10,364,471 B2
(45) Date of Patent: Jul. 30, 2019

(54) TUMOR SUPPRESSOR REC8 AS A BIOMARKER FOR GASTRIC CANCER

(71) Applicant: The Chinese University of Hong Kong, Hong Kong (CN)

(72) Inventors: Jun Yu, Hong Kong (CN); Joseph Jao Yiu Sung, Hong Kong (CN); Qiaoyi Liang, Hong Kong (CN)

(73) Assignee: The Chinese University of Hong Kong, Shatin, N.T. (HK)

(*) Notice: Subject to any disclaimer, the term of this patent is extended or adjusted under 35 U.S.C. 154(b) by 58 days.

(21) Appl. No.: 15/600,366

(22) Filed: May 19, 2017

(65) Prior Publication Data
US 2018/0334720 A1 Nov. 22, 2018

(51) Int. Cl.
 C12Q 1/6886 (2018.01)
 G01N 33/574 (2006.01)
 A61K 38/17 (2006.01)
 G01N 33/68 (2006.01)

(52) U.S. Cl.
 CPC ........ *C12Q 1/6886* (2013.01); *A61K 38/1709* (2013.01); *G01N 33/57446* (2013.01); *G01N 33/6875* (2013.01); *C12Q 2600/118* (2013.01); *C12Q 2600/154* (2013.01); *C12Q 2600/158* (2013.01); *G01N 2333/4704* (2013.01); *G01N 2800/50* (2013.01)

(58) Field of Classification Search
None
See application file for complete search history.

(56) References Cited

PUBLICATIONS

Furuta et al. Cancer Res. 2006. 66(12):6080-6086. (Year: 2006).*
Liu et al. Oncotarget. 2015. 6(36):39211-39224. (Year: 2015).*
Yu et al. Oncogene. 2017. 36:182-193. (Year: 2017).*
Zhao et al. Cancer. 2013. 119(2):304-312. (Year: 2013).*

* cited by examiner

*Primary Examiner* — Joseph G. Dauner
(74) *Attorney, Agent, or Firm* — Kilpatrick Townsend & Stockton LLP

(57) ABSTRACT

The present invention provides a method for diagnosing and determining prognosis of gastric cancer in a subject by detecting suppressed expression of the REC8 gene, which in some cases is due to elevated methylation level in the genomic sequence of this gene. A kit and device useful for such a method are also provided. In addition, the present invention provides a method for treating gastric cancer by increasing REC8 gene expression or activity. Lastly, a highly sensitive and accurate detection method is provided for rapid determination of REC8 gene methylation status.

10 Claims, 26 Drawing Sheets
(25 of 26 Drawing Sheet(s) Filed in Color)
Specification includes a Sequence Listing.

FIG. 8A

Strategy of primer-probe design

Electrophoresis

*Duplex-qPCR*

*Sanger sequencing*

TUMOR SUPPRESSOR REC8 AS A BIOMARKER FOR GASTRIC CANCER

REFERENCE TO SUBMISSION OF A SEQUENCE LISTING AS A TEXT FILE

The Sequence Listing written in file 080015-022300US-1048893_SequenceListing.txt created on Aug. 3, 2017, 23,970 bytes, machine format IBM-PC, MS-Windows operating system, is hereby incorporated by reference in its entirety for all purposes.

BACKGROUND OF THE INVENTION

Gastric cancer, also known as stomach cancer, is the fourth most common cancer worldwide with approximately 1,000,000 cases diagnosed annually. It is a disease with a high mortality rate (about 800,000 deaths per year), making it the second most common cause of cancer death worldwide after lung cancer. The incidence of gastric cancer is significantly higher among men and in developing nations, including many Asian countries.

Gastric cancer often remains asymptomatic or exhibits only nonspecific symptoms in its early stages, diagnosis in many cases is therefore not made until the disease has reached an advanced stage. This leads to a generally poor prognosis: metastasis occurs in 80-90% of individuals diagnosed with gastric cancer, with a six-month survival rate of 65% in those diagnosed in early stages and less than 15% of those diagnosed in late stages.

Because of the prevalence of gastric cancer and its grave implications on patients' life expectancy, there exists an urgent need for new and more effective methods to diagnose, monitor, and treat gastric cancer. This invention fulfills this and other related needs.

BRIEF SUMMARY OF THE INVENTION

The present inventors discovered REC8 to be preferentially methylated in gastric cancer using promoter methylation array in an effort to elucidate the epigenetic alteration and biological function of REC8 in gastric cancer. REC8 was down-regulated in 100% (3/3) of EBV-positive and 80% (8/10) of EBV-negative gastric cancer cell lines by promoter methylation, but expression could be restored through demethylation treatment. Protein expression of REC8 was significantly lower in human primary gastric tumors than in adjacent non-tumor tissues. A negative correlation between methylation and mRNA expression of REC8 was observed in 223 gastric samples of The Cancer Genome Atlas study (r=−0.7018, P<0.001). The methylation level (%) of REC8 promoter was significantly higher in EBV-positive than EBV-negative gastric tumors, as shown by bisulfite genomic sequencing (77.6 [69.3-80.5] vs. 51.4 [39.5-62.3], median [interquartile range]; P<0.001); methylation levels in both subtypes of tumors were significantly higher than in normal stomach tissues (14.8 [4.2-24.0]) (both P<0.001). Multivariate analysis revealed that REC8 methylation was an independent factor for poor survival in gastric cancer patients (HR=1.68, P<0.05). REC8 expression significantly suppressed cell viability, clonogenicity and cell cycle progression; it induced apoptosis and inhibited migration of AGS-3V (EBV-positive) and BGC823 (EBV-negative) gastric cancer cells, and it suppressed tumorigenicity in nude mice. In contrast, knock-down of REC8 in gastric epithelial immortalized GES-1 cells significantly increased cell viability, clonogenicity and migration ability. The tumor suppressive effect of REC8 is mediated at least in part by down-regulation of genes involved in cell growth (G6PD, SLC2A1, NOL3, MCM2, SNAI1 and SNAI2), and up-regulation of apoptosis/migration inhibitors (GADD45G and LDHA) and tumor suppressors (PinX1, IGFBP3 and ETS2). In conclusion, REC8 is a novel tumor suppressor that is commonly down-regulated by promoter methylation in gastric cancer, especially in the EBV-associated subtype. Promoter methylation of REC8 is an independent risk factor for shortened survival of gastric cancer patients.

Accordingly, the present inventors have identified REC8 as a novel tumor suppressor and diagnostic/prognostic marker for human gastric cancer. More specifically, the inventors show that, compared with normal individuals, CpG islands of the REC8 gene (especially in the promoter region) are hypermethylated in biological samples of cancer tissues from gastric cancer patients. Such hypermethylation leads to REC8 silencing at both mRNA and protein levels. Restoration of REC8 expression inhibits cancer cell growth and induces programmed cell death. Protein/mRNA expression level of REC8 and promoter methylation level of REC8 genetic sequence closely correlate with the survival of gastric cancer patients and are therefore also useful as prognostic markers for gastric cancer.

As such, in the first aspect, the present invention provides a method for assessing the risk for gastric cancer in a subject, i.e., the likelihood of gastric cancer being present in the subject and/or the likelihood of the subject developing the disease at a later time. The method includes the steps of: (a) measuring expression level of REC8 in a sample taken from the subject, and (b) comparing the expression level obtained in step (a) with a standard control. When a decrease in the expression level of REC8 is detected as compared with the standard control, it indicates that the subject may have gastric cancer or have an increased risk for gastric cancer. Typically, the sample used in the method is a stomach mucosa sample, e.g., one that includes stomach epithelial cells. The subject being tested may be a human or a member of other mammals such as primates, who may or may not exhibit any signs indicative of any condition or abnormality relating to the stomach.

In some embodiments, the expression level of REC8 is the REC8 protein level. In other embodiments, the expression level of REC8 is REC8 mRNA level. When the REC8 protein level is measured, step (a) may include an immunoassay using an antibody that specifically binds the REC8 protein. For example, a Western Blot analysis may be used. In other cases, step (a) may involve mass spectrometry, or a hybridization-based assay such as hybridization to a microarray, fluorescence probe, or molecular beacon.

When REC8 mRNA level is measured, step (a) in some cases may involve an amplification reaction, such as a polymerase chain reaction (PCR), especially a reverse transcriptase-PCR (RT-PCR). In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:1, 2, or 5 or a complement thereof. In some cases, the polynucleotide probe may include a detectable moiety.

In some embodiments, when the subject is indicated as having gastric cancer or having an increased risk of gastric cancer after the first round of method steps described above, the claimed method may further include repeating the same steps at a later time using the same type of sample from the subject. An increase in the expression level of REC8 at the later time as compared to the amount from the original step (a) indicates an improvement of gastric cancer or a lessened risk for the disease, whereas a decrease indicates a worsening of gastric cancer or a heightened risk for the disease.

In a second aspect, the present invention provides another method for detecting gastric cancer or assessing risk of gastric cancer in a subject. The method includes the steps of: (a) treating a sample taken from the subject with an agent that differentially modifies methylated and unmethylated DNA; and (b) determining whether each CpG in a CpG-containing genomic sequence is methylated or unmethylated, thus determining the number of methylated CpGs within this sequence, with the CpG-containing genomic sequence being at least a segment of SEQ ID NO:5 and comprising at least 1, 2, 3, 4, 5, 10, 15, or 19 CpG pairs. When the presence of at least one, or at least 5, or at least 10 methylated CpGs (for example, at least 50% of total CpGs), is detected in the CpG-containing genomic sequence, it indicates that the subject may have gastric cancer or is at an increased risk of developing the disease. In some cases, the number of methylated CpGs is compared with a control number, e.g., the number of methylated CpGs in the same genomic sequence determined following the same process described above using a sample of the same type from non-cancerous tissue originated from a healthy control subject who has been determined as having no gastric cancer or no known risk for the disease. When the number of methylated CpGs is higher in the test subject compared to the control number, the test subject is determined as having gastric cancer or having an increased risk for the disease; otherwise the test subject is determined as not having gastric cancer or not having any elevated risk for developing the disease.

In some embodiments, the CpG-containing genomic sequence contains two or more CpGs (e.g., up to 5, 10, 12, 15, or 19 CpGs), and when at least 50% of all CpGs being highly methylated (for example, at least 10 of 19 CpGs in SEQ ID NO:5 being highly methylated or nearly 100% methylated) or when at least 90% of all CpGs being at least 50% methylated (for example, at least 17 of 19 CpGs in SEQ ID NO:5 being moderately methylated or 50-100% methylated), the subject is indicated as having or at an increased risk for gastric cancer. In some cases, the CpG-containing genomic sequence is a segment of at least 15, 20, 50, 100, 125, 150, 200, 230 or more contiguous nucleotides of SEQ ID NO:5. In other cases, the CpG-containing genomic sequence is SEQ ID NO:5. In one embodiment of the claimed method, the CpG-containing genomic sequence is SEQ ID NO:4, and when at least 5, 6, 7, 8, 9, 10, 11, 12, 13, 14, 15, 16, 17, 18, or 19 of all CpGs in this CpG-containing genomic sequence are methylated (at least 50% and up to 100% methylated), the subject is indicated as having gastric cancer or having an increased risk for gastric cancer.

In some examples, the sample used in the claimed method is a stomach mucosa sample. In other examples, when the subject is indicated as having gastric cancer after the first round of method steps described above, the method further involves repeating steps (a) and (b) at a later time using the sample type of sample from the subject. When an increase is detected in the number of methylated CpGs at the later time as compared to the number of methylated CpGs determined from the original step (b), it indicates a worsening of gastric cancer, whereas a decrease indicates an improvement of gastric cancer.

In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite (e.g., sodium bisulfite). In other embodiments, step (b) of the method involves an amplification reaction; or step (b) may involve sequencing of a DNA molecule.

In a third aspect, the present invention provides a method for assessing likelihood of mortality in a gastric cancer patient. The method includes the steps of: (a) treating a sample taken from a gastric cancer patient, who has received a diagnosis of gastric cancer, with an agent that differentially modifies methylated and unmethylated DNA; and (b) determining whether each CpG in a CpG-containing genomic sequence is methylated or unmethylated, thus determining the number of methylated CpGs within this sequence, with the CpG-containing genomic sequence being at least a segment of SEQ ID NO:5 and comprising at least 1, 2, 3, 4, 5, 10, 11, 12, 13, 14, 15, 16, 17, 18, or 19 CpG pairs. When the presence of at least 1 or 2, 3 or 4, or at least 5, 7, 8, 9, or 10 methylated CpGs (for example, at least 50% of total CpGs), is detected in the CpG-containing genomic sequence, it indicates that the subject has a high likelihood of mortality (e.g., more likely than not, or greater than 10%, 20%, 30%, 40%, 50%, 60%, 70%, 80%, or 90% chance of mortality) in a subsequent time period, e.g., 1, 2, 3, 4, or 5 years or up to 10 years. In some cases, the likelihood of mortality is compared between two subjects who both have received a diagnosis of gastric cancer. The number of methylated CpGs determined from the first patient's sample after steps (a) and (b) is then compared with the number of methylated CpGs in the same genomic sequence determined following the same process using a sample of the same type originated from the second patient. When the number of methylated CpGs is higher in the first patient's sample compared to the number in the second patient's sample, the first patient is determined as having a higher likelihood of mortality due to gastric cancer than the second patient in a subsequent time period, e.g., 1, 2, 3, 4, or 5 years or up to 10 years. In some cases, the comparison is made between one test patient and an established low mortality patient who has been previously determined to have no or a very low number (e.g., 1 or 2) or a very low percentage (e.g., 5% or 10% or less) of methylated CpGs among all CpGs in the genomic sequence. When the test subject is found to have more methylated CpGs (especially when comparing the number of CpGs in comparable methylation level, for example, 50-100% methylation level or 100% methylation level) than the low mortality patient in the same genomic region, after both patients' samples have been processed through the method steps describe above, the test patient is deemed to have a higher likelihood of mortality due to gastric cancer than the low mortality patient for a subsequent time period of, e.g., 1, 2, 3, 4, or 5 years or up to 10 years.

In some embodiments, the CpG-containing genomic sequence analyzed in this method contains two or more CpGs, for example, 3, 4, 5, 6, 7, 8, 9, 10, 11, 12, 13, 14, 15, 16, 17, 18, or 19 CpGs. In some cases, the CpG-containing genomic sequence is a segment of at least 15, 20, 50, 100, 125, 150, 200, 230, or more contiguous nucleotides of SEQ ID NO:5. In other cases, the CpG-containing genomic sequence is SEQ ID NO:5.

In some examples, the sample used in the claimed method is a stomach mucosa sample. In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite (e.g., sodium bisulfite). In other embodiments, step (b) of the method involves an amplification reaction such as a PCR; or step (b) may involve sequencing of a DNA molecule. In some embodiments, the PCR is performed using at least one primer consisting of the sequence set forth in any one of SEQ ID NOs:9, 10, 11, and 12, in combination with one or more other primer(s) appropriate for the amplification reaction.

In a related application of this invention, likelihood of mortality in a gastric cancer patient due to the disease can also be assessed by comparing the expression level of REC8 mRNA or protein among patients who have been diagnosed with gastric cancer. Briefly, the method for assessing likelihood of mortality includes the steps of: (a) measuring expression level of REC8 in a sample taken from a first patient who has been diagnosed with gastric cancer, and (b) comparing the expression level obtained in step (a) with the expression level of REC8 determined in a sample of same type that was taken from a second gastric cancer patient and measured in the same step (a). When the expression level of REC8 is lower in the first patient's sample than that found in the second patient's sample, the first patient is deemed as having a higher likelihood of mortality from gastric cancer than the second patient. Typically, the sample used in the method is a stomach mucosa sample, e.g., one that includes stomach epithelial cells.

The subject being tested may be a human or a member of other mammals such as primates. In some cases, the second patient is one who has been diagnosed with gastric cancer but has been previously determined as having a normal expression level of REC8 mRNA and/or protein in the stomach cancer tissue.

In some embodiments of this method, the expression level of REC8 is the REC8 protein level. In other embodiments, the expression level of REC8 is REC8 mRNA level. When the REC8 protein level is measured, step (a) may include an immunoassay using an antibody that specifically binds the REC8 protein. For example, a Western Blot analysis may be used. In other cases, step (a) may involve mass spectrometry, or a hybridization-based assay such as hybridization to a microarray, fluorescence probe, or molecular beacon.

When REC8 mRNA level is measured, step (a) in some cases may involve an amplification reaction, such as a PCR, especially an RT-PCR. In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:1, 2, or 5, or a complement thereof. In some cases, the polynucleotide probe may include a detectable moiety. The sample used in this method is a stomach mucosa sample taken from confirmed cancerous tissues.

In a fourth aspect, the present invention provides a kit for detecting gastric cancer in a subject, comprising (1) a standard control that provides an average amount of REC8 protein or REC8 mRNA; and (2) an agent that specifically and quantitatively identifies REC8 protein or REC8 mRNA. In some cases, the agent may be an antibody that specifically binds the REC8 protein; or the agent may be a polynucleotide probe that hybridizes with the REC8 mRNA. For example, the polynucleotide probe hybridizes with at least a segment of SEQ ID NO:1, 2, or 5, or a complement thereof. The agent may include a detectable moiety. In other cases, the kit may further comprise two oligonucleotide primers for specifically amplifying at least a segment of SEQ ID NO:1, 2, or 5, or its complement in an amplification reaction. Typically, the kit will further include an instruction manual.

In a fifth aspect, the present invention provides a method for inhibiting growth of a stomach cancer cell. The claimed method includes the step of contacting the stomach cancer cell with (1) an effective amount of a polypeptide that comprises the amino acid sequence set forth in SEQ ID NO:4 or (2) a nucleic acid that comprises a polynucleotide sequence encoding SEQ ID NO:4. In some embodiments, the nucleic acid is an expression cassette comprising a promoter operably linked to the polynucleotide sequence encoding SEQ ID NO:4. Various promoters may be useful in this method, for example, the promoter may be an epithelium-specific promoter. In other embodiments, the nucleic acid comprises the polynucleotide sequence set forth in SEQ ID NO:1 or 2. In yet other embodiments, the stomach cancer cell is within a patient's body.

In addition, the present invention provides a kit for detecting gastric cancer. The kit comprises: (1) an agent that differentially modifies methylated and unmethylated DNA, and (2) an indicator that, after the agent has been used to treat a sample from a subject who is being tested for gastric cancer, determines whether each CpG in a CpG-containing genomic sequence is methylated or unmethylated. The CpG-containing genomic sequence is at least a segment of SEQ ID NO:5 and comprises at least 1, 2, 3, 4, 5, 6, 7, 8, 9, 10, 11, 12, 13, 14, 15, 16, 17, 18, or 19 CpG pairs. The present invention also provides a composition for inhibiting growth of a gastric cancer cell. The composition contains an effective amount of (1) a polypeptide comprising the amino acid sequence set forth in SEQ ID NO:4 (e.g., a polypeptide consisting of the amino acid sequence of SEQ ID NO:4) or (2) a nucleic acid comprising or consisting of a polynucleotide sequence encoding SEQ ID NO:4 (e.g., a nucleic acid sequence comprising the polynucleotide sequence of SEQ ID NO:1 or 2), and a pharmaceutically acceptable carrier. In this regard, this invention further provides the use of a polypeptide comprising the amino acid sequence set forth in SEQ ID NO:4 (e.g., a polypeptide consisting of the amino acid sequence of SEQ ID NO:4) or a nucleic acid comprising a polynucleotide sequence encoding SEQ ID NO:4 (e.g., a nucleic acid sequence comprising or consisting of the polynucleotide sequence of SEQ ID NO:1 or 2) in preparing a medicament for inhibiting growth of a gastric cancer cell.

In a sixth aspect, the present invention provides a sensitive and non-invasive method for detecting REC8 gene methylation status, which may serve as the first step in rapid assessment of risk of various types of cancer, including gastric cancer, liver cancer, and colon cancer, and early detection of these potentially deadly diseases. The method includes these steps: (1) treating genomic DNA obtained from a sample taken from a subject with a bisulfite; (2) performing an amplification reaction, such as a PCR especially quantitative PCR (qPCR), to amplify the treated genomic DNA from step (1) using a primer comprising the nucleotide sequence of SEQ ID NO:11 or 12; (3) analyzing the amplicon, or the product of amplification reaction from step (2), to determine the methylation status of REC8 gene. In some embodiments, the primer pair used in a PCR (especially qPCR) of this method includes a first oligonucleotide primer comprising or consisting of the nucleotide sequence set forth in SEQ ID NO:11 and a second oligonucleotide primer comprising or consisting of the nucleotide sequence set forth in SEQ ID NO:12.

In some embodiments, the sample is a blood sample, such as a plasma or serum sample, or a fraction of whole blood sample including some or all blood cells. In some embodiments, the sample may be a tissue sample (such as biopsy taken from a test subject's stomach, colon or liver), a stool sample, or a urine sample.

In some embodiments, the subject whose sample is being analyzed in this method is a human individual suspected of either having cancer (especially gastric, liver, or colon cancer) or at risk of later developing cancer (e.g., due to strong family history). Although corresponding tissue samples are often analyzed (e.g., liver biopsy is used for testing for liver cancer risk or presence), blood samples such as plasma or serum are also useful for this method due to its exceptionally high level of sensitivity and specificity.

In some embodiments, the analysis in step (3) may include sequencing of the amplicon from step (2) to determine the primary polynucleotide sequence, thus determine which CpGs were methylated and which CpGs were unmethylated. In some embodiments, a probe is used in step (3), which is designed to specifically hybridize with only the methylated version of amplicon (a methylation probe), for example, one comprising or consisting of the sequence set forth in SEQ ID NO:13. In some embodiments, a probe is used in step (3), which is designed to specifically hybridize with only the unmethylated version of amplicon (a non-methylation probe), for example, one comprising or consisting of the sequence set forth in SEQ ID NO:14. While each of these probes is typically labeled with a detectable moiety for ready detection and identification, the methylation probe and non-methylation probe are often labeled with two distinct labels such that they can be used in the same reaction mix to detect two different versions (methylated and unmethylated) amplicon potentially present in the same reaction mix. Exemplary labels are described in the Examples.

In a related aspect of this detection method, a kit is provided for rapid and reliable determination of REC8 gene methylation status. The kit comprises (1) an oligonucleotide primer comprising the nucleotide sequence of SEQ ID NO:11; and (2) an oligonucleotide primer comprising the nucleotide sequence of SEQ ID NO:12. The two primers may be kept in the same container, or they may be kept in two separate containers. In some cases, the sequences for the first and second primers consist of SEQ ID NO:11 and SEQ ID NO:12, respectively. Optionally, reagents necessary for carrying out an amplification reaction (e.g., PCR) may be included in the kit, such as a DNA polymerase, deoxynucleotide triphosphates or dNTPs, and amplification reaction buffer(s). Also, a composition comprising a bisulfite may be included in the kit. In some embodiments, the kit further comprises a methylation probe to specifically detect the presence of a methylated version of the REC8 genomic sequence, after bisulfite treatment and amplification reaction (such as PCR). An exemplary methylation probe comprises or consists of the nucleotide sequence set forth in SEQ ID NO:13. In some embodiments, the kit further comprises a non-methylation probe to specifically detect the presence of an unmethylated version of the REC8 genomic sequence, after bisulfite conversion and amplification reaction (such as PCR). An exemplary non-methylation probe comprises or consists of the nucleotide sequence set forth in SEQ ID NO:14. In one particular embodiment, the kit includes four separate containers containing the primer of SEQ ID NO:11, the primer of SEQ ID NO:12, the probe of SEQ ID NO:13, and the probe of SEQ ID NO:14. Optionally, the kit includes an instruction manual to guide the user in the proper use of the reagents for detecting REC8 gene methylation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) REC8 expression was determined by RT-PCR. REC8 (normalized to β-actin) was silenced in 9 of 13 detected GC cell lines. (FIG. 1B) Bisulfite genomic sequencing (BGS) analysis confirmed the methylation status of REC8 in gastric cancer cell lines. (FIG. 1C) The mRNA expression of REC8 was restored after treatment with demethylation agent, 5-Aza.

(FIG. 2A) REC8 protein expression was observed in non-tumor normal tissues, but not detected in gastric tumor tissues of Chinese patients by immunohistochemistry. (FIG. 2B) A negative correlation between promoter methylation and mRNA levels of REC8 in the TCGA cohort of 223 gastric samples. R, correlation coefficient. (FIG. 2C and FIG. 2D) Promoter methylation level of REC8 was determined in primary EBV-positive and EBV-negative gastric cancers and normal stomach tissues of Chinese patients by bisulfite genomic sequencing. (FIG. 2E) Receiver operating characteristics (ROC) curve analysis showed that methylation level of REC8 could discriminate between gastric cancer and normal mucosa, as well as EBV-positive and EBV-negative gastric tumors.

(FIG. 3A) The distribution of the methylation levels in all 191 gastric cancer samples of Chinese patients. High methylation level of REC8 (>55'%©) significantly correlates with shortened survival in Chinese gastric cancer patients. (FIG. 3B) The distribution of the methylation levels in 178 EBV-negative gastric cancers. High methylation level of REC8 (>55%) significantly correlates with shortened survival in EBV-negative gastric cancer patients.

(FIG. 4A) Ectopic expression of REC8 in AGS-EBV and BGC823 cell lines was confirmed by western blot. (FIG. 4B) Overexpression of REC8 significantly reduced cell viability in gastric cancer cells. (FIG. 4C) Overexpression of REC8 significantly suppressed colony formation. (FIG. 4D) REC8 significantly attenuated tumorigenicity of BGC823 cells in nude mice.

(FIG. 5A) Representative result of scratch healing and invasion assays. (FIG. 5B) Expression of REC8 increased G1 phase cell population but decreased S phase cell population, as shown by flow cytometry analysis. (FIG. 5C) REC8 induced apoptosis in gastric cancer cells, as determined by flow cytometry analysis following Annexin V and 7-AAD staining. The experiments were performed three times independently. Data are mean±SD.

(FIG. 6A) Knock-down of REC8 was confirmed at protein level in AGS and GES-1 cells by western blot. (FIG. 6B) REC8 knock-down significantly increased cell viability. (FIG. 6C) REC8 knock-down significantly promoted colony formation. (FIG. 6D) Knock-down of REC8 enhanced GES-1 cell migration ability, as shown by wound healing assay. All experiments were performed three times independently. Data are mean±SD.

(FIG. 7A) Downstream effectors of REC8 were identified by Human cancer pathway PCR array. (FIG. 7B) Expression of apoptotic, proliferative, migratory, and cell cycle-related genes was evaluated by western blot. GAPDH was used as a loading control. (FIG. 7C) Schematic diagram of the molecular events for REC8's function as a tumor suppressor through regulating cell cycle, proliferation, apoptosis and migration effectors.

(FIG. 8A) A typical CpG island is present at the promoter region of REC8. TSS, transcription start site. (FIG. 8B) Quantification by bisulfite genomic sequencing (BGS) on tissue samples showed that the promoter methylation level of REC8 was significantly higher in gastric tumor tissues than in non-tumor stomach tissues, well discriminating tumors from non-tumor tissues with an area under ROC curve of 0.9866. (FIG. 8C) HM450K methylation array data showed that the site covered by probe cg06351481 was methylated at highest level in the 398 gastric tumor samples tested in The Cancer Genome Atlas (TCGA) study.

(FIG. 9A) A duplex strategy with a pair of common primers and two probes for primer-probe design was employed targeting two selected CpG sites of REC8 covered by probe cg06351481 in HM450K methylation array. (FIGS. 9B & 9C) Although non-specific amplicons could be amplified from unconverted DNA of high concentration, no signal from the probes could be detected by qPCR, while methylated and unmethylated alleles amplified specifically from bisulfite-modified DNA (mDNA) templates could be distinguished by two different probes using this qPCR method.

(FIG. 11A) Quantification of REC8 methylation in gastric cancer cell lines using the new qPCR method showed rQ scores >0.7 for cells with fully methylated REC8 and low scores for the partially methylated SNU1 cell and the unmethylated GES-1 cell. (FIG. 11B) Sanger sequencing of the qPCR amplicons confirmed the quantification by qPCR.

(FIG. 12A) Quantification of REC8 methylation in tissue samples using the new qPCR method verified that REC8 was methylated at significantly higher levels in gastric tumor tissues than adjacent non-tumor tissues from Hong Kong and Beijing cohorts. (FIG. 12B) REC8 promoter was methylated at significantly higher levels in both gastric tumors and adjacent non-tumor tissues from gastric cancer (GC) patients as compared to stomach mucosas from non-GC subjects. (FIG. 12C) REC8 promoter methylation level quantitated by the new qPCR method well discriminated gastric tumor tissues from non-GC stomach, with an area under ROC curve of 0.9177 (P<0.0001).

(FIG. 14A) Quantification using the new qPCR method detected a significantly higher level of REC8 methylation in plasma samples from gastric cancer patients than healthy control subjects. (FIG. 14B) The level of methylated REC8 in plasma significantly discriminated gastric cancer patients from control subjects with an area under ROC of 0.813 (P<0.001). At the best cutoff value that maximizes the sum of sensitivity and specificity, methylated REC8 diagnosed gastric cancer patients at a sensitivity of 74.6% and specificity of 81.8%.

DEFINITIONS

Figure 1A:
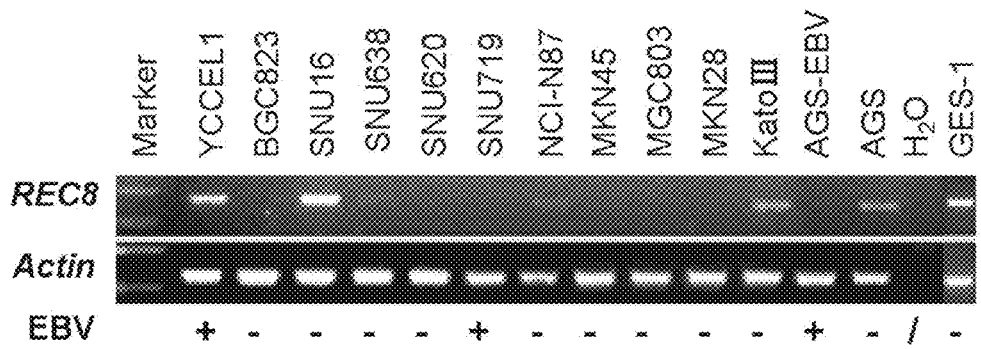
FIGS. 1A-1C. Transcriptional silencing of REC8 in gastric cancer is associated with DNA methylation.

The term "REC8 gene" or "REC8 protein," as used herein, refers to any naturally occurring variants or mutants, interspecies homologs or orthologs, or man-made variants of human REC8 gene or REC8 protein. The DNA sequence for a human wild-type REC8 mRNA is set forth in GenBank Accession No. NM_005132.2 (provided herein as SEQ ID NO:1), which translate to a coding sequence (provided as SEQ ID NO:2, the ALL CAPITAL LETTERS portion of SEQ ID NO:1, see Table 5) for a 547-amino acid REC8 protein (set forth in GenBank Accession No. NP_005123.2, provided herein as SEQ ID NO:4). An REC8 protein within the meaning of this application typically has at least 80%, or 90%, or 95% or higher sequence identity to the human wild-type REC8 protein (e.g., SEQ ID NO:4).

In this disclosure the terms "gastric cancer" and "stomach cancer" have the same meaning and refer to a cancer of the stomach or of stomach cells. Such cancers may be adenocarcinomas that occur in the lining of the stomach (mucosa or stomach epithelium) and may be in pylorus, body, or cardial (lower, body and upper) parts of the stomach. A "gastric cancer cell" is a stomach epithelial cell possessing characteristics of gastric cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human REC8 protein) or the translation of a protein encoded by a polynucleotide sequence. In other words, both mRNA level and protein level encoded by a gene of interest (e.g., human REC8 gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise endoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant REC8 protein used in the method of this invention (e.g., for treating gastric cancer) has at least 80% sequence identity, preferably 85%, 90%, 91%, 92%, 93, 94%, 95%, 96%, 97%, 98%, 99%, or 100% identity, to a reference sequence, e.g., a wild-type human REC8 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared.

When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=-2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C→U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, 180, 200, 250, or 300 contiguous nucleotides in length and contains at least 2, 3, 4, 5, 6, 7, 8, 9, 10, 11, 12, 13, 14, 15, 16, 17, 18, or 19 CpG pairs. For any one "CpG-containing genomic sequence" at a given location, e.g., within a region of the human REC8 genomic sequence (such as the region containing the promoter and exons 1-3, e.g., sequence segment shown in FIG. 1), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of REC8 mRNA or REC8 protein found in non-cancerous stomach tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human REC8 or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in the tables of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., REC8 mRNA or protein, that is present in an established normal disease-free tissue sample, e.g., a normal stomach epithelial tissue sample. The standard control value is suitable for the use of a method of the present invention, to serve as a basis for comparing the amount of REC8 mRNA or protein that is present in a test sample. An established sample serving as a standard control provides an average amount of REC8 mRNA or REC8 protein that is typical for a stomach epithelial tissue sample (e.g., stomach mucosa) of an average, healthy human without any stomach disease especially gastric cancer as conventionally defined. A standard control value may vary depending on the nature of the sample as well as other factors such as the gender, age, ethnicity of the subjects based on whom such a control value is established.

The term "average," as used in the context of describing a human who is healthy, free of any stomach disease (especially gastric cancer) as conventionally defined, refers to certain characteristics, especially the amount of human REC8 mRNA or protein, found in the person's stomach tissue, e.g., epithelial tissue or stomach mucosa, that are representative of a randomly selected group of healthy humans who are free of any stomach diseases (especially gastric cancer). This selected group should comprise a sufficient number of humans such that the average amount of REC8 mRNA or protein in the stomach mucosa among these individuals reflects, with reasonable accuracy, the corresponding amount of REC8 mRNA/protein in the general population of healthy humans. In addition, the selected group of humans generally have a similar age to that of a subject whose stomach tissue sample is tested for indication of gastric cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human REC8 mRNA or REC8 protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding REC8 mRNA is the amount of said polynucleotide to achieve an increased level of REC8 protein expression or biological activity, such that the symptoms of gastric cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, gastric cancer. Subjects also include individuals currently undergoing therapy that seek manipulation of the therapeutic regimen. Subjects or individuals in need of treatment include those that demonstrate symptoms of gastric cancer or are at risk of suffering from gastric cancer or its symptoms. For example, a subject in need of treatment includes individuals with a genetic predisposition or family history for gastric cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of REC8 protein are used to refer to inhibitory, activating, or modulating molecules, respectively, identified using in vitro and in vivo assays for REC8 protein binding or signaling, e.g., ligands, agonists, antagonists, and their homologs and mimetics. The term "modulator" includes inhibitors and activators. Inhibitors are agents that, e.g., partially or totally block carbohydrate binding, decrease, prevent, delay activation, inactivate, desensitize, or down regulate the activity of REC8 protein. In some cases, the inhibitor directly or indirectly binds to REC8 protein, such as a neutralizing antibody. Inhibitors, as used herein, are synonymous with inactivators and antagonists. Activators are agents that, e.g., stimulate, increase, facilitate, enhance activation, sensitize or up regulate the activity of REC8 protein. Modulators include REC8 protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

DETAILED DESCRIPTION OF THE INVENTION

I. Introduction

Gastric cancer patients often face a grim prognosis due to the nature of this disease in its lacking of specific symptoms during its early development stages. Early detection of gastric cancer is therefore critical for improving patient survival rate. Moreover, it is also of practical importance to predict the likelihood of mortality from gastric cancer among patients who have already received a diagnosis of gastric cancer for any time period after the initial diagnosis.

The present inventors discovered for the first time that expression of REC8, both at the mRNA and protein levels, is suppressed in gastric cancer cells. This suppressed expression of REC8 protein is due to increased methylation in the REC8 genomic sequence, especially in the promoter region of the gene, which leads to decreased transcription of REC8 mRNA. This discovery provides important means for detecting, monitoring, and treating gastric cancer. Generally, a lower than normal REC8 mRNA/protein level seen in a test subject, who may or may not exhibit any signs of digestive tract-related disorder or condition, indicates a high likelihood that the subject already has or will later develop gastric cancer. Similarly, a higher than normal level of methylation in the REC8 gene sequence, especially in the promoter region, indicates a high likelihood that the subject already has or will later develop gastric cancer. Further, among gastric cancer patients, individuals with lower level of REC8 expression in mRNA or protein or higher level of REC8 DNA methylation suffer a higher likelihood of mortality from gastric cancer during a post-diagnosis time period in comparison with their counterparts who have a normal or higher level of REC8 expression in mRNA or protein or a normal or lower level of REC8 DNA methylation.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human REC8 gene, and synthetic oligonucleotides (e.g., primers) can be verified using, e.g., the chain termination method for sequencing double-stranded templates of Wallace et al., *Gene* 16: 21-26 (1981).

III. Acquisition of Tissue Samples and Analysis of REC8 mRNA or DNA

The present invention relates to measuring the amount of REC8 mRNA or analyzing the methylation pattern of REC8 genomic DNA found in a person's stomach tissue, especially stomach epithelial sample, as a means to detect the presence, to assess the risk of developing, and/or to monitor the progression or treatment efficacy of gastric cancer. Thus, the first steps of practicing this invention are to obtain a stomach epithelial tissue sample from a test subject and extract mRNA or DNA from the sample.

A. Acquisition and Preparation of Stomach Tissue Samples

A stomach tissue sample is obtained from a person to be tested or monitored for gastric cancer using a method of the present invention. Collection of stomach epithelial tissue sample from an individual is performed in accordance with the standard protocol hospitals or clinics generally follow, such as during an endoscopy. An appropriate amount of stomach epithelium is collected and may be stored according to standard procedures prior to further preparation.

The analysis of REC8 mRNA or DNA found in a patient's stomach epithelial sample according to the present invention may be performed using, e.g., stomach mucosa. The methods for preparing tissue samples for nucleic acid extraction are well known among those of skill in the art. For example, a subject's stomach mucosa sample should be first treated to disrupt cellular membrane so as to release nucleic acids contained within the cells.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of human REC8 mRNA may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human REC8 mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in Diagnostic Molecular Biology: Principles and Applications pp. 401-406; Persing et al., eds., *Mayo Foundation, Rochester, Minn.*, 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of an mRNA species in a tissue sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA in a sample. For a review of branched-DNA signal amplification for direct quantitation of nucleic acid sequences in clinical samples, see Nolte, *Adv. Clin. Chem.* 33:201-235, 1998.

2. Other Quantitative Methods

The REC8 mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to REC8 mRNA can be used to detect the presence of such mRNA species and indicate the amount of mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques.

Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

C. Detection of Methylation in REC8 Genomic Sequence

Methylation status of a segment of REC8 genomic sequence containing one or more CpG (cytosine-guanine dinucleotide) pairs is investigated to provide indication as to whether a test subject is suffering from gastric cancer, whether the subject is at risk of developing gastric cancer, or whether the subject's gastric cancer is worsening or improving.

Typically a segment of the REC8 genomic sequence that includes the 5' untranslated region (such as the promoter region) and includes one or more CpG nucleotide pairs is analyzed for methylation pattern. For example, genomic sequence SEQ ID NO:5, the −112 to +120 segment of REC8 cDNA sequence shown in FIG. 1 or a portion thereof containing adequate number of CpG pairs can be used to determine how many of the CpG pairs within the sequence are methylated and how many are not methylated. The sequence being analyzed should be long enough to contain at least 1 (e.g., 2, 3, 4, 5, 10, or more) CpG dinucleotide pair and detection of methylation at this CpG site is typically adequate indication of the presence of gastric cancer cells. The length of the sequence being analyzed is usually at least 15 or 20 contiguous nucleotides, and may be longer with at least 25, 30, 50, 75, 100, 150, 180, or up to 200 or 230 contiguous nucleotides. At least one, typically 2 or more, often 3, 4, 5, 6, 7, 8, 9, 10, 11, 12, 13, 14, 15, 16, 17, 18, or 19, CpG nucleotide pairs are present within the sequence. In the cases of multiple (2 or more, such as 5, 10, 15) CpG sites are analyzed for methylation status (which may be 100% methylated or at least 50% methylated), when at least 50% of the CpG pairs within the analyzed genomic sequence are shown to be methylated, subject being tested is deemed to have gastric cancer or have an elevated risk of developing gastric cancer. As an example, SEQ ID NO:5, a segment of REC8 genomic sequence (−112 to +120 in relation to the transcription start site), can be chosen as a target sequence for the analysis. Some or majority of the CpG pairs in this region are found to be methylated in established gastric cancer cell lines and samples taken from gastric cancer, whereas non-cancerous stomach epithelial cells showed very few, if any at all, methylated CpG sites (see, e.g., FIGS. 1 and 2). For example, the presence of gastric cancer or an increased risk for later developing gastric cancer is established when at least 90% (or at least 17 or 18 CpG sites) of the 19 CpG sites within the region are found to be at least 50% methylated or when at least 50% (or at least 10 CpG sites) of the 19 CpG sites are found to be 100% methylated. For the purpose of determining the methylation pattern of an REC8 genomic sequence, bisulfite treatment followed by DNA sequencing is particularly useful, since bisulfite converts an unmethylated cytosine (C) to a uracil (U) while leaving methylated cytosines unchanged, allowing immediate identification through a DNA sequencing process. Optionally, an amplification process such as PCR is included after the bisulfite conversion and before the DNA sequencing.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. The DNA is then treated with a reagent capable of modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This unmethylated C U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996).

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA) (Xiong et al. 1997 *Nucleic Acids Res.* 25(12): 2532-2534), is useful for practicing the present invention. Other available methods for detecting DNA methylation include, for example, methylation-sensitive restriction endonucleases (MSREs) assay by either Southern blot or PCR analysis, methylation specific or methylation sensitive-PCR (MS-PCR), methylation-sensitive single nucleotide primer extension (Ms-SnuPE), high resolution melting (FIRM) analysis, bisulifte sequencing, pyrosequencing, methylation-specific single-strand conformation analysis (MS-SSCA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or Southern blot analysis. Exemplary methylation sensitive DNA cleaving reagent such as restriction enzymes include AatII, AciI, AclI, AgeI, AscI, Asp718, AvaI, BbrP1, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy99I, HpyCH4IV, KasI, MluI, NarI, NgoMIV, NotI, NotI-HF™, NruI, Nt.BsmAI, PaeR7I, PspXI, PvuI, RsrII, SacII, SalI, SalI-HF™, SfoI, SgrAI, SmaI, SnaBI or TspMI.

2. Optional Amplification and Sequence Analysis

Following the modification of DNA in a methylation-differential manner, the treated DNA is then subjected to sequence-based analysis, such that the methylation status of the REC8 genomic sequence may be determined. An amplification reaction is optional prior to the sequence analysis after methylation specific modification. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Quantitation of Polypeptides

A. Obtaining Samples

The first step of practicing the present invention is to obtain a sample of stomach epithelium from a subject being tested, assessed, or monitored for gastric cancer, the risk of developing gastric cancer, or the severity/progression of the condition. Samples of the same type should be taken from both a control group (normal individuals not suffering from any gastric disorder especially neoplasia) and a test group (subjects being tested for possible gastric cancer, for example). Standard procedures routinely employed in hospitals or clinics are typically followed for this purpose, as stated in the previous section.

For the purpose of detecting the presence of gastric cancer or assessing the risk of developing gastric cancer in test subjects, individual patients' stomach mucosa samples may be taken and the level of human REC8 protein may be measured and then compared to a standard control. If a decrease in the level of human REC8 protein is observed when compared to the control level, the test subject is deemed to have gastric cancer or have an elevated risk of developing the condition. For the purpose of monitoring disease progression or assessing therapeutic effectiveness in gastric cancer patients, individual patient's stomach epithelial samples may be taken at different time points, such that the level of human REC8 protein can be measured to provide information indicating the state of disease. For instance, when a patient's REC8 protein level shows a general trend of increase over time, the patient is deemed to be improving in the severity of gastric cancer or the therapy the patient has been receiving is deemed effective. A lack of change in a patient's REC8 protein level or a continuing trend of decrease on other hand would indicate a worsening of the condition and ineffectiveness of the therapy given to the patient. Generally, a lower REC8 protein level seen in a patient indicates a more severe form of the gastric cancer the patient is suffering from and a worse prognosis of the disease, as manifested in shorter life expectancy, higher rate of metastasis, resistance to therapy etc. Among gastric cancer patients, one who has a lower level of REC8 protein expression in the stomach cancer sample than that found in a second gastric cancer patient has a higher likelihood of mortality compared to the second patient for any defined time period, such as 1-5 years post-diagnosis.

B. Preparing Samples for REC8 Protein Detection

The stomach tissue sample from a subject is suitable for the present invention and can be obtained by well-known methods and as described in the previous section. In certain applications of this invention, stomach mucosa may be the preferred sample type.

C. Determining the Level of Human REC8 Protein

A protein of any particular identity, such as REC8 protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human REC8 protein) can also be detected by gel electrophoresis (such as 2-dimensional gel electrophoresis) and western blot analysis using specific antibodies. Alternatively, standard immunohistochemical techniques can be used to detect a given protein (e.g., human REC8 protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human REC8 protein) can be generated by known techniques.

Other methods may also be employed for measuring the level of REC8 protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any gastric disease (especially any form of tumor such as stomach cancer) as conventionally defined is first selected. These individuals are within the appropriate parameters, if applicable, for the purpose of screening for and/or monitoring gastric cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human REC8 mRNA or REC8 protein in the stomach tissue sample obtained from the group can be reasonably regarded as representative of the normal or average level among the general population of healthy people. Preferably, the selected group comprises at least 10 human subjects.

Once an average value for the REC8 mRNA or protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment and Prevention of Gastric Cancer

By illustrating the correlation of suppressed expression of REC8 protein and gastric cancer, the present invention further provides a means for treating patients suffering from gastric cancer: by way of increasing REC8 protein expression or biological activity. As used herein, treatment of gastric cancer encompasses reducing, reversing, lessening, or eliminating one or more of the symptoms of gastric cancer, as well as preventing or delaying the onset of one or more of the relevant symptoms.

Upon detecting suppressed expression of REC8 at mRNA/protein level cue to increased methylation level of REC8, especially at the promoter/exons 1-3 region (e.g., SEQ ID NO:5), one may establish the presence of gastric cancer in a patient or an increased risk of later developing the disease in the patient. As a result of this determination, the patient may be subject to subsequent therapies or preventive/monitoring measures, especially those fitting certain profiles, such as those with a family history of gastric cancer, such that the symptoms of these conditions may be prevented, eliminated, ameliorated, reduced in severity and/or frequency, or delayed in their onset. For example, a physician may prescribe both pharmacological and non-pharmacological treatments such as lifestyle modification (e.g., reduce body weight by 5% or more, assume a healthier life style including following a high fibre/low salt diet and maintaining a higher level of physical activities such as walking for at least 150 minutes weekly, and undergo routine screening/examination such as regular endoscopy). For those who have been detected as having a high risk of gastric cancer but not yet have the disease, various preventive measures can be taken, for instance, infection by *Helicobacter pylori* may be tested and treated with antibiotics as needed. Testing for *H. pylori* is recommended especially if a high risk patient has a first-degree relative, such as a parent; sibling, or child, who has been diagnosed with stomach cancer or with *H. pylori* infection. High risk patients can also be placed on a diet of increased portion of fresh vegetables and fruits, reduced portion to none of high salt foods such as preserved food items by drying, smoking, salting, or pickling, which tend to contain much more salt than fresh foods. Patients who have been deemed at a high risk of later developing gastric cancer should also be advised to avoid tobacco and alcohol use in order to further minimize the disease risk. In some cases, when the presence of gastric cancer is confirmed by way of other diagnostic means (e.g., endoscopy, pathological analysis of biopsy), aggressive treatment may be used such as surgical intervention as well as radio- and/or chemo-therapy.

A. Increasing REC8 Expression or Activity

1. Nucleic Acids Encoding REC8 Proteins

Enhancement of REC8 gene expression can be achieved through the use of nucleic acids encoding a functional REC8 protein. Such nucleic acids can be single-stranded nucleic acids (such as mRNA) or double-stranded nucleic acids (such as DNA) that can translate into an active form of REC8 protein under favorable conditions.

In one embodiment, the REC8-encoding nucleic acid is provided in the form of an expression cassette, typically recombinantly produced, having a promoter operably linked to the polynucleotide sequence encoding the REC8 protein. In some cases, the promoter is a universal promoter that directs gene expression in all or most tissue types; in other cases, the promoter is one that directs gene expression specifically in epithelial cells, especially in stomach epithelium. Administration of such nucleic acids can increase the REC8 protein expression in the target tissue, e.g., stomach epithelium. Since the human REC8 gene sequence encoding its mRNA is known as GenBank Accession No. NM_005132.2 and provided herein as SEQ ID NO:1, and its protein encoding sequence is provided herein as SEQ ID NO:2, one can derive a suitable REC8-encoding nucleic acid from the sequence, species homologs, and variants of these sequences.

2. REC8 Proteins

By directly administering an effective amount of an active REC8 protein to a patient suffering from gastric cancer and exhibiting suppressed REC8 protein expression or activity, the disease may also be effectively treated. For example, this can be achieved by administering a recombinantly produced REC8 protein possessing its biological activity to the patient suffering from gastric cancer. Formulations and methods for delivering a protein- or polypeptide-based therapeutic agent are well known in the art.

3. Activators of REC8 Protein

Increased REC8 protein activity can be achieved with an agent that is capable of activating the expression of REC8 protein or enhancing the activity of REC8 protein. For example, a demethylating agent (e.g., 5-Aza) may be able to activate REC8 gene expression by removing the suppression of REC8 gene expression caused by methylation of the promoter region of this gene. Other activating agents may include transcriptional activators specific for the REC8 promoter and/or enhancer. Such activating agents can be screened for and identified using the REC8 expression assays described in the examples herein.

Agonists of the REC8 protein, such as an activating antibody, are another kind of activators of the REC8 protein. Such activators act by enhancing the biological activity of the REC8 protein, typically (but not necessarily) by direct binding with the REC8 protein and/or its interacting proteins. Preliminary screening for such agonists may start with a binding assay for identifying molecules that physically interact with REC8 protein.

B. Pharmaceutical Compositions

1. Formulations

Compounds of the present invention are useful in the manufacture of a pharmaceutical composition or a medicament. A pharmaceutical composition or medicament can be administered to a subject for the treatment of gastric cancer.

Compounds used in the present invention, e.g., a REC8 protein, a nucleic acid encoding REC8 protein, or an activator of REC8 gene expression, are useful in the manufacture of a pharmaceutical composition or a medicament comprising an effective amount thereof in conjunction or mixture with excipients or carriers suitable for application.

An exemplary pharmaceutical composition for enhancing REC8 expression comprises (i) an express cassette comprising a polynucleotide sequence encoding a human REC8 protein as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

A REC8 protein or a nucleic acid encoding a REC8 protein can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., epithelial cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin of a patient, are preferably aqueous solutions, gels, capsules or pastes well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the patient. For example, transdermal devices are in the form of a bandage comprising a backing member, a reservoir containing the compound optionally with carriers, optionally a rate controlling barrier to deliver the compound to the skin of the patient at a controlled and predetermined rate over a prolonged period of time, and means to secure the device to the epithelium. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a REC8 protein or a nucleic acid encoding a REC8 protein, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., a REC8 protein or a nucleic acid encoding a REC8 protein, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The therapeutic agent can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that increases the level or activity of REC8 protein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control gastric cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of REC8 protein or nucleic acid encoding a REC8 protein will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for REC8 protein or a nucleic acid encoding a REC8 protein described herein are provided. Dosage for a REC8-encoding nucleic acid, such as an expression cassette, can be between 0.1-0.5 mg/use, with intravitreous administration (e.g., 5-30 mg/kg). Small organic compounds activators can be administered orally at between 5-1000 mg, or by intravenous infusion at between 10-500 mg/ml. Monoclonal antibody activators can be administered by intravenous injection or infusion at 50-500 mg/ml (over 120 minutes); 1-500 mg/kg (over 60 minutes); or 1-100 mg/kg (bolus) five times weekly. REC8 protein or peptide activators can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient (e.g., a REC8 protein or a nucleic acid encoding the protein). The additional therapeutic compound can also be administered separately, in a separate composition, or a different dosage form from the main active ingredient. Some doses of the main ingredient, such as a REC8 protein or a nucleic acid encoding a REC8 protein, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess the level of REC8 mRNA or REC8 protein in a subject, which can be used for various purposes such as detecting or diagnosing the presence of gastric cancer, determining the risk of developing gastric cancer, and monitoring the progression of gastric cancer in a patient, including assessing the likelihood of mortality from gastric cancer.

Kits for carrying out assays for determining REC8 mRNA level typically include at least one oligonucleotide useful for specific hybridization with at least one segment of the REC8 coding sequence or its complementary sequence. Optionally, this oligonucleotide is labeled with a detectable moiety. In some cases, the kits may include at least two oligonucleotide primers that can be used in the amplification of at least one segment of REC8 DNA or mRNA by PCR, particularly by RT-PCR. Table 5 provides some examples of suitable primers.

Kits for carrying out assays for determining REC8 protein level typically include at least one antibody useful for specific binding to the REC8A protein amino acid sequence. Optionally, this antibody is labeled with a detectable moiety. The antibody can be either a monoclonal antibody or a polyclonal antibody. In some cases, the kits may include at least two different antibodies, one for specific binding to the REC8 protein (i.e., the primary antibody) and the other for detection of the primary antibody (i.e., the secondary antibody), which is often attached to a detectable moiety.

Typically, the kits also include an appropriate standard control. The standard controls indicate the average value of REC8 protein or mRNA in the stomach epithelium of healthy subjects not suffering from gastric cancer. In some cases such standard control may be provided in the form of a set value. In addition, the kits of this invention may provide instruction manuals to guide users in analyzing test samples and assessing the presence, risk, or state of gastric cancer in a test subject.

In a further aspect, the present invention can also be embodied in a device or a system comprising one or more such devices, which is capable of carrying out all or some of the method steps described herein. For instance, in some cases, the device or system performs the following steps upon receiving a stomach tissue sample, e.g., a stomach mucosa sample taken from a subject being tested for detecting gastric cancer, assessing the risk of developing gastric cancer, or monitored for progression of the condition: (a) determining in sample the amount or concentration of REC8 mRNA, REC8 protein; (b) comparing the amount or concentration with a standard control value; and (c) providing an output indicating whether gastric cancer is present in the subject or whether the subject is at risk of developing gastric cancer, or whether there is a change, i.e., worsening or improvement, in the subject's gastric cancer condition. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Example 1: Tumor Suppressor REC8 is Epigenetically Down-Regulated in Gastric Cancer Introduction Gastric cancer is one of the most common malignant tumors and remains the third leading cause of cancer-related death worldwide.[1] Evidence from the inventors and other groups has shown that epigenetic alterations, particularly the inactivation of tumor suppressor genes by promoter hypermethylation, play an important role in the occurrence and development of gastric cancer.[2-5] EBV-associated gastric cancer is a characteristic subtype of gastric cancer, showing distinct clinicopathological features compared with EBV-negative ones.[6] Genome-wide EBV-associated DNA hypermethylation has been revealed in gastric cancer by comparing EBV-positive and EBV-negative gastric cancers.[7-9] Some genes, such as PTEN, CDHJ, APC, SSTRJ, TRABD and IHH, have been shown to be more frequently methylated in EBV-positive gastric cancer than in EBV-negative gastric cancer and to play tumor suppressive functions.[9-12]

In a previous study, the inventors compared the genome-wide methylation profiles between the gastric cancer cell line with stable EBV infection (AGS-EBV) and its parental uninfected AGS cells using the methylated DNA immunoprecipitation microarray (MeDIP-chip).[7] The promoter of the gene, REC8 meiotic recombination protein (REC8), was found to be methylated 23 times more in AGS-EBV cells than in AGS cells. Further expressional screening revealed that REC8 was down-regulated or silenced in most gastric cancer cell lines, including both EBV-positive and EBV-negative gastric cancer cells. REC8 belongs to the cohesin protein complex, which is essential for correct chromosome disjunction and homologous recombination in the mitotic and meiotic cycle.[13] In thyroid cancer, REC8 has been shown to be a tumor suppressor gene that is epigenetically regulated and robustly targeted by the PI3K pathway.[14] Aberrant methylation of REC8 has also been detected in the brain tissues of patients with schizophrenia.[15] REC8 methylation has been found in small and malignant gastrointestinal stromal tumors, and patients with methylation of REC8, PAX3, or CDKN2A had a significantly poorer prognosis.[16] The role of REC8 in gastric cancer remains elusive however. The present inventors thus set out to elucidate the expression and epigenetic regulation of REC8 in gastric cancer, with particular attention to the EBV subtype of gastric cancer. The biological function and molecular mechanism of REC8, as well as the clinical implication of its promoter methylation, were further investigated.

Results

REC8 was Down-Regulated in Gastric Cancer Cells by Promoter Methylation

Figure 1B:
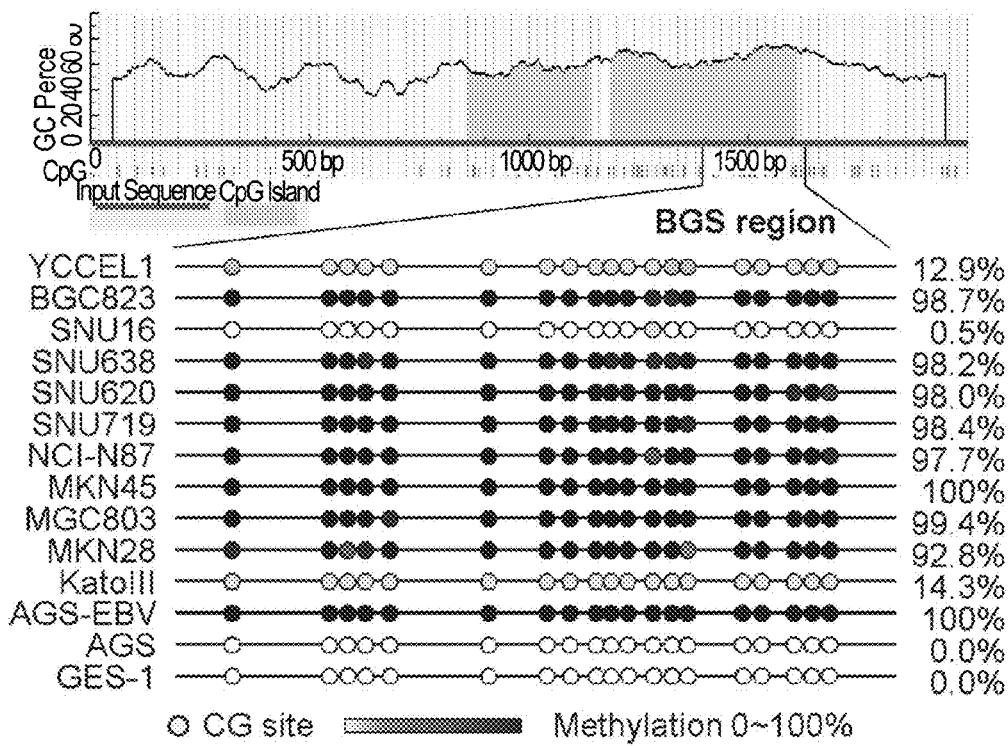
Figure 1C:
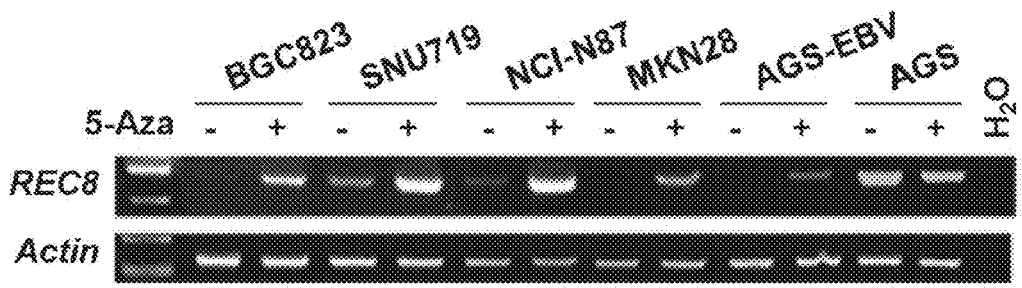

REC8 was down-regulated or silenced in 69.2% (9/13) of gastric cancer cell lines, including 3 EBV-positive and 10 EBV-negative, as indicated by RT-PCR (FIG. 1A). The methylation status of the REC8 promoter region was then characterized by BGS. Results showed that the REC8 down-regulation or silencing was correlated with its promoter methylation. All 9 cell lines with silenced REC8 (BGC823, SNU638, SNU620, SNU719, NCI-N87, MKN45, MGC803, MKN28 and AGS-EBV) showed full promoter methylation, while other cells with active REC8 expression (YCCEL1, SNU16, KatoIII, AGS and GES-1) showed no or only partial methylation (FIG. 1B). 6 cell lines were further treated with the DNA demethylation agent 5-Aza. REC8 mRNA expression was restored in the 5 cell lines with REC8 down-regulated/methylated (BGC823, SNU719, NCI-N87, MKN28 and AGS-EBV) but had no effect in AGS with REC8 expression/unmethylated (FIG. 1C), further supporting the hypothesis that the transcriptional silencing of REC8 is mediated by promoter methylation. These results collectively demonstrated that the expression of REC8 is mainly regulated by promoter methylation in gastric cancer cells.

Figure 2A:
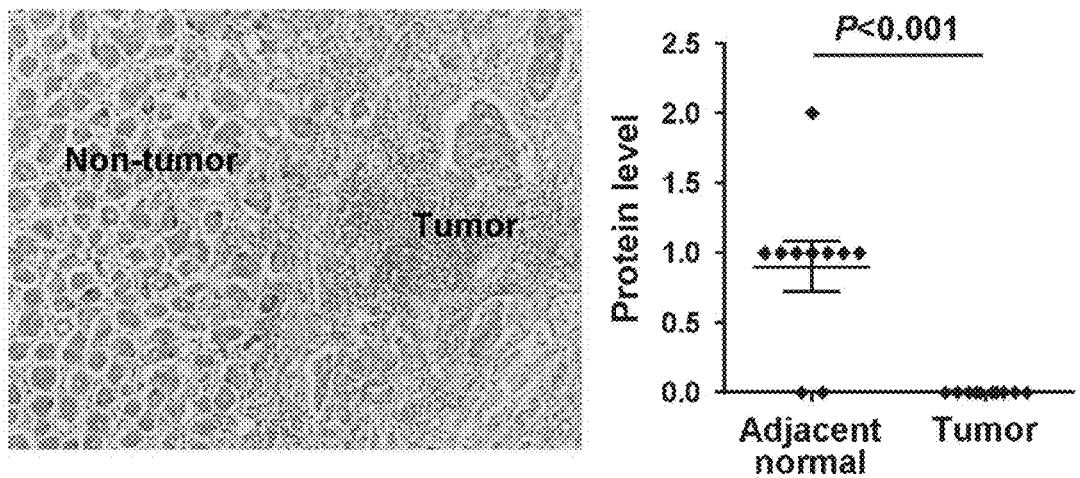
FIGS. 2A-2E. Reduced REC8 expression by promoter methylation in primary gastric tumors.
Figure 2B:
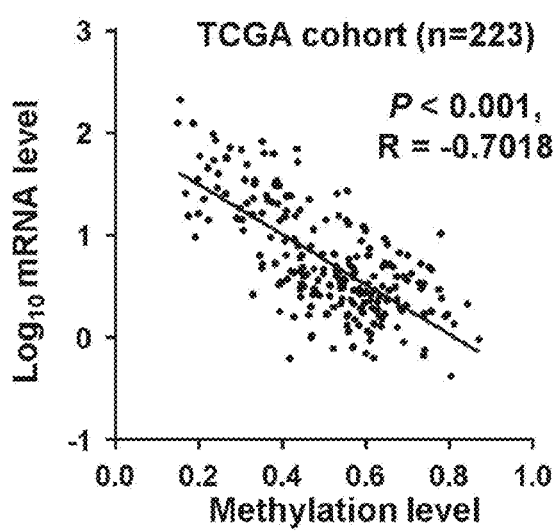
Figure 2C:
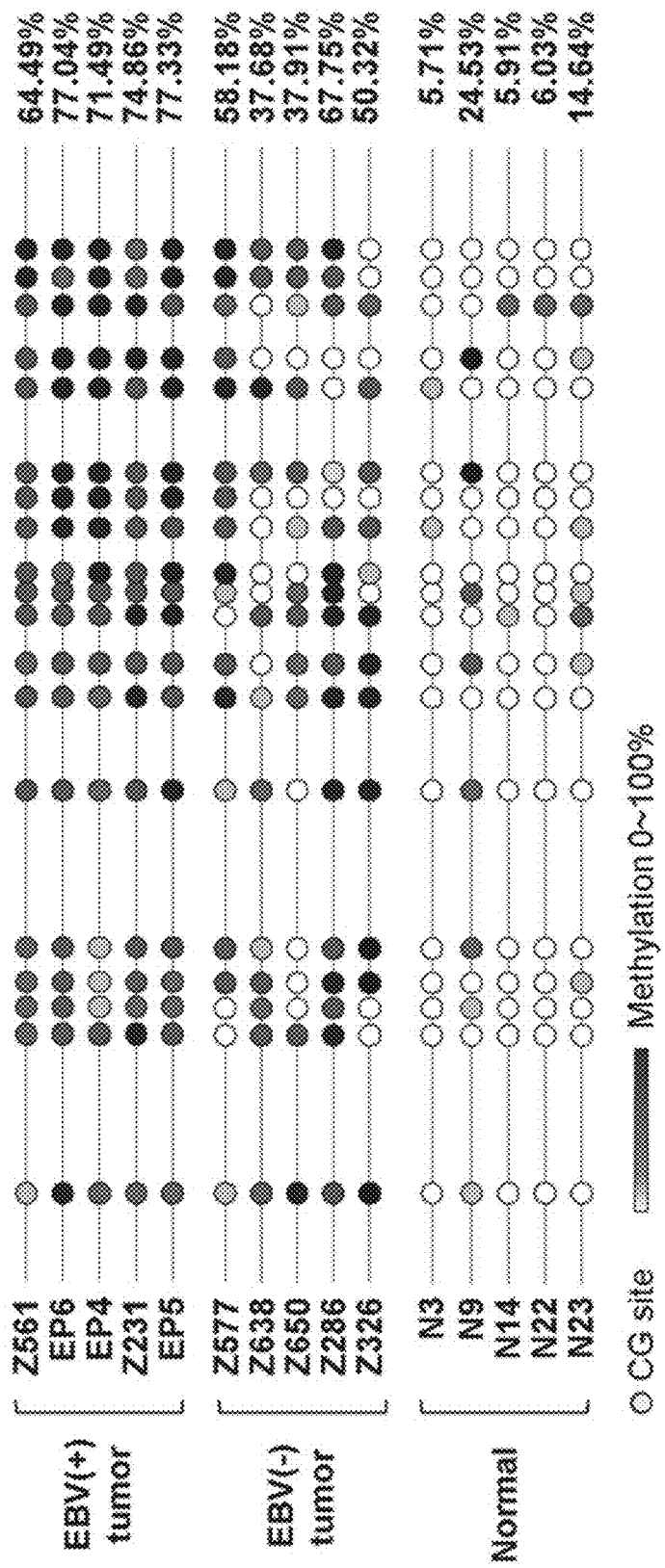
Figure 2D:
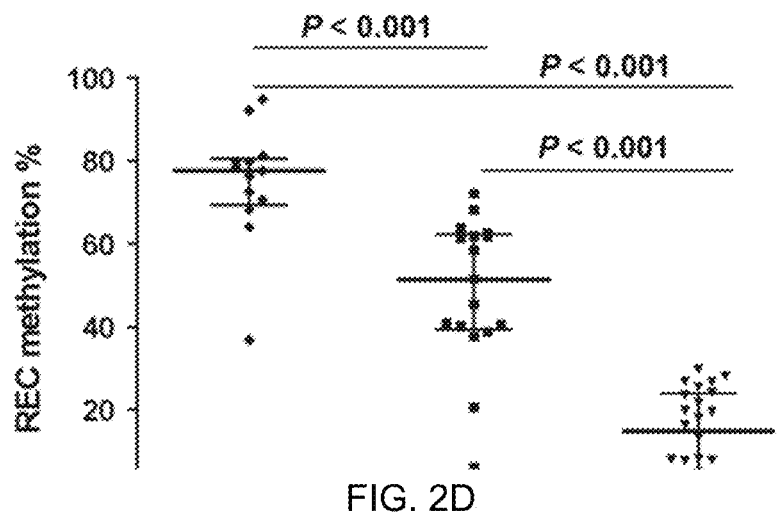
Figure 2E:
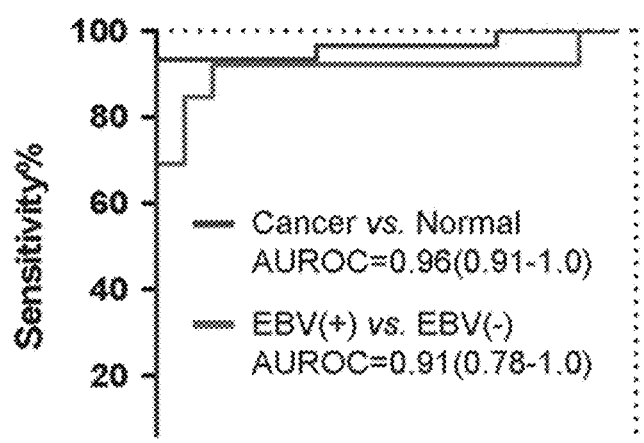

Promoter of REC8 was Hypermethylated in Primary Gastric Tumors, Especially the EBV-Positive Subtype As REC8 was down-regulated in both EBV-positive and EBV-negative gastric cancer cell lines, the expression and promoter methylation of REC8 were examined in both EBV-positive and EBV-negative primary gastric cancers. Immunohistochemistry analysis showed that REC8 protein expression was significantly reduced in gastric tumors as compared with adjacent non-tumor tissues of Chinese patients (FIG. 2A). Methylation and mRNA expression data on REC8 were retrieved from 223 gastric samples available in The Cancer Genome Atlas (TCGA) database. Linear regression analysis demonstrated a significant negative correlation between REC8 promoter methylation and mRNA expression (R=−0.7018, P<0.001; FIG. 2B), suggesting a pivotal regulatory role of promoter methylation on REC8 expression in gastric cancer. The methylation levels of REC8 in EBV-positive, EBV-negative primary gastric tumors and normal stomach mucosa of Chinese subjects were further compared by BGS (FIG. 2C). REC8 promoter was methylated at significantly higher levels in both EBV-positive gastric tumors (74.8±3.9%, n=13) and EBV-negative gastric tumors (48.9±4.3%, n=18) as compared to normal stomach mucosa (14.4±2.0%, n=24) (both P<0.001); the methylation level was significantly higher in EBV-positive tumors than in EBV-negative tumors (P<0.001) (FIG. 2D). Receiver Operating Characteristic (ROC) curve analysis indicated that a cut-off value of 33.4% REC8 methylation could discriminate gastric tumors from normal mucosa with a sensitivity and specificity of 93.3% and 100%, respectively [AUC=0.96 (0.911.0)], and a cut-off value of 68.1% could discriminate EBV-positive tumors from EBV-negative tumors with a sensitivity and specificity of 84.6% and 94.1%, respectively [AUC=0.91(0.78-1.0)] (FIG. 2E). In all 31 cancer patients (13 EBV-positive and 18 EBV-negative), linear regression analysis showed that REC8 methylation was significantly associated with positive EBER-staining/EBV-positivity (linear coefficient: 23.73, 95% CI: 10.72-36.74; P=0.001), but not with other clinicopathological features such as age, gender, H. pylori infection, histological type, differentiation and TNM staging (Table 1). REC8 is frequently methylated in gastric cancers, with EBV infection being one of the important factors for the high methylation level of REC8 promoter.

Figure 3A:
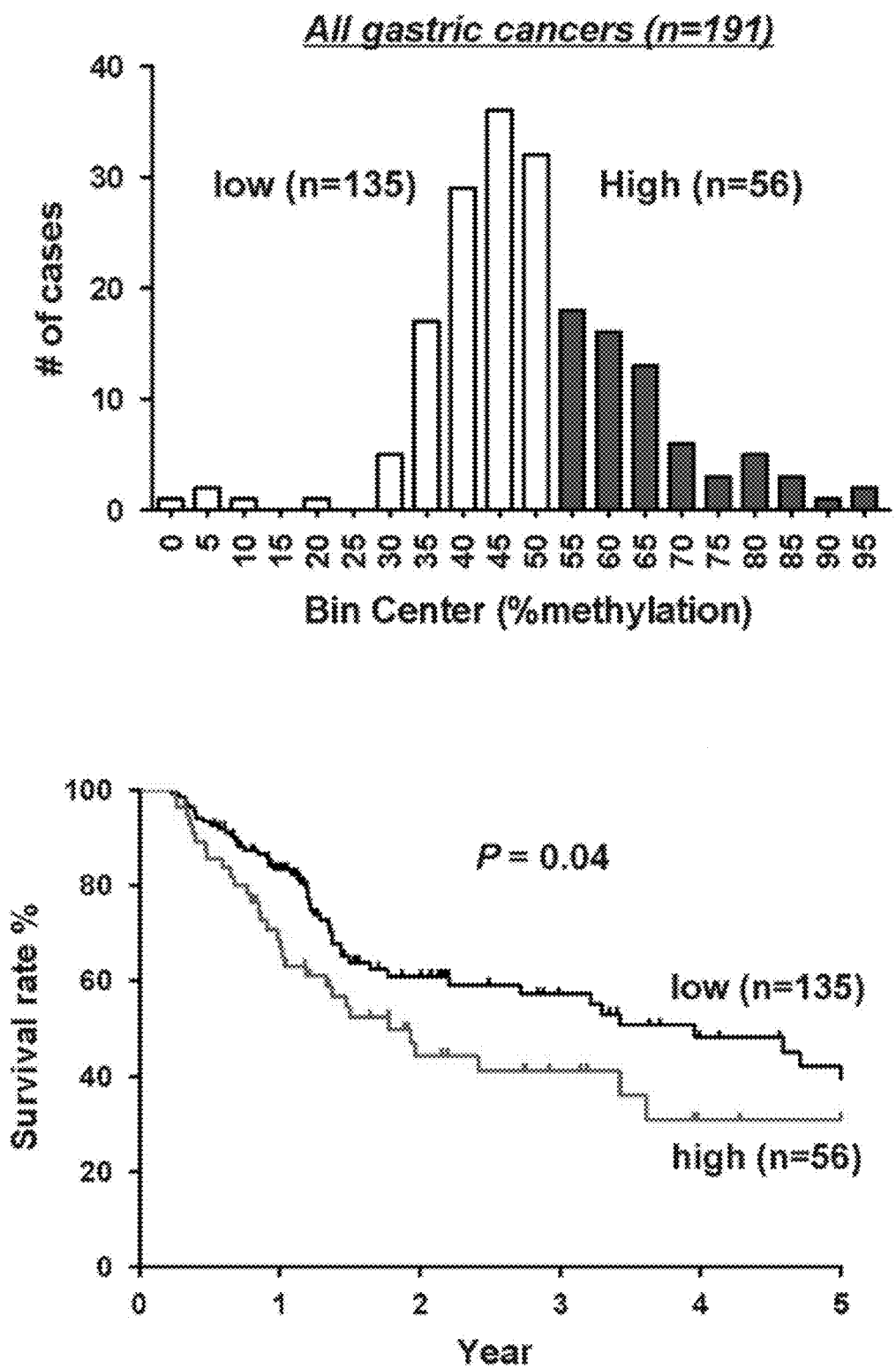
FIGS. 3A-3B. Promoter methylation of REC8 in Chinese gastric cancer patients.
Figure 3B:
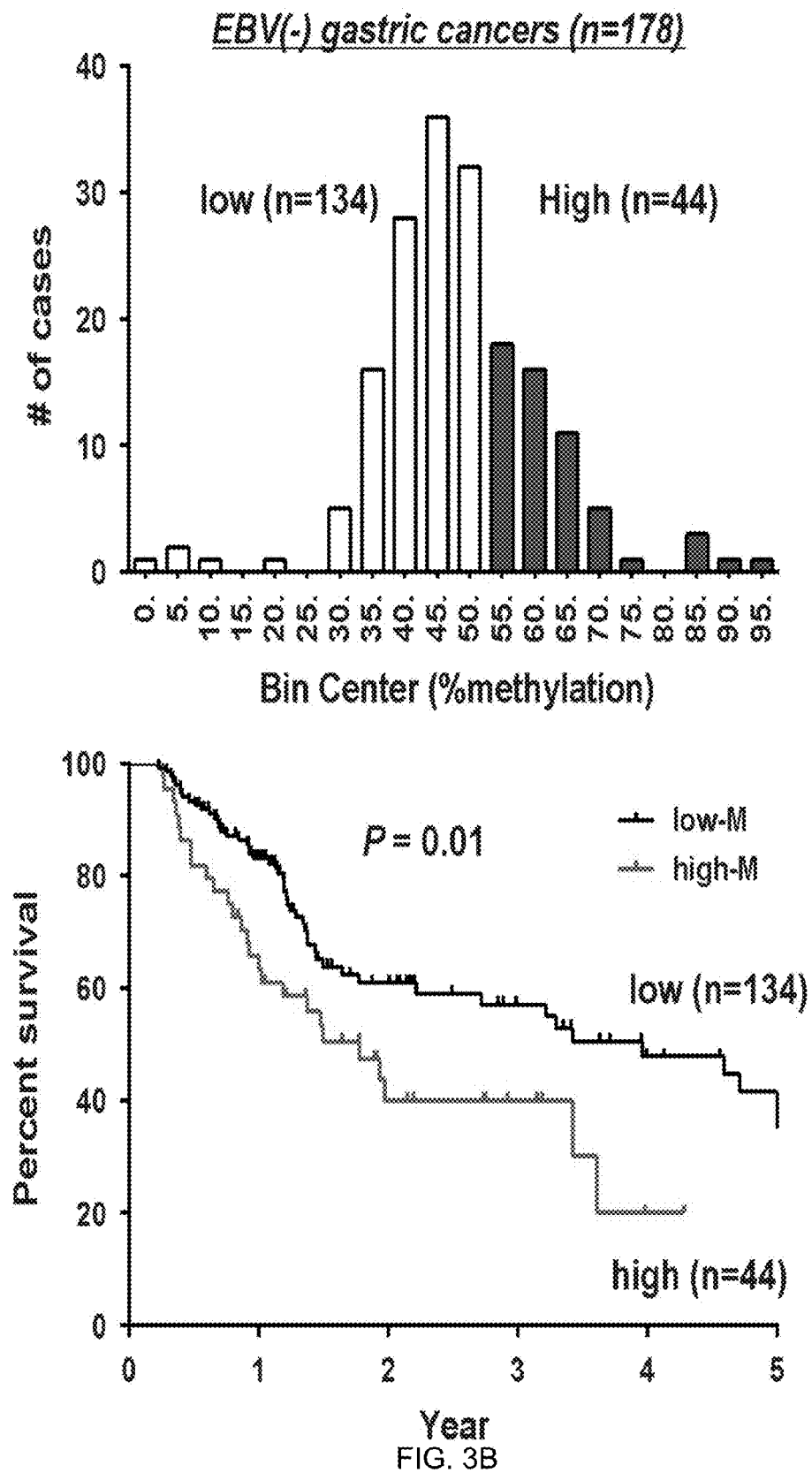

Clinicopathological Features of REC8 Promoter Methylation in Gastric Cancer Patients In order to delineate the clinical implications of REC8 promoter methylation in gastric cancer patients, the promoter methylation levels of REC8 were quantitated by BGS in 191 Chinese gastric cancer patients with follow-up data (median survival time: 1.24 years). Analysis of survival data was limited within a 5-year period to avoid the probability of death not due to gastric cancer. The cut-off value of 33.4% was calculated using ROC curve analysis as the level that maximizes the sum of sensitivity and specificity in discriminating cancer from normal mucosa. Using this level, the inventors found REC8 to be methylated in 94.2% (180 of 191) cases of primary gastric cancers. Using Cutoff Finder for survival significance analysis,[17] the 191 gastric cancers were classified as low- and high-methylated using the cut-off value of 55%; the distribution histogram of which is shown in FIG. 3A. As shown in the Kaplan-Meier survival curves, Chinese gastric cancer patients with high-methylation of REC8 promoter, regardless of EBV infection status, had a significantly shortened survival than those with low-methylation (P=0.04, log-rank test; FIG. 3A). There was no correlation between low/high-methylation of REC8 and clinicopathological features, such as age, gender, H. pylori infection status, Lauren type, differentiation, and TNM stage (Table 2). As an increase in survival was reported in patients with EBV-positive gastric cancer compared to those of EBV-negative,[6] survival analysis on EBV-negative gastric cancers was performed (n=178). As expected, high-methylation of REC8 promoter was significantly associated with shortened survival of patients with EBV-negative gastric cancer (P=0.01; FIG. 3B), which was more obvious than in all patients (FIG. 3A).

High-Methylation of REC8 Promoter is an Independent Predictor of Poor Outcome in Patients with Gastric Cancer Using univariate and multivariate Cox regression analyses, only REC8 methylation status and tumor stage, but not other clinicopathological features (age, gender, H. pylori infection status, Lauren type, differentiation), were found to be significantly associated with the poor survival of all the 191 Chinese gastric cancer patients (Table 3). Multivariate Cox regression analysis showed that high-methylation of the REC8 promoter, as an independent predictor of poor survival in gastric cancer patients, showed a hazard ratio (HR) of 1.68 (P<0.05). When only EBV-negative gastric cancers (n=178) were considered, similarly only REC8 methylation status and tumor stage were found to be significantly associated with shortened patient survival, with an increased HR (1.86) as revealed by multivariate Cox regression analysis for REC8 methylation (Table 3).

REC8 Exerted an Inhibitory Effect on Gastric Cancer Growth

Figure 4A:
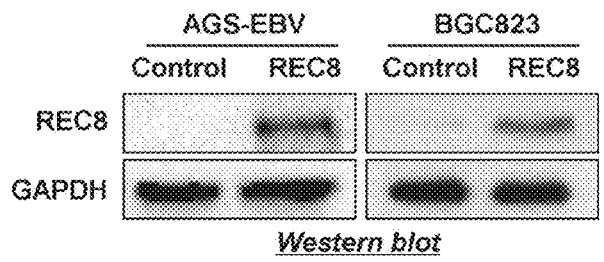
FIGS. 4A-4D. REC8 overexpression inhibits the growth of gastric cancer cells.
Figure 4B:
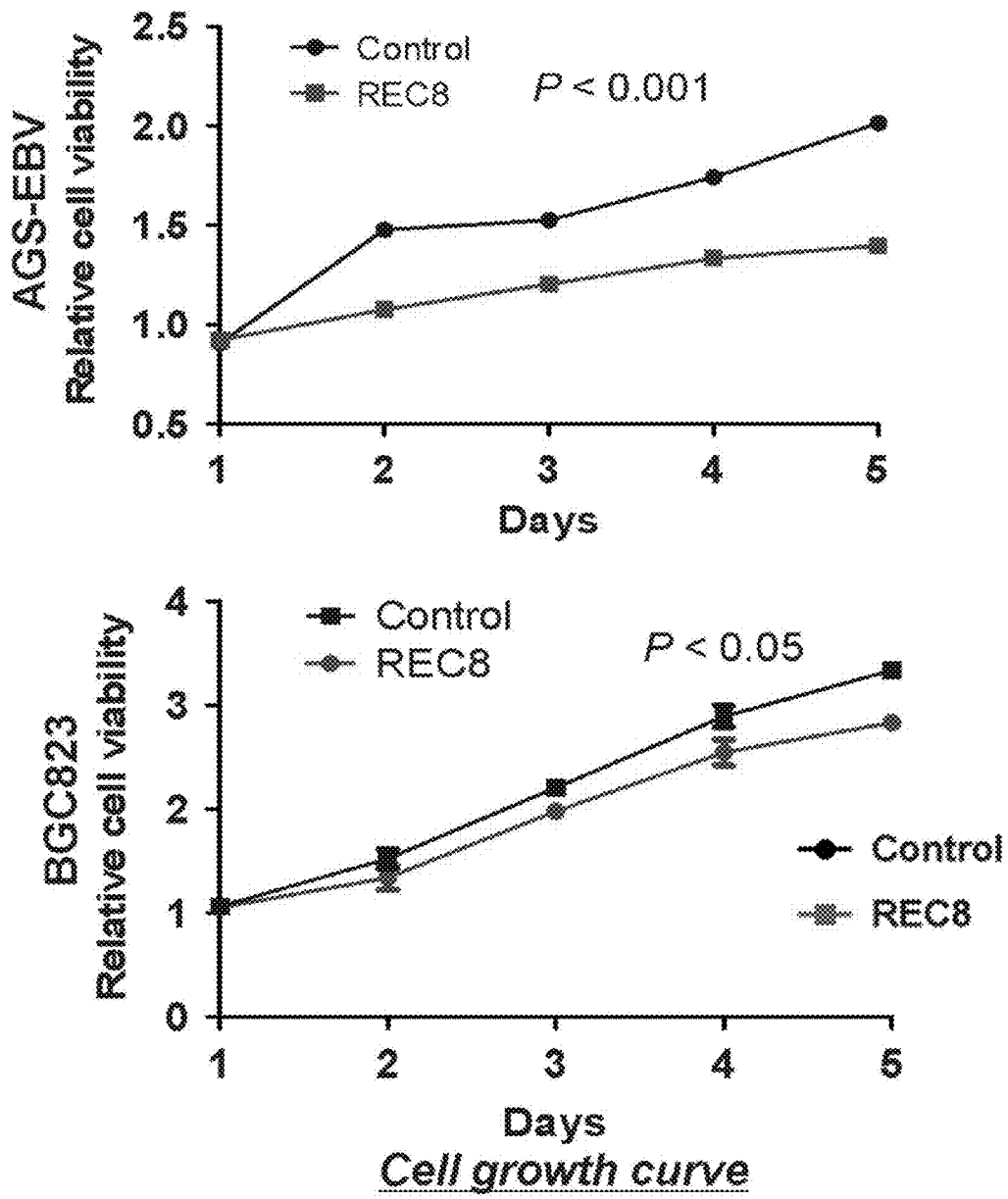
Figure 4C:
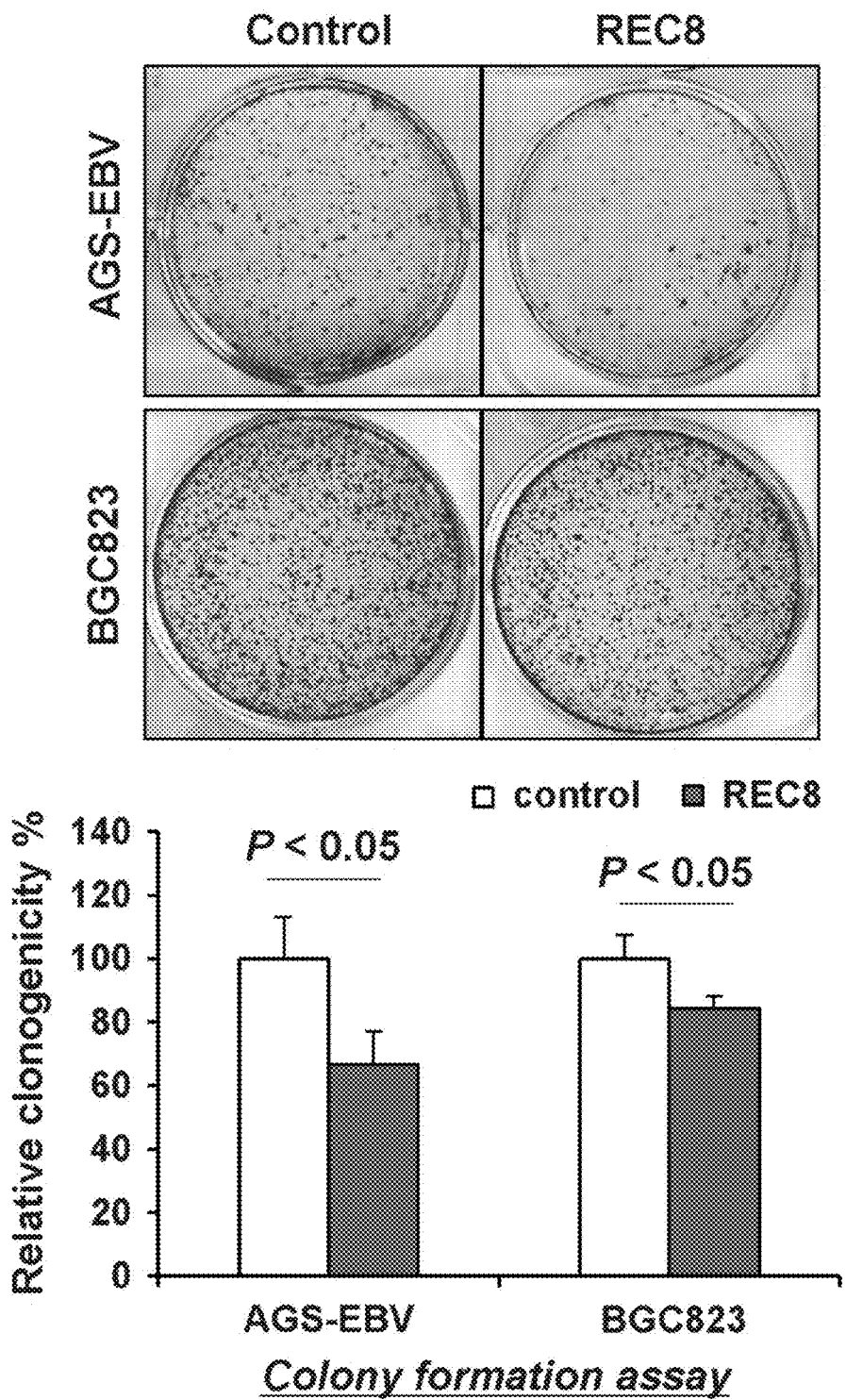
Figure 4D:
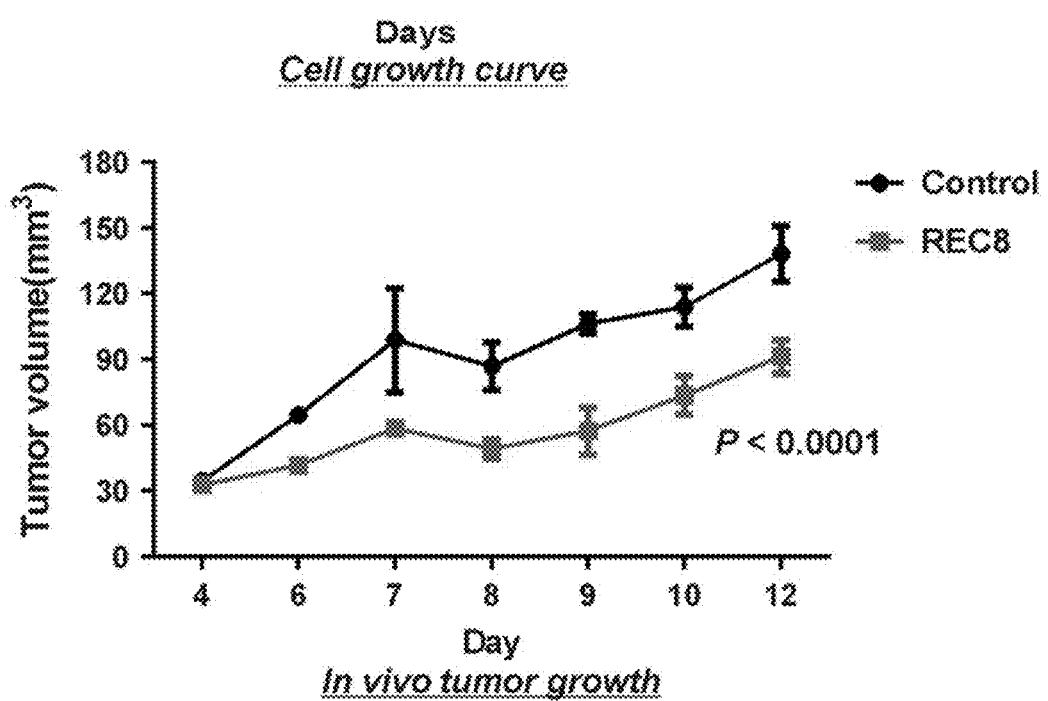

To investigate the role of REC8 in gastric cancer, EBV-positive AGS-EBV and EBV-negative BGC823 cells were transfected with REC8 expression vector or empty control vector. Overexpression of REC8 was confirmed by western blot (FIG. 4A). REC8 expression significantly suppressed cell viability of both cell lines as compared with the empty vector transfection (P<0.05; FIG. 4B). The growth suppressive effect of REC8 was further confirmed by the significantly reduced colony formation ability of REC8-overexpressed cells as compared with controls (P<0.05; FIG. 4C). Moreover, REC8 expression was found to significantly suppress tumorigenicity in vivo (P<0.05; FIG. 4D). These results demonstrated that REC8 functions as a tumor suppressor in gastric cancer.

Figure 5A:
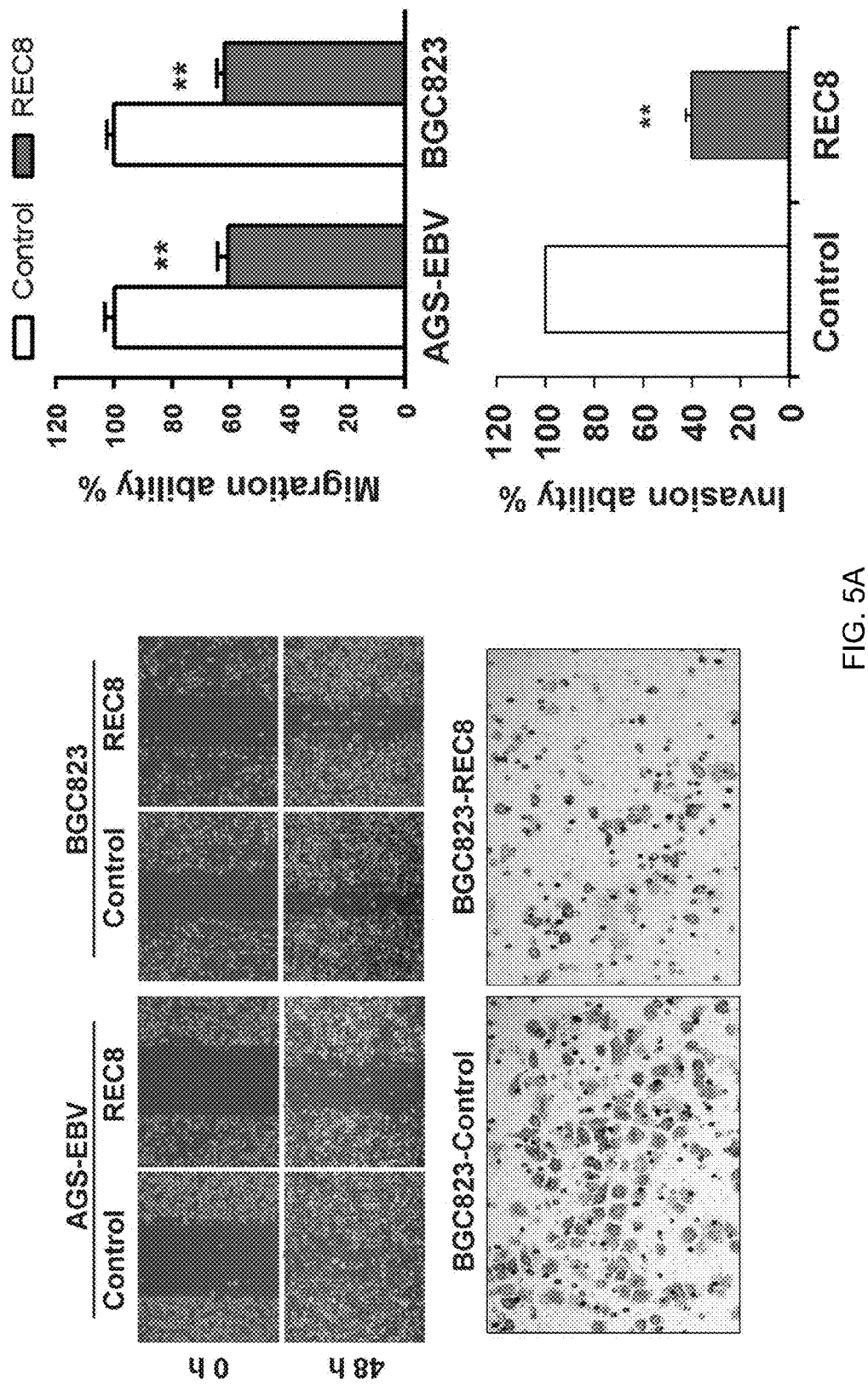
FIGS. 5A-5C. REC8 suppressed migration ability and cell cycle progression, and induced apoptosis in gastric cancer cells.

REC8 Suppressed Migration and Invasion Ability, Inhibited Cell Cycle Progression and Induced Apoptosis in Gastric Cancer Cells To further understand the tumor suppressive role of REC8, the effect of REC8 overexpression on gastric cancer cell migration was next investigated using the monolayer scratch healing assay and Matrigel invasion assay. Overexpression of REC8 markedly slowed the migration of AGS-EBV and BGC823 cells. Significant reduction in wound closure was observed at 48 h in REC8-overexpressed cells as compared with control cells for both cell lines (P<0.001; FIG. 5A), In addition, REC8 also significantly impaired the invasiveness of BGC823 cells. These results demonstrated an inhibitory effect of REC8 on gastric cancer cell migration and invasion.

Figure 5B:
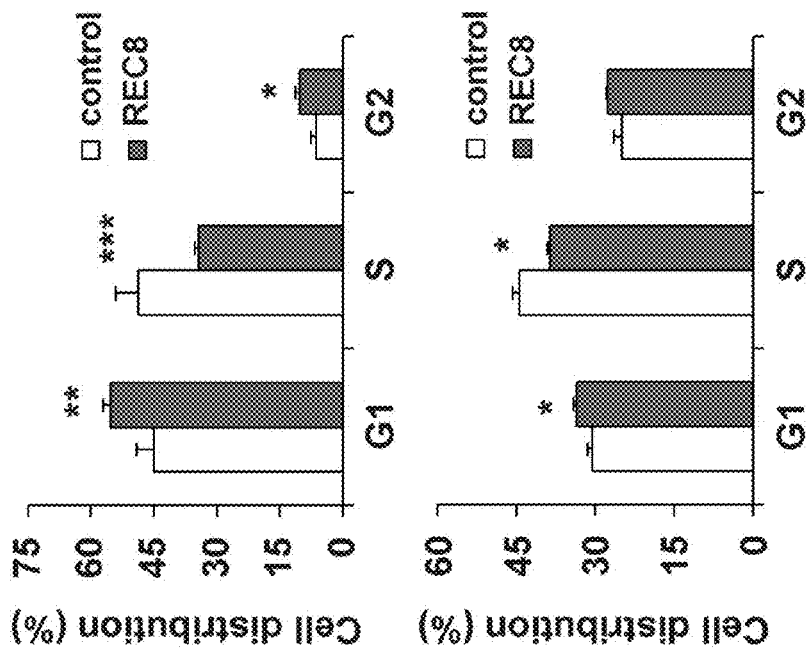
Figure 5B:
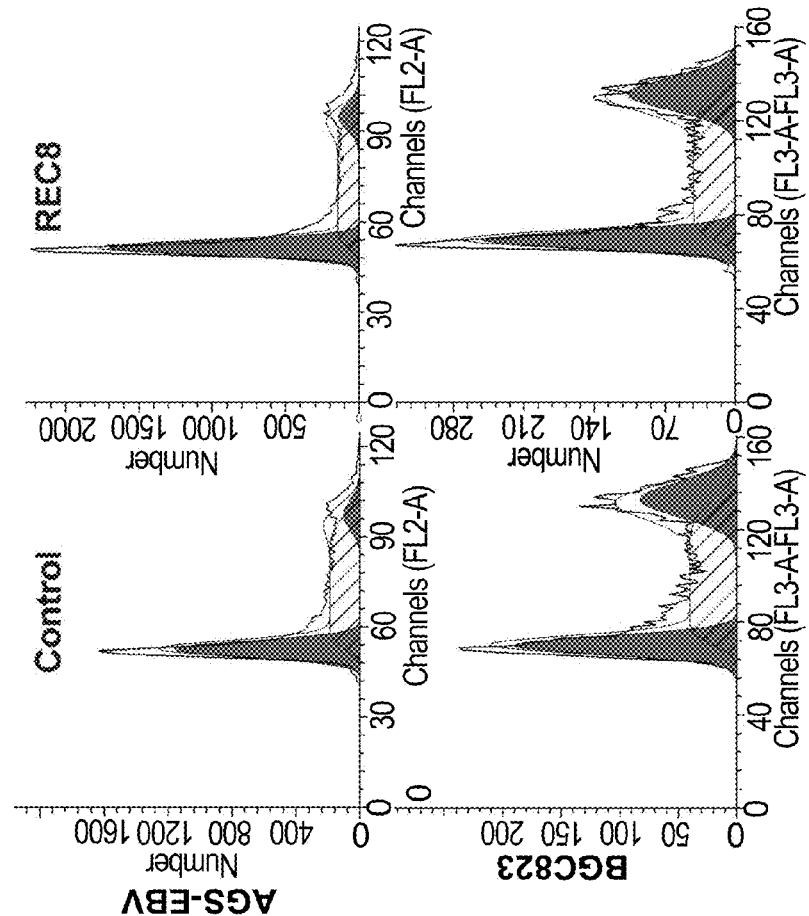
Figure 5C:
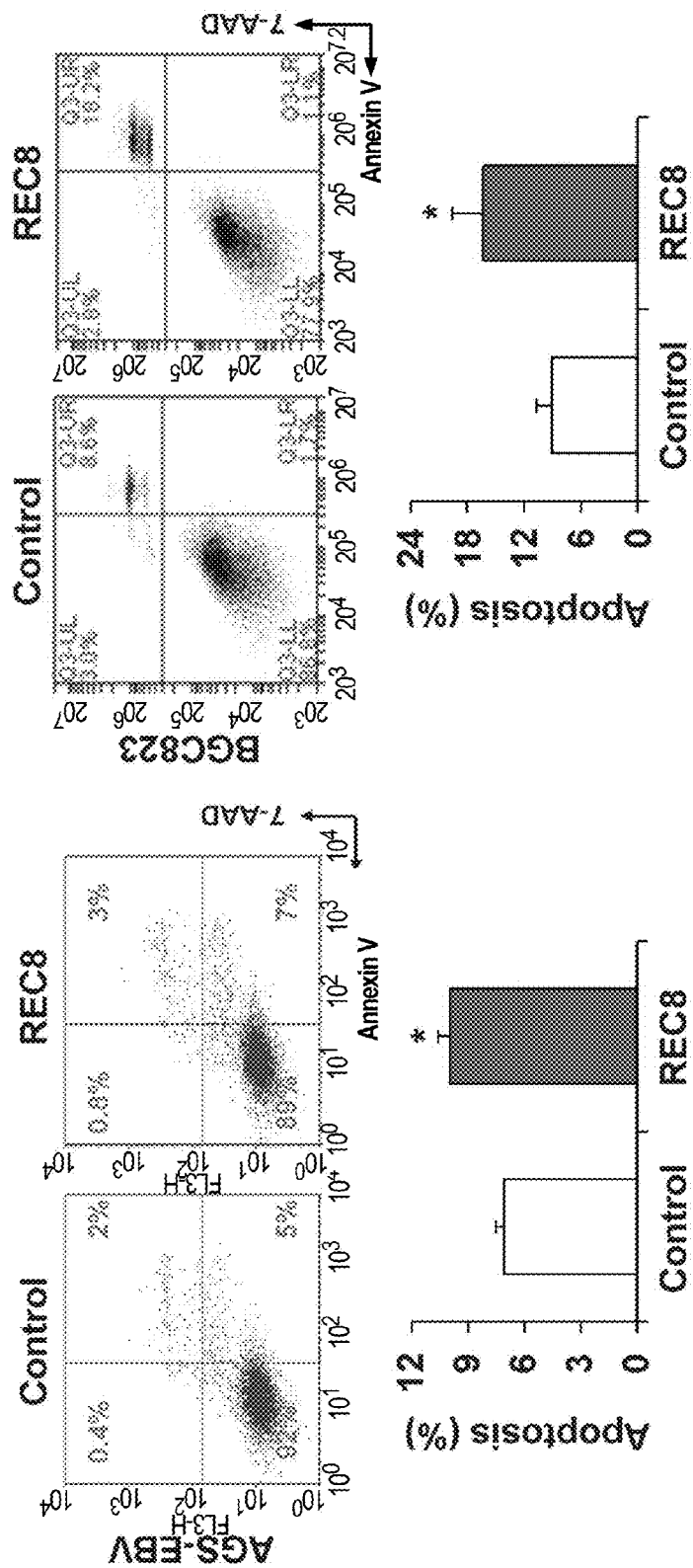

The effect of REC8 on cell cycle distribution and apoptosis were further analyzed by flow cytometry after propidium iodide staining or dual staining with viability dye 7-AAD and Annexin V-FITC. Ectopic expression of REC8 led to a significant increase of cells in G1 phase (P<0.05) and a significant reduction of those in S phase (P<0.001) in both AGS-EBV and BGC823 cells (FIG. 5B). Expression of REC8 also significantly increased the apoptotic cell proportion in both cell lines (P<0.05; FIG. 5C). These results demonstrated that REC8 suppressed gastric cancer cell growth via inhibiting cell cycle progression and inducing cell apoptosis.

Knock-Down of REC8 Promoted Cell Growth and Migration

Figure 6A:
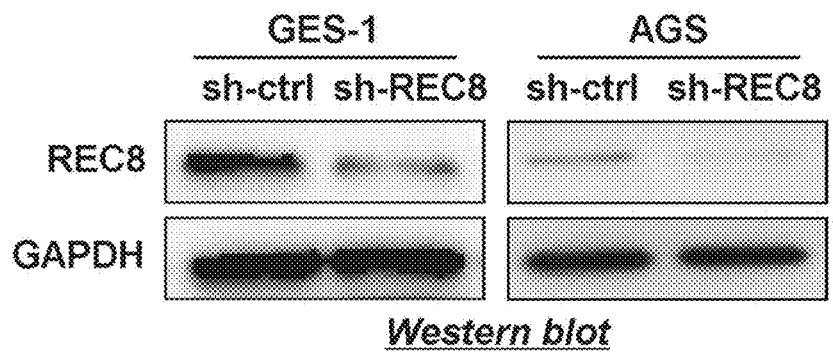
FIGS. 6A-6D. REC8 knock-down increased gastric cancer cell growth and migration.
Figure 6B:
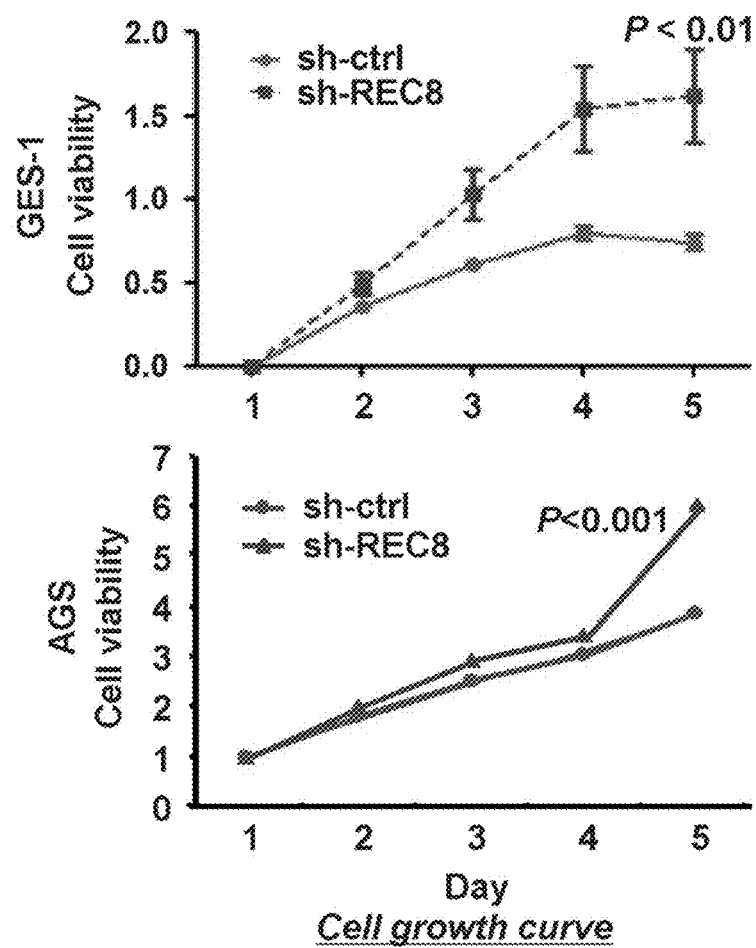
Figure 6C:
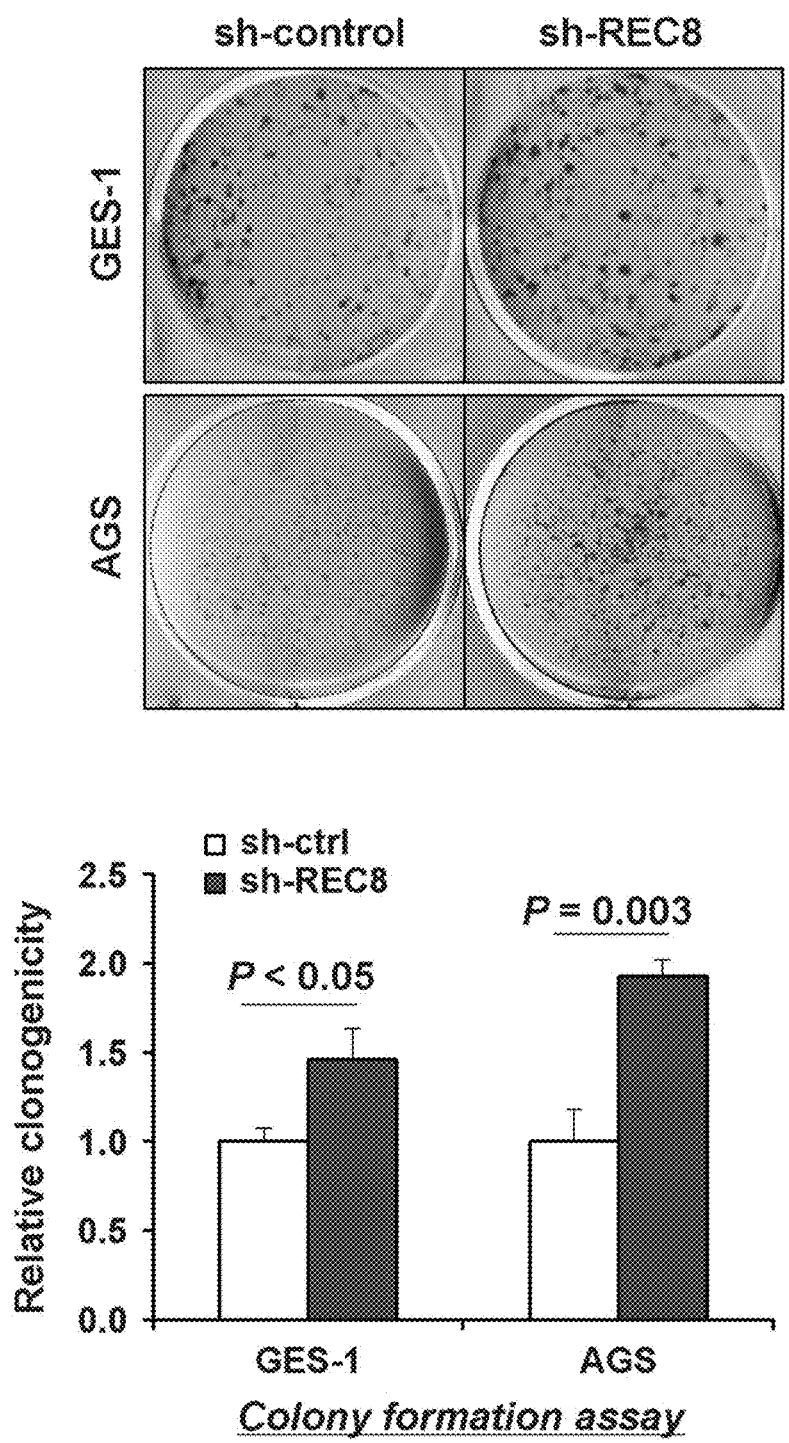
Figure 6D:
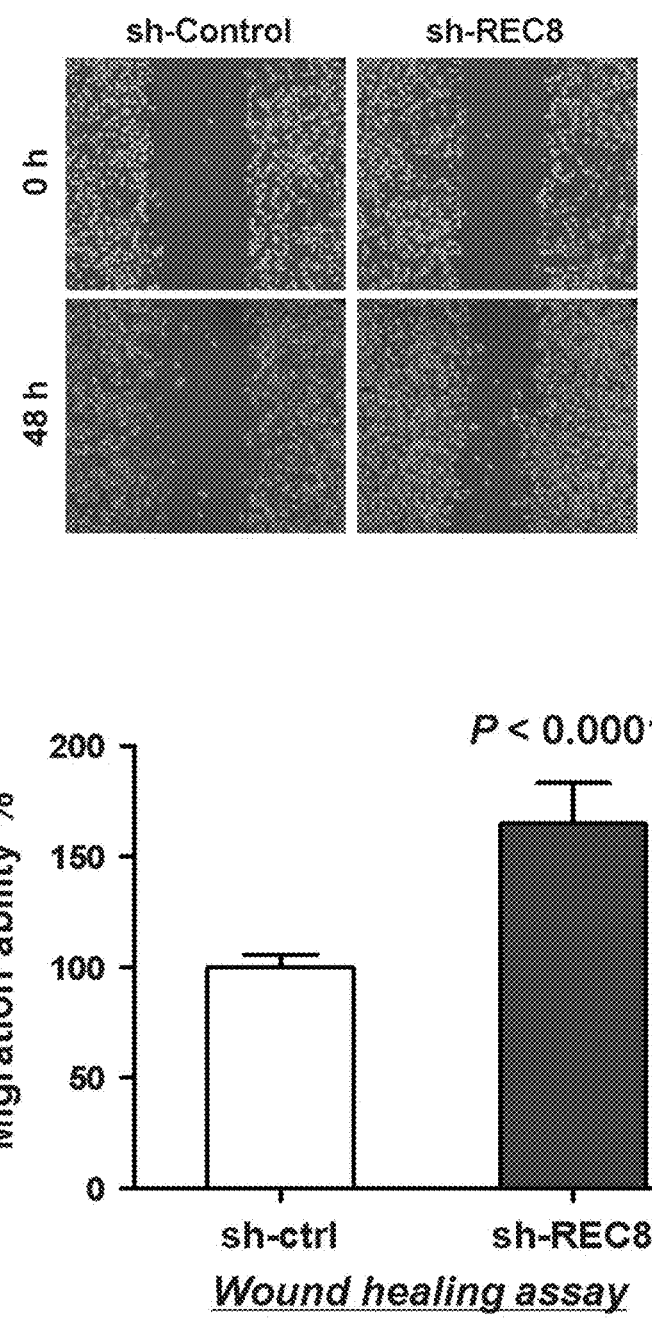

To further confirm the inhibitory effect of REC8 on gastric cancer cell growth, REC8 expression was knocked down in the immortalized human gastric epithelial mucosa cell line, GES-1, and the gastric cancer cell line, AGS, which showed high endogenous expression of REC8. Successful knock-down of REC8 was confirmed by western blot after stable transfection of the short hairpin RNA (shRNA)-REC8 vectors (FIG. 6A). Knock-down of REC8 significantly increased cell viability in both GES-1 and AGS cells as compared with their controls transfected with scrambled-shRNA vectors (P<0.01; FIG. 6B). The growth enhancive effect of REC8 knock-down was further supported by colony formation assay. The colonies formed by shRNA-REC8 transfected cells were significantly more in number and larger in size as compared with those formed by control cells (P<0.05; FIG. 6C). Stable knock-down of REC8 also markedly accelerated cell migration at the edges of scratch wounds (FIG. 6D). Quantitative analysis at 48 h indicated a significant increase in the migration ability of GES-1 cells transfected with shRNA-REC8 compared with the control cells (P<0.05). These promoting effects on cell growth and migration by knock-down of REC8 further confirmed the tumor suppressive role of REC8 in gastric cancer.

Identification of Genes Modulated by REC8

Figure 7A:
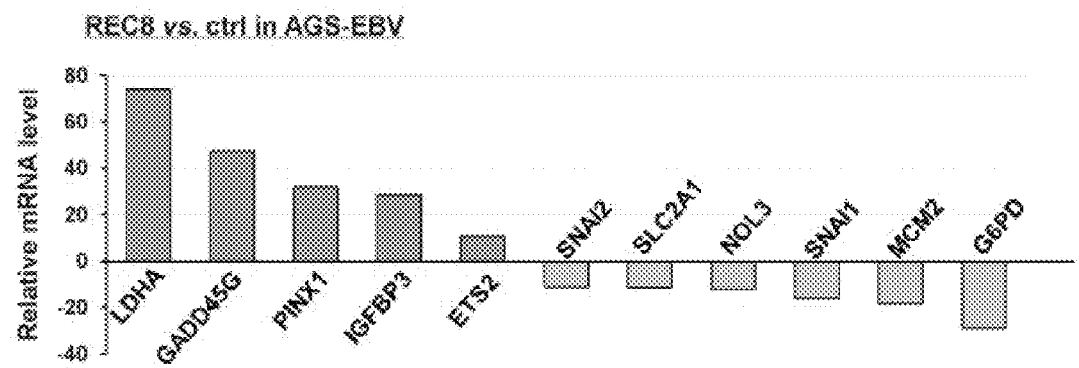
FIGS. 7A-7C. Molecular mechanism of the tumor suppressive role of REC8 in gastric cancer.

To gain insight into the molecular mechanism underlying the tumor suppressive effect of REC8, the expression of 84 pivotal genes involved in cancer pathways were analyzed by Human Cancer Pathway cDNA array in AGS-EBV cells with/without REC8 expression. REC8 was found to modulate the expression of important genes involved in multiple cellular processes, including proliferation, cell cycle, apoptosis, migration and differentiation (FIG. 7A). REC8 inhibited the cell proliferation regulators (G6PD and SLC2A1) and apoptosis inhibitor (NOL3), while inducing expression of the apoptosis regulator (GADD45G) and tumor suppressors (PinX1, IGFBP3 and ETS2), which may ultimately inhibit cell proliferation and increase cell apoptosis. REC8 also inhibited the cell cycle G1-S transition-promoting regulator, MCM2, which may subsequently mediate cell cycle arrest at G1-S transition. Moreover, REC8 reduced the expression of two Epithelial-Mesenchymal Transition (EMT) promoters (SNAI1 and SNAI2) and induced the migration inhibitor LDHA, resulting in inhibited cell migration ability.

Figure 7B:
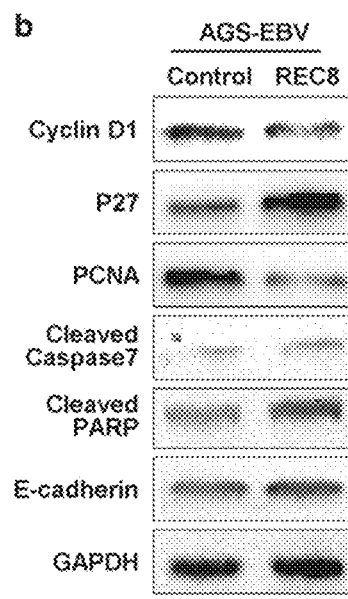
Figure 7C:
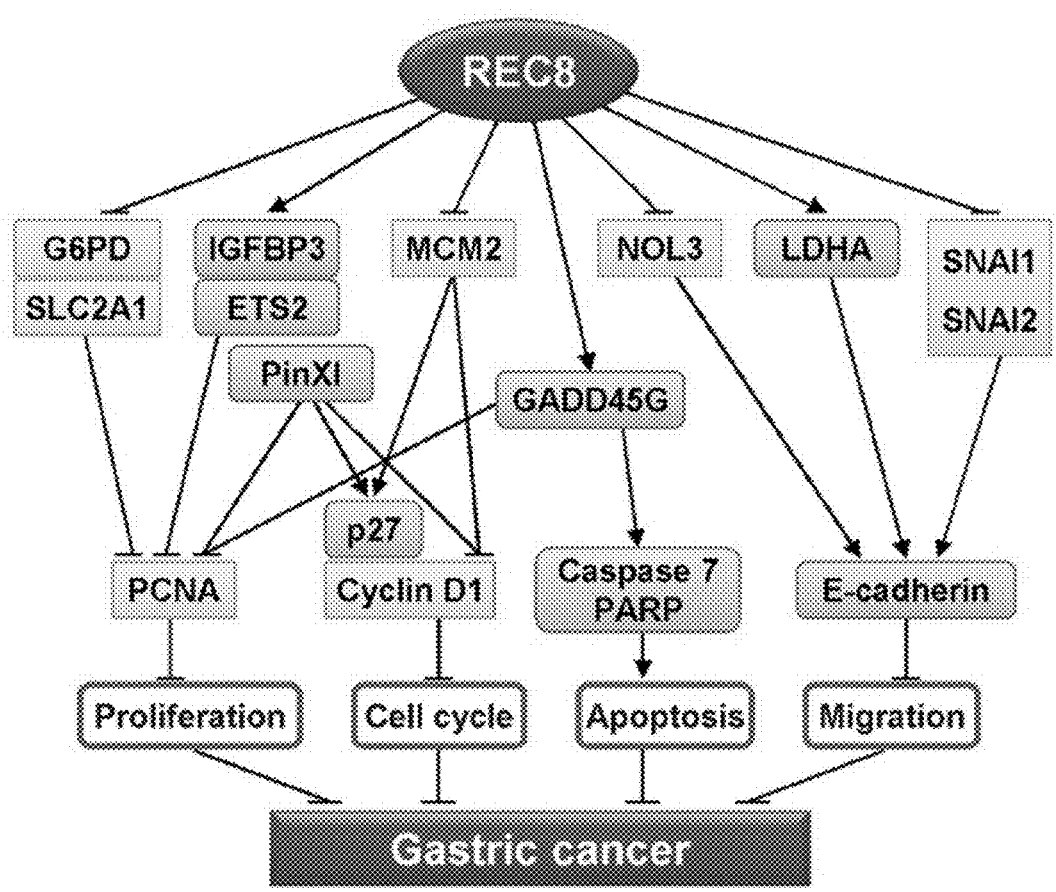

Some important effectors of proliferation, cell cycle and migration were also examined by western blot. Results showed that REC8 suppressed the G1-S transition promoter (cyclin and the proliferation marker (PCNA), and it induced the G1 gatekeeper (p27), supporting the effect of REC8 on blocking cell cycle progression at the G1-S checkpoint. Consistent with increased apoptosis and reduced cell migration ability by REC8, up-regulation of pro-apoptotic regulators (cleaved-caspase 7 and cleaved-PARP) and the cell-to-cell adhesion gene (E-cadherin) were also detected (FIG. 7B). The correlations between REC8 and its downstream targets, as well as their association with the inhibition of gastric cancer growth, were shown in FIG. 7C. These results revealed the molecular mechanism by which REC8 played a tumor suppressive role in gastric cancer.

Discussion

In this study, it was confirmed that REC8 was down-regulated in gastric cancer, especially in the EBV-associated subtype, via promoter methylation. Clinical implications of REC8 promoter methylation and functional importance of REC8 as a novel tumor suppressor in gastric cancer were also elucidated.

EBV-associated host gene methylation in gastric cancer was previously investigated; REC8 was identified to be one of the hypermethylated genes in EBV-positive gastric cancer cell line (AGS-EBV) compared to EBV-negative AGS cell line. It was further validated that the methylation level of REC8 promoter is significantly higher in EBV-associated gastric tumors as compared to EBV-negative gastric tumors.[7] Thus in this study, REC8 was further compared between EBV-associated gastric cancer and EBV-negative gastric cancer. However, it was found that REC8 expression was absent or down-regulated in 9 of 13 gastric cancer cell lines, including both EBV-positive and EBV-negative cells. Inactivation of REC8 is directly associated with promoter methylation as shown by BGS and expressional restoration by demethylation agent treatment. Importantly, data from 223 gastric cancer samples of the TCGA study showed a significant negative correlation between methylation of the REC8 promoter and REC8 mRNA expression. Silenced protein expression and significantly higher level of promoter methylation was also detected in gastric tumor samples as compared with normal gastric mucosa tissues in Chinese patients. These results confirm direct down-regulation of REC8 by promoter methylation in gastric cancer. Notably, methylation level was significantly higher in 13 EBV-positive gastric tumors than in 18 EBV-negative gastric tumors from Chinese patients. Linear regression analysis in these samples further showed that EBV infection status was the only factor associated with a higher REC8 methylation level (Table 1).

The sample size of Chinese patients with gastric tumors for methylation level quantification was further enlarged to investigate the clinical implication of REC8 promoter methylation. In a cohort of 191 gastric cancers, regardless of EBV status, 94.2% (180 of 191) cases showed a methylation level over 33.4%; the best cutoff value to discriminate gastric tumor from normal mucosa (FIG. 3A). Using 33.4% as a cut point will group 94.2% (180 of 191) gastric cancer cases as 'methylated' and the other 5.8% (11 of 191) cases as 'unmethylated'. It would be meaningless to analyze the consequences of methylation of the REC8 promoter by comparing the 180 methylated cases with only 11 unmethylated cases. Therefore, these cases were classified into groups of 'high-methylation' and 'low-methylation' using 55% cutoff value by survival significance analysis using the tool, Cutoff Finder. While there was no correlation between the REC8 low/high-methylation and clinicopathological features, such as age, gender, H. pylori infection status, Lauren type, differentiation, and TNM stage, multivariate Cox regression analysis revealed high-methylation of REC8 promoter to be an independent predictor of poor survival in gastric cancer patients (Table 3).

The methylation level of the REC8 promoter was quantitated by direct Sanger sequencing of the PCR amplicons. As reviewed by Mikeska et al.,[18] when heterogeneous methylation comprising multiple alleles with varied DNA methylation patterns (epialleles) is present, direct bisulfite sequencing of PCR products could not provide detailed information to characterize the heterogeneity of a sample. The method assessed only the average methylation level of each CpG site within the PCR target region. The methylation status of the REC8 promoter, either heterogeneously methylated or comprising of a simple mixture of fully methylated and unmethylated alleles in gastric tumors, may not influence its value as a cancer biomarker. Poor peak quality with an increasing nucleotide number may happen when direct bisulfite sequencing is applied, especially for partially methylated samples.[18] More convenient methods for methylation quantitation, such as bisulfite pyrosequencing and digital PCR approaches, should be developed to better quantitate the promoter methylation of REC8 for clinical implementation.

Both gain- and loss-of-function experiments were then performed to investigate the role of REC8 in gastric cancer. Expression of REC8 exhibited marked growth-suppressing effect in both EBV-positive and EBV-negative gastric cancer cells, while knock-down of REC8 significantly induced cell growth by increasing cell viability and clonogenicity. The growth inhibitory effect of REC8 was further revealed to be related to the induction of apoptosis and inhibition of cell cycle progression by flow cytometry. The increased apoptosis induced by REC8 was further revealed by up-regulation of the activated caspase-7 to stimulate the proteolytic cleavage of PARP for apoptosis initiation. Cell cycle analysis revealed that REC8 expression inhibited G1-S transition, with a significant increase of cells in G1 phase and decrease in S phase. The inhibition of cell cycle progression by REC8 was further demonstrated by the down-regulated G1-S transition promoter (cyclin D1) and proliferation marker (PCNA) and the up-regulated G1 gatekeeper (p27). Moreover, REC8 was observed to inhibit cell migration by induction of the cell-cell adhesion molecule, E-cadherin. With the similar functional results found in EBV-positive and -negative cell lines, it is inferred that the silencing of REC8 by promoter methylation plays a similar role during gastric carcinogenesis in both EBV-positive and EBV-negative subtypes. Although EBV infection is one of the multiple factors contributing to REC8 promoter methylation, the significantly higher methylation level in EBV-associated gastric cancer as compared to EBV-negative gastric cancers, might lead to new insights into guiding the management of EBV-associated gastric cancer.

Efforts were made to further elucidate the molecular basis of the tumor suppressive effect of REC8 using cancer pathway cDNA microarray. It was shown that REC8 exerted its anti-growth effect by inhibiting the cell proliferation regulators (G6PD and SLC2A1) and apoptosis inhibitor (NOL3), while inducing expression of the apoptosis regulator (GADD45G) and tumor suppressors (PinX1, IGFBP3 and ETS2). High levels of the glucose-6-phosphate dehydrogenase (G6PD) correlate with breast cancer metastasis and contribute to in vivo tumor growth.[19] The glucose transporter, SLC2A1, plays a vital role in glucose supply to cells, and PKA and cAMP stimulate cell proliferation by elevating SLC2A1 expression.[20] The nucleolar protein, NOL3, is an endogenous inhibitor of apoptosis and promotes breast tumorigenesis and metastasis.[21] GADD45G inhibits cell growth and induces apoptosis.[22] PIN2/TRF1-interacting telomerase inhibitor 1 (PinX1) acts as a putative tumor suppressor by inhibiting telomerase.[23] Insulin-like growth factor-binding protein 3 (IGFBP3) impedes aggressive growth of pediatric liver cancer.[24] A tumor suppressor role has also been revealed for ETS2 in human non-small cell lung cancer.[25] Moreover, REC8 caused cell cycle arrest at G1-S transition by inhibiting MCM2 and increasing PinX1. MCM2 is a cell cycle regulator promoting cell transmission from G1 to S phase.[26] PinX1 has also been reported to inhibit G1-S transition and cell proliferation through the p16/cyclin D1 pathway in urothelial carcinoma of the bladder.[23]

The anti-migration function of REC8 may be mediated by inhibiting EMT promoters SNAI1 and SNAI2, which are involved in generating de-differentiated cells, and inducing the migration inhibitor Lactate dehydrogenase A (LDHA). SNAIL and SNAI2 are zinc finger transcriptional repressors that have been reported to contribute to the aggressiveness of prostate cancer[27] and invasiveness of malignant breast cancer,[28] respectively. LDHA functions in anaerobic glycolysis. Attenuation of LDHA expression in cancer cells affects cytoskeletal structure and cell migration.[29] Therefore, REC8 plays a tumor suppressive function by modulating the expression of important genes involved in multiple cellular processes, including proliferation, cell cycle, apoptosis, migration and differentiation.

In conclusion, the present inventors have identified that REC8 is a novel gene that is silenced by promoter hypermethylation in gastric cancer, especially the EBV-subtype. REC8 plays an important tumor suppressive role in gastric carcinogenesis by modulating the important effectors involved in the regulation of cell proliferation, apoptosis, cell cycle and migration. More importantly, a high level of promoter methylation of REC8 is an independent risk factor for poor prognosis in gastric cancer patients. Epigenetic silencing of REC8 may contribute to the pathogenesis of gastric cancer.

Materials and Methods

Cancer Cell Lines and Culture Condition

Gastric cancer cell lines (AGS, NCI-N87, KatoIII) were obtained from American Type Culture Collection (ATCC, Manassas, Va.). AGS-EBV, a EBV infected gastric cancer cell line,[30] was a gift from Dr. Shannon C. Kenney (Department of Oncology and Medicine, McArdle Laboratory for Cancer Research at the University of Wisconsin, Madison, Wis.). MKN28, MKN45, SNU16, SNU620, SNU638 and SNU719 cell lines were obtained from the Korean Cell Line Bank (Seoul, Korea). YCCEL1 was a gift from Sun Young Rha at Yonsei Cancer Center, Yonsei University College of Medicine, Seoul, Korea. BGC823, MGC803 and the immortalized normal human gastric epithelial cell line GES-1 were gifts from Oncology Hospital, Beijing University. Cells were cultured in RPMI 1640, DMEM, or McCoy medium (Gibco BRL, Rockville, Md.) supplemented with 10% fetal bovine serum (Gibco BRL).

Human Samples

Gastric cancer tissue samples were collected in the First Affiliated Hospital of Sun Yat-sen University, Guangzhou, from 1999-2006 and Prince of Wales Hospital, The Chinese University of Hong Kong, from 2005-2013. The presence of EBV was determined by detection of EBER carried out as previously reported by the inventors' group.[31] *H. pylori* status was assessed by examining the gram-negative curved bacilli on histology.[4] All patients gave informed consent for participation in this study. This study was approved by both the Clinical Research Ethics Committee of Sun Yat-sen University and the ethics committee of the Chinese University of Hong Kong.

BGS

BGS and COBRA were performed to evaluate methylation status. PCR amplification was performed with 2 µL bisulfite converted DNA. Direct Sanger sequencing of the PCR products was used to evaluate methylation levels at multiple CpG sites. The proportion of methylation was calculated as the peak ratio of cytosine to the sum of cytosine and thymine at each site. Primers used are listed in Table 5 and also published previously.[7]

Demethylation with 5-Aza-2'-Deoxycytidine Agent Treatment

Gastric cancer cells were treated with 2 uM DNA demethylation agent 5-Aza-2'-deoxycytidine (5-Aza) (Sigma-Aldrich, St Louis, Mo.) for 5 days and medium was refreshed every day.

Immunohistochemistry

Paired primary tumor and adjacent non-tumor samples were obtained from 12 gastric cancer patients after surgical resection. Tissue types (tumor or normal) were assessed by histological staining. The remaining tissue specimens were fixed in 10% formalin and embedded in paraffin. Immunohistochemistry was performed on five-micrometer paraffin sections using anti-REC8 antibodies (Abcam, Cambridge, UK) as previously described.[5, 32] REC8 staining in the nucleus and cytoplasm was evaluated by scanning the whole section and counting more than 1,000 representative cells.

RNA Extraction, RT-PCR and qPCR

Total RNA was extracted from cell pellets or tissues using Qiazol® reagent (Qiagen, Valencia, Calif.), and cDNA was synthesized using Transcriptor Reverse Transcriptase (Roche, Indianapolis, Ind.). RT-PCR was performed using the GoTaq® DNA polymerase (Promega). qPCR was performed using SYBR Green master mixture on HT7900 system (Applied Biosystems, Foster City, Calif.). Primers used are listed in Table 5 and also published previously.[7]

Correlation Between REC8 Promoter Methylation and mRNA Expression

Methylation (HM450) and mRNA expression (RNA Seq V2 RSEM) data from TCGA Stomach Adenocarcinoma (Provisional) study were retrieved at cBioPortal (website: cbioportal.org/public-portal/index.do).[33, 34] In total, 223 TCGA gastric samples (follow-up time=1.18 [0.46-8.92] months, median [interquartile range]) with both methylation and mRNA expression data were included in this study. Linear regression was performed on Log 10 mRNA levels and methylation levels.

Western Blot

Total protein was extracted and protein concentration was then measured by the DC protein assay method of Bradford (Bio-Rad, Hercules, Calif.). Proteins were separated on sodium dodecyl sulfate-polyacrylamide gel electrophoresis (SDS-PAGE) and transferred onto nitrocellulose membranes (GE Healthcare, Piscataway, N.J.). Blots were immunostained with primary antibodies overnight, and then with secondary antibody at room temperature for 1 hour. Proteins of interest were visualized using ECL Plus Western blotting Detection Reagents (GE Healthcare). Antibodies against GAPDH (sc-25778) and E-cadherin (sc-21791) were purchased from Santa Cruz Biotechnology (Santa Cruz, Calif.). Antibodies against Cyclin D1 (#2978), p27 (#3686), Cleaved Caspase-7 (#9491) and Cleaved PARD (#5625) were purchased from Cell Signaling Technology (Danvers, Mass.). Antibody against PCNA (ab29) was purchased from Abcam.

Construction of Vector and Ectopic Expression of REC8

Full length of the open reading frame of human REC8 was generated by reverse-transcription PCR. The PCR products were confirmed by direct DNA sequencing and cloned into a mammalian expression vector, pcDNA3.1 (Invitrogen, Carlsbad, Calif.). The sequence of the construct was further confirmed by sequencing. The resulting expression vectors were transfected into cells with low expression of REC8 (AGS-EBV and BGC823) using Lipofectamine™ 2000 (Invitrogen). Stably transfected cells were established under selection with neomycin (G418) (Invitrogen). Empty vectors were used as control for transfection.

Knock-Down of REC8

A set of vectors carrying shRNAs against REC8 was purchased from Origene (Rockville, Md.). The REC8-expressing cell lines GES-1 and AGS were transfected with vectors carrying scrambled sequence (sh-scrambled) as negative control. Knock-down efficiency was evaluated 48 hours after transfection by western blot. Puromycin (Invitrogen) was used to establish stable knock-down cells for colony formation and cell viability assays.

Cell Viability Assay

Cell viability was assessed by the MTT assay (Promega, Madison, Mich.).[5] The experiments were performed three times independently.

Colony Formation Assay

Colony formation was performed as described previous e experiments were performed three times independently.

Cell Cycle Analysis

AGS-EBV and BGC823 cells transfected with REC8 expression vector or empty vector were fixed in 70% ethanol-PBS for 24 hours and labeled with 50 µg/ml propidium iodide (BD Biosciences, Franklin Lakes, N.J.). The cells were sorted by FACSCalibur™ Flow Cytometer (BD Biosciences) and cell cycle distributions were analysed using the ModFitLT™ software (BD Biosciences).

Apoptosis

Cell apoptosis was determined by staining cells with Annexin V and 7-amino-actinomycin (7-AAD) (BD Biosciences) with subsequent flow cytometry analysis. Cell populations were counted as viable (Annexin V-negative, 7-AAD-negative), early apoptotic (Annexin V-positive, 7-AAD-negative), late apoptotic (Annexin V-positive, 7-AAD-positive), or necrotic (Annexin V-negative, 7-AAD-positive).

Cell Migration Assay

Cell migration was evaluated using wound-healing assay for three independent experiments as previously described.[5]

In Vivo Tumorigenicity

BGC823 cells ($1 \times 10^7$ cells in 0.1 ml PBS) stably transfected with REC8 expression vector or empty vector were injected subcutaneously into the dorsal flank of 4-week-old male Balb/c nude mice (n=5/group). Tumor diameter was measured every two days for two weeks. Animal experimental procedures were approved by the Animal Ethics Committee of the Chinese University of Hong Kong.

Human Cancer Pathway Finder RT2 Profiler PCR Array

Gene expression profiles of gastric cancer cell lines AGS-EBV transiently transfected with REC8 or control plasmid were analysed by the Human Cancer Pathway-Finder RT2 Profiler™ PCR Array (Qiagen), which contained 84 well-characterised genes with representative roles in tumorigenesis.[12]

Statistical Analysis

The results were expressed as mean±standard deviation (SD) or median (IQR). Mann-Whitney U test was performed to compare the variables of the two sample groups. ROC curve was used to estimate the cutoff value of the methylation percentage. Methylation cutoff value was analyzed by survival significance analysis using the tool Cutoff Finder (website: molpath.charite.de/cutoff/).[17] The difference in tumor growth rate between the two groups of nude mice was determined by repeated-measures analysis of variance. All statistical tests were performed using Graphpad Prism 5.0 (Graphpad Software Inc., San Diego, Calif.) or the SPSS program (version 17.0; SPSS, Chicago, Ill.). Value of P<0.05 was taken as statistical significance.

TABLE 1

Linear regression analysis of potential predictor for REC8 methylation in gastric cancer patients (with EBV status)

| Variable | β | p-value |
|---|---|---|
| Age | 0.404 | 0.215 |
| Gender | | 0.706 |
| Male | 3.316 | |
| Female | 1 | |
| *H. pylori* | | 0.493 |
| Negative | −5.394 | |
| Positive | 1 | |
| Lauren | | 0.057 |
| Non-intestinal | 19.292 | |
| Intestinal | 1 | |
| Differentiation | | 0.342 |
| Moderate or High | −7.592 | |
| Low | 1 | |
| TNM stage | | |
| I | −5.354 | 0.783 |
| II* | NA | NA |
| III | −8.660 | 0.709 |
| IV | 1 | |
| EBER | | 0.001 |
| positive | 23.727 | |
| negative | 1.00 | |

Linear regression analysis was performed on 31 gastric cancer patients, including 13 EBV-positive and 18 EBV-negative.
*no case of TNM stage II was included Linear regression analysis was performed on 31 gastric cancer patients, including 13 EBV-positive and 18 EBV-negative. *no case of TNM stage II was included.

TABLE 2

Distribution of patient characteristics by methylation status (all gastric cancer)

| Variable | High Methylation (n = 56) | % | Low methylation (n = 135) | % | p-value |
|---|---|---|---|---|---|
| Mean age, y ± SD | 55.89 ± 13.218 | | 56.82 ± 12.799 | | 0.655 |
| Gender | | | | | 0.847 |
| M | 36 | 28.3 | 21 | 71.7 | |
| F | 19 | 29.7 | 45 | 70.3 | |
| *H. pylori* | | | | | 0.400 |
| Positive | 34 | 32.1 | 72 | 67.9 | |
| Negative | 21 | 25.0 | 63 | 75.0 | |
| TNM | | | | | 0.149 |
| I | 11 | 35.5 | 20 | 64.5 | |
| II | 5 | 20.8 | 19 | 79.2 | |
| III | 19 | 22.1 | 67 | 77.9 | |
| IV | 11 | 36.7 | 19 | 63.3 | |
| Lauren | | | | | 0.094 |
| Intestinal | 43 | 26.2 | 121 | 73.8 | |
| Non-intestinal | 12 | 46.2 | 14 | 53.8 | |
| Differentiation | | | | | 0.714 |
| Low | 33 | 31.1 | 73 | 68.9 | |
| Moderate or High | 17 | 25.4 | 50 | 74.6 | |

TABLE 3

Univariate and Multivariate Cox regression analyses of potential poor prognostic factors for gastric cancer patients (all and EBV-negative gastric cancers)

| | All 191 cases | | | | 178 EBV-negative cases | | | |
|---|---|---|---|---|---|---|---|---|
| | Univariate | | Multivariate | | Univariate | | Multivariate | |
| Variable | HR | p-value | HR | p-value | HR | p-value | HR | p-value |
| Age | 0.994 | 0.518 | | | 0.993 | 0.445 | | |
| Gender | | 0.954 | | | | 0.729 | | |
| Male | 1.013 | | | | 1.086 | | | |
| Female | 1 | | | | 1 | | | |
| *H. pylori* | | 0.501 | | | | 0.733 | | |
| Positive | 1.573 | | | | 1.085 | | | |
| Negative | 1 | | | | 1 | | | |
| Lauren | | 0.939 | | | | 0.102 | | |
| Intestinal | 0.004 | | | | 0.616 | | | |
| Non-intestinal | 1 | | | | 1 | | | |
| Differentiation | | 0.137 | | | | 0.994 | | |
| Low | 1.366 | | | | 1.002 | | | |
| Moderate/High | 1 | | | | 1 | | | |
| TNM stage | | | | | | | | |
| I | 0.217 | <0.001 | 0.228 | <0.001 | 0.199 | <0.001 | 0.206 | <0.001 |
| II | 0.084 | <0.001 | 0.087 | <0.001 | 0.090 | <0.001 | 0.076 | <0.001 |
| III | 0.280 | <0.001 | 0.301 | <0.001 | 0.291 | <0.001 | 0.290 | <0.001 |
| IV | 1 | | 1 | | 1 | | 1 | |

TABLE 3-continued

Univariate and Multivariate Cox regression analyses of potential poor prognostic factors for gastric cancer patients (all and EBV-negative gastric cancers)

| | All 191 cases | | | | 178 EBV-negative cases | | | |
|---|---|---|---|---|---|---|---|---|
| | Univariate | | Multivariate | | Univariate | | Multivariate | |
| Variable | HR | p-value | HR | p-value | HR | p-value | HR | p-value |
| REC8 methylation | | 0.030 | | 0.042 | | 0.014 | | 0.029 |
| Yes | 1.642 | | 1.678 | | 1.829 | | 1.860 | |
| No | 1 | | 1 | | 1 | | 1 | |

Example 2: REC8 as a Prognostic and Non-Invasive Diagnostic Marker

Introduction

In a previous study, a novel tumor suppressor gene REC8 regulated by promoter methylation in gastric cancer was identified (35). REC8 is frequently methylated in gastric tumor tissues, and a high-methylation level is associated with shortened survival of gastric cancer patients. As a new biomarker for prognostic prediction in gastric cancer, detection of REC8 promoter methylation has valuable clinical application value in guiding therapy. The most widely used method for target quantification of DNA methylation is the conventional bisulfite genomic sequencing (BGS) method, which was also applied in our previous REC8 study. However, BGS method is cumbersome (bisulfite treatment, PCR, Sanger sequencing and analysis of sequencing chromatograms) and requires high quality DNA, and thus not applicable directly in clinical settings.

In this study, a sensitive and convenient method was developed for quantification of REC8 methylation, with the target region well selected by analyzing The Cancer Genome Atlas (TCGA) data and experimental procedures involving bisulfite treatment and qPCR. The prognostic prediction potential was well validated by the new method. Most importantly, the new method is sensitive enough to detect the methylated REC8 in plasma samples. It was further shown that detection of methylated REC8 promoter in plasma samples can serve as a non-invasive method for the diagnosis of gastric cancer. The new method is sensitive and convenient enough for direct clinical implementation for both diagnosis/screening and prognosis.

Materials and Methods

Human Tissue and Plasma Samples

Gastric cancer tissue samples were collected in the First Affiliated Hospital of Sun Yat-sen University, Guangzhou from 1999-2006 and Prince of Wales Hospital, The Chinese University of Hong Kong from 2005-2013. Blood samples collected in EDTA tubes were centrifuged at 3,000 rpm (1,600 g) for 15 mins at 4° C. Supernatant plasma was transferred into 1.5 mL tubes and centrifuged at 13,000 rpm (16,000 g) for 15 mins at 4° C. Then plasma was transferred into 2 mL vials and stored at −80° C. till DNA extraction. All patients gave informed consent for participation in this study. This study was approved by both the Clinical Research Ethics Committee of Sun Yat-sen University and the ethics committee of the Chinese University of Hong Kong.

DNA Extraction and Bisulfite Conversion

Genomic DNA from primary gastric cancer tissues was extracted using QIAamp DNA Mini Kit (Qiagen, Hilden, Germany). Cell-free DNA from plasma samples (400 µL) was extracted using QIAamp DNA blood Mini Kit (Qiagen). DNA samples (500 ng from tissue samples or 20 µL from plasma samples) were subjected to bisulfite modification using EZ DNA Methylation-Gold™ Kit (Zymo Research Corp, Irvine, Calif.) following the manufacturer's instructions.

Bisulfite Genomic Sequencing (BGS)

BGS were performed to evaluate methylation status. PCR amplification was performed with 2 µL bisulfite converted DNA. Primers for BGS were designed using MethPrimer (website: urogene.org/methprimer/index1.html). Nucleotide sequences of the BGS primers are as follows: forward-GTAAAATTTTTATGATTGGTTTGTTG (SEQ ID NO:9); reverse-CCCCTAAACCTTACACTAACT (SEQ ID NO:10). Direct Sanger sequencing of the PCR products was used to evaluate methylation levels at multiple CpG sites. The proportion of methylation was calculated as the peak ratio of cytosine to the sum of cytosine and thymine at each site.

Design of Primers and Probes

Primer and probe sequences were designed manually on the basis of a bisulfite converted DNA template, with the target sequence being most densely methylated region covered by cg06351481 of Illumina Infinium Human Methylation450 (HM450K bead array). Primer and probe sequences were tested using the tool PrimerExpress v3.0 (Applied Biosystems, Foster City, Calif.) for determination of Tm, GC content and possible secondary structures. Unlike conventional BGS primers, a degenerate site was included in the forward primer to cover both methylated and unmethylated alleles; the degenerate site was not close to 3' ends of primers. Two probes were designed to specifically target the methylated and unmethylated alleles specifically. The primer-probe sets specifically detect our targets and not any other known sequences, as confirmed by Blast search. Each probe carried a 5' reporter dye FAM (6-carboxyfluorescein) or VIC (4,7,2'-trichloro-7'-phenyl-6-carboxyfluorescein) and a 3' minor groove binder. Primers and hydrolysis probes were synthesized by Invitrogen (Carlsbad, Calif.). Nucleotide sequences of the primers and probes are listed in the table below. PCR amplification specificity was confirmed by direct Sanger sequencing of the PCR products.

Nucleotide Sequences Used in this Study

| Name | Sequence (5'->3') |
|---|---|
| Forward | GAGGAAATTTTTAATTAYGTGTTGGT (SEQ ID NO: 11) |
| Reverse | TTTAAAAATTCCCAACCTTACCC (SEQ ID NO: 12) |

-continued

| Name | Sequence (5'->3') |
|---|---|
| M-probe | TGTGATTCGCGTTTATTTTTAATAAT (SEQ ID NO: 13) |
| U-probe | TGTGATTTGTGTTTATTTTTAATAATGTTAGTAT (SEQ ID NO: 14) |

Quantitative PCR (qPCR)

qPCR amplifications were performed in a 20 μL reaction system of AceQ qPCR Probe Master Mix (Vazyme, Nanjing, China) containing 0.3 μM of each primer, 0.1 μM of the methylated probe and 0.2 μM of unmethylated probe in MicroAmp fast optical 96-well reaction plates (Applied Biosystems) with adhesive sealing. Thermal cycler parameters, of an ABI QuantStudio sequence detection system, were 95° C. 10 min and (95° C. 15 s, 55° C. 30 s, 72° C. 30 s)×45 cycles. A positive/reference control and two negative controls (an unconverted DNA and H$_2$O) were included within every experiment. Measurements were performed in triplicates for each sample. qPCR data was analyzed using the Sequence Detection Software (Applied Biosystems) with manual settings of Threshold=0.015 and auto baseline for all samples. Experiments were disqualified if Cq value was <42 for any negative control or detection of positive control failed.

Scoring Algorithms

Two scoring algorithms were employed to assess methylation levels: 1) dQ-score=power(2, −CqM)/power(2, −CqU), and 2) rQ-score=power(2, −CqM)/[power(2, −CqM)+power(2, −CqU)]. The dQ-score could range from 0 to ∞, while the rQ-score ranges from 0 to 1.

Statistical Analysis

Values were all expressed as mean±SD or median (interquartile range [IQR]) as appropriate. The differences in specific bacterial abundance were determined by Wilcoxon signed-rank test or Mann-Whitney U test. The tool Cutoff Finder (website: molpath.charite.de/cutoff/) was used to determine the best cutoff value and to conduct survival significance analysis (17). Receiver Operating Characteristic (ROC) curve was used to evaluate the diagnostic value of methylated REC8 in distinguishing gastric cancer. Pairwise comparison of areas under ROC was performed using a nonparametric approach (36). All tests were done by Graphpad Prism 6.0 (Graphpad Software Inc., San Diego, Calif.) or SPSS software v17.0 (SPSS, Chicago, Ill.). P<0.05 was taken as statistical significance.

Results

Selection of CpG Sites for Targeted Quantification

Figure 8A:
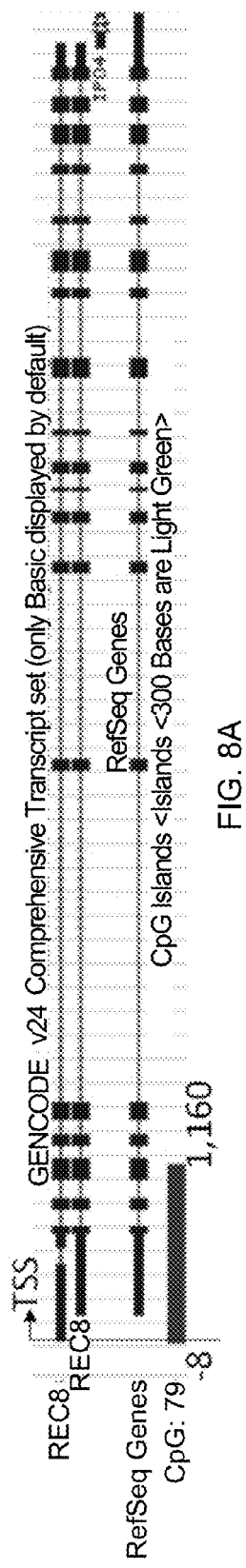
FIGS. 8A-8C.
Figure 8B:
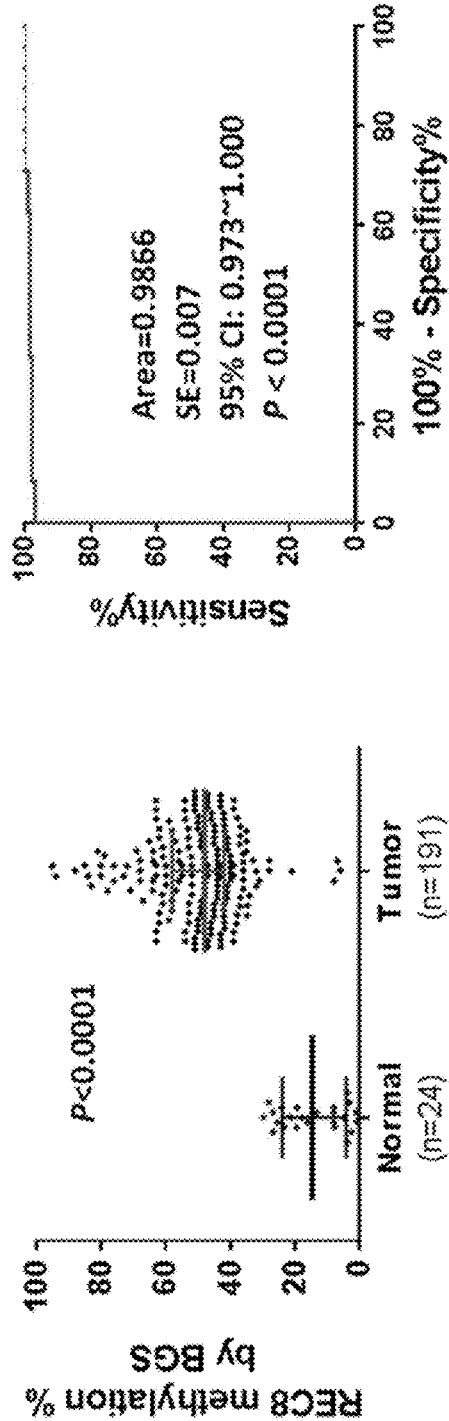

A typical CpG island is present at the promoter region of REC8 (−8∼1,160 by referring to the transcription start site) (FIG. 8A). According to previous quantification by conventional BGS method targeting the CpG island on tissue samples, the promoter methylation level of REC8 was significantly higher in gastric tumor tissues than in non-tumor stomach tissues (P<0.0001) (FIG. 8B). The level is so high that it could well discriminate tumors from non-tumor tissues with an area under ROC curve of 0.9866; this infers that detection of methylated REC8 in plasma samples may serve as a non-invasive diagnostic biomarkers for gastric cancer. In order to select the best target site for rapid quantification of the methylation level, the Illumina Infinium Human Methylation450 (HM450K) array data on the CpG island of REC8 were checked in the 398 gastric tumor samples tested in The Cancer Genome Atlas (TCGA) study.

Figure 8C:
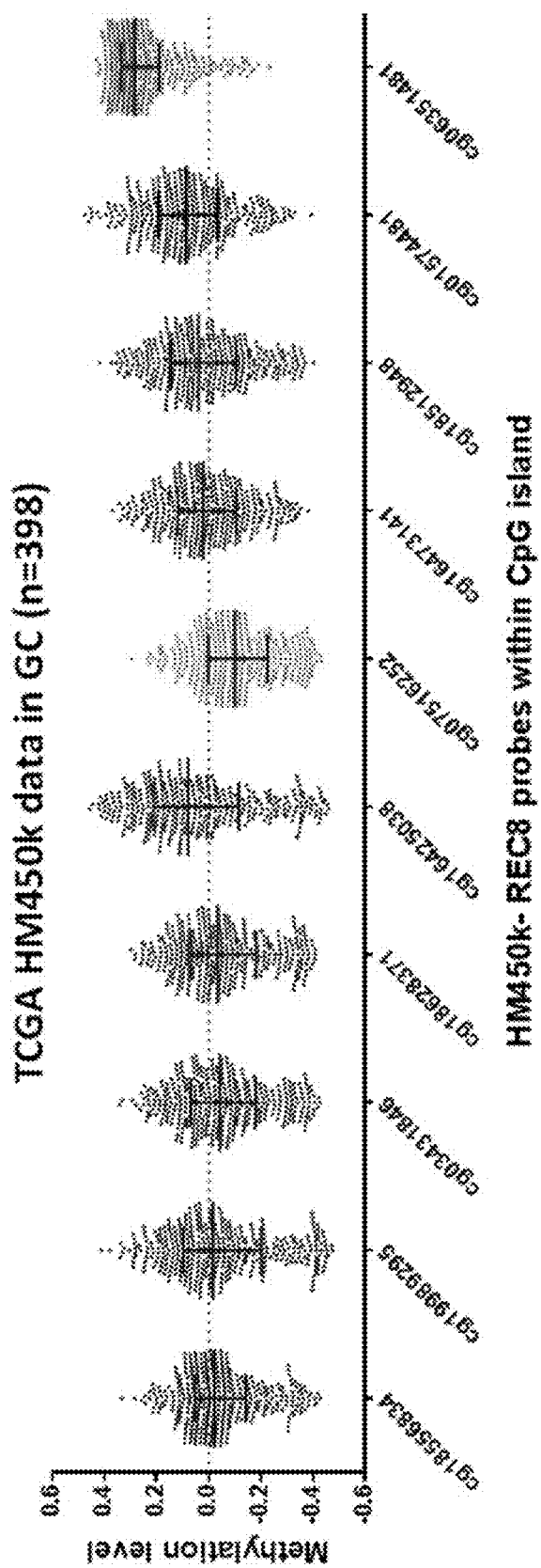

It was found that the site covered by probe cg06351481 was methylated at the highest level compared with other sites (FIG. 8C). Therefore, the region around cg06351481 was targeted for design of a probe-based qPCR assay.

Good Performance of the New qPCR Method for Quantification of REC8 Methylation

Figure 9A:
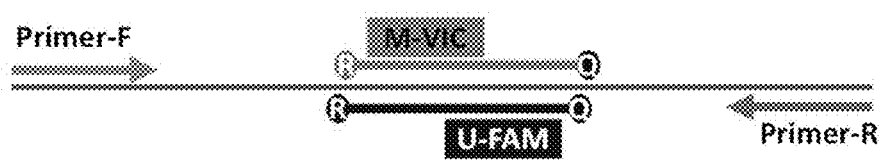
FIGS. 9A-9C. Performance of the new qPCR method for quantification of REC8 methylation.
Figure 9B:
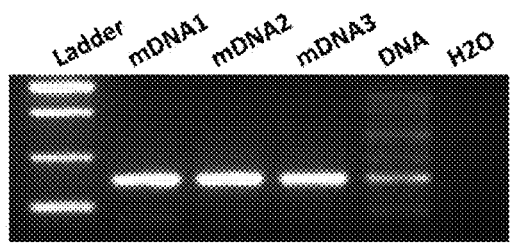
Figure 9C:
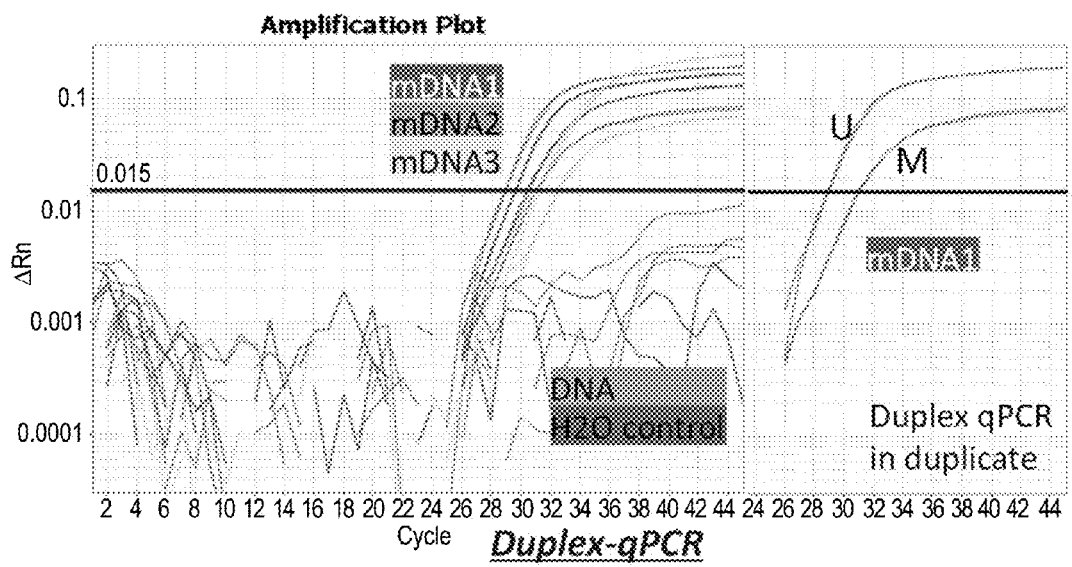

A duplex strategy was employed for primer-probe design targeting the selected CpG sites, with a pair of common primers binding no CpG regions and two probes binding the methylated and unmethylated alleles of the selected target respectively (FIG. 9A). The primer-pair amplified the target region specifically and efficiently from bisulfite modified DNA (mDNA) templates as shown by electrophoresis, with the methylated and unmethylated alleles distinguished by different fluorescent signals from two probes during qPCR detection (FIGS. 9B and C). Although non-specific amplicons could be amplified from non-bisulfite-converted DNA of high concentration (10-fold of the mDNA templates), no signal from the probes could be detected by qPCR. Therefore, the qPCR quantification would not be interfered by unconverted DNA remnants due to incomplete bisulfite treatment. Moreover, the fluorescent signals reflect the quality of mDNA templates; no or low signal would be detected from unqualified samples, while either or both signals show up earlier with more qualified mDNA templates.

Figure 10:
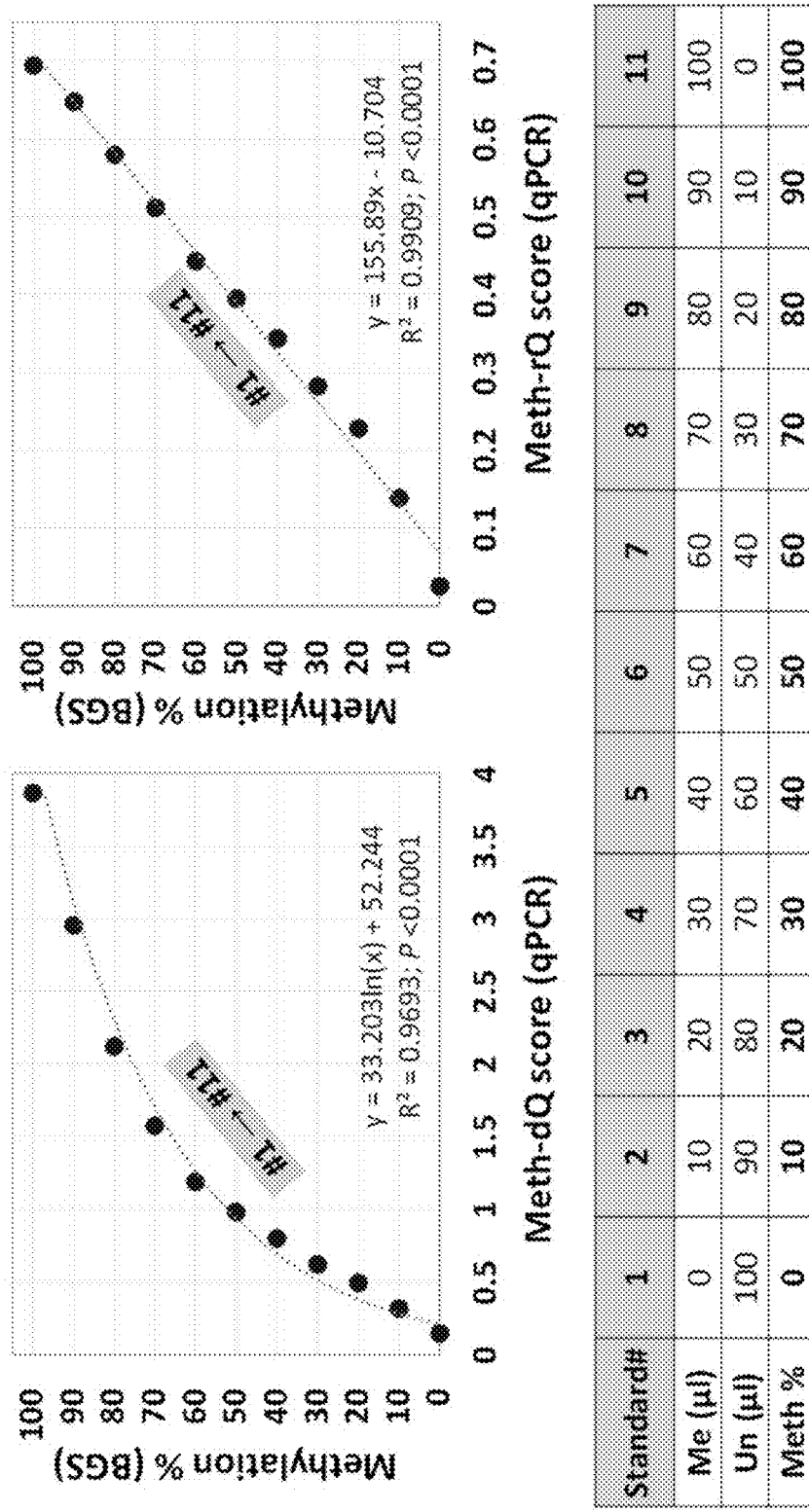
FIG. 10. Good correlation between the new qPCR method and conventional BGS method for REC8 methylation quantification. The standard templates were prepared by mixing fully methylated (Me) and fully unmethylated (Un) samples confirmed by BGS. Two methods of methylation score calculation were used, both showing positive correlation with methylation percentages, with one logarithmic and the other linear.

Good Correlation Between Methylation Quantification by qPCR Scoring and Conventional BGS To assess the correlation between qPCR quantification and conventional BGS, a series of standard templates were prepared by mixing fully methylated and fully unmethylated samples confirmed by BGS. Two algorithms were applied for methylation scoring. The dQ scores by delta Cq method show a wider distribution ranging from 0 (for unmethylated samples) to ∞, and the rQ scores represent a relative methylation level ranging from 0 to <1. The results on the standard templates showed that the dQ scores showed a natural logarithmic correlation with methylation percentages ($R^2$=0.9693; P<0.0001), while the rQ scores showed a linear correlation with methylation percentages ($R^2$=0.9909; P<0.0001) (FIG. 10). Therefore, the two qPCR scores could be directly used to represent methylation levels.

Verification of qPCR Quantification of REC8 Methylation

Figure 11A:
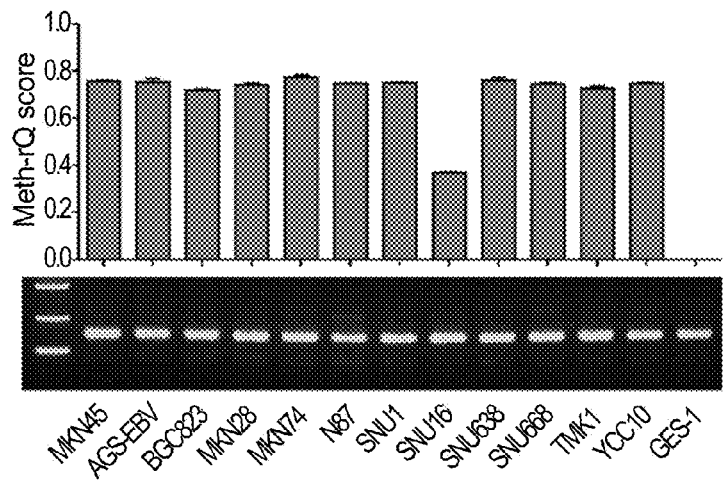
FIGS. 11A-11B.
Figure 11B:
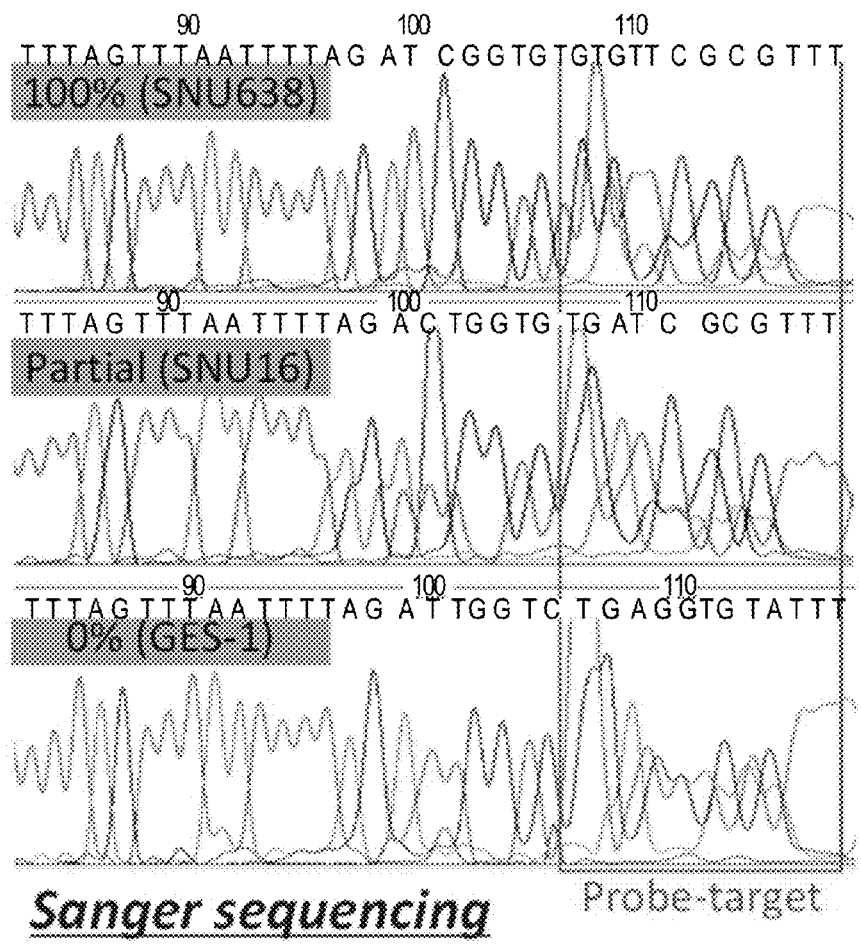

To verify the performance of the new qPCR assay on quantification of REC8 methylation, qPCR assays were performed on gastric cancer cell lines. The results showed rQ scores >0.7 for cells with fully methylated REC8 promoter, and low scores for the partially methylated SNU1 cell and the unmethylated GES-1 cell (FIG. 11A); these were confirmed by direct Sanger sequencing of the qPCR amplicons, with representative chromatograms shown in FIG. 11B.

Figure 12A:
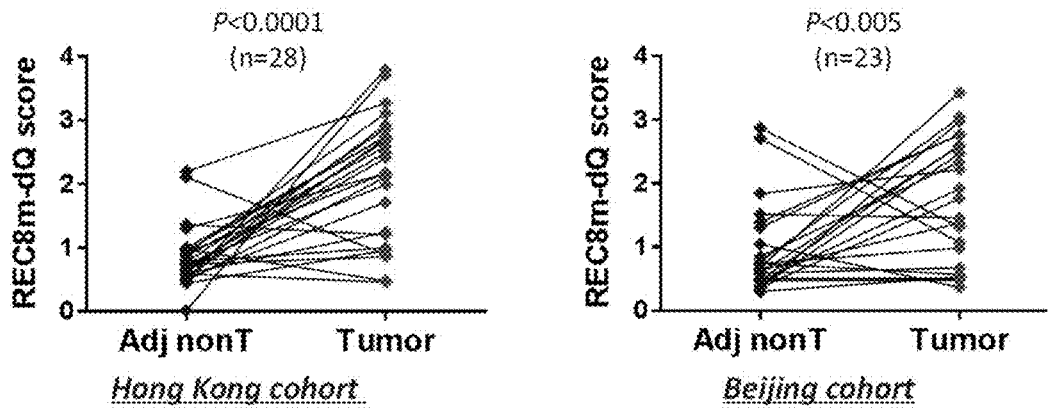
FIGS. 12A-12C.
Figure 12B:
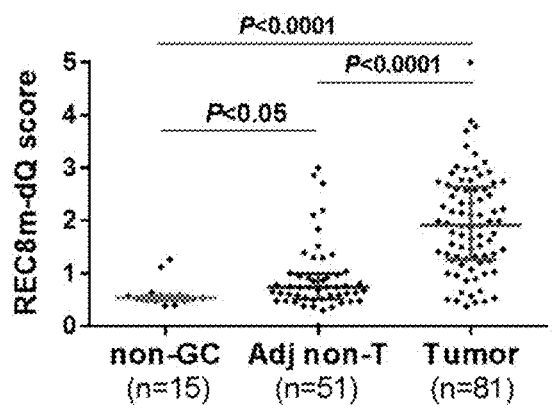
Figure 12C:
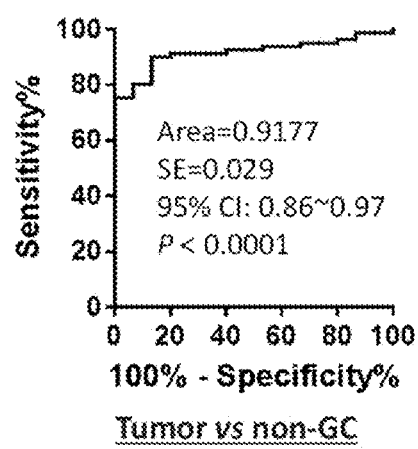

The promoter methylation level of REC8 was further assessed using the new qPCR assay in paired tumor and adjacent non-tumor samples from gastric cancer (GC) patients, as well as stomach tissues from non-GC subjects. The results showed that REC8 was methylated at significantly higher levels in gastric tumors than adjacent non-tumor tissues from two cohorts (FIG. 12A). Furthermore, REC8 promoter was methylated at significantly higher levels in both gastric tumors and adjacent non-tumor tissues as compared to normal stomach mucosas (FIG. 12B). The level REC8 promoter methylation quantitated by the new qPCR method well discriminated gastric tumor tissues from non-GC stomach, with an area under ROC curve of 0.9177 (P<0.0001; FIG. 12C). These results well verify previous findings by conventional BGS method and infer the application value of the new qPCR assay.

Figure 13:
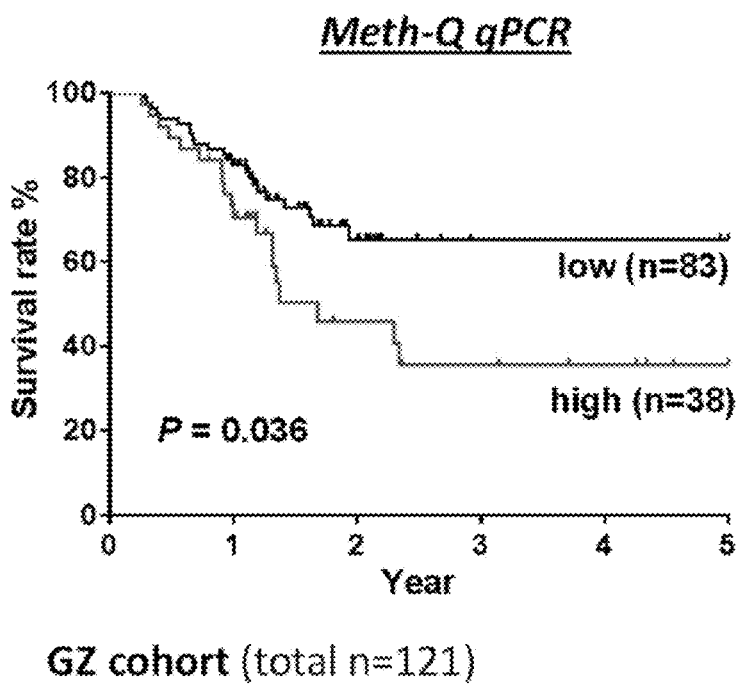
FIG. 13. Quantification of REC8 methylation in gastric tumor samples using the new qPCR method indicated that high-methylation of REC8 correlated with shortened survival in gastric cancer patients (left panel), which well verified the previous findings by conventional BGS method (right panel).
Figure 13:
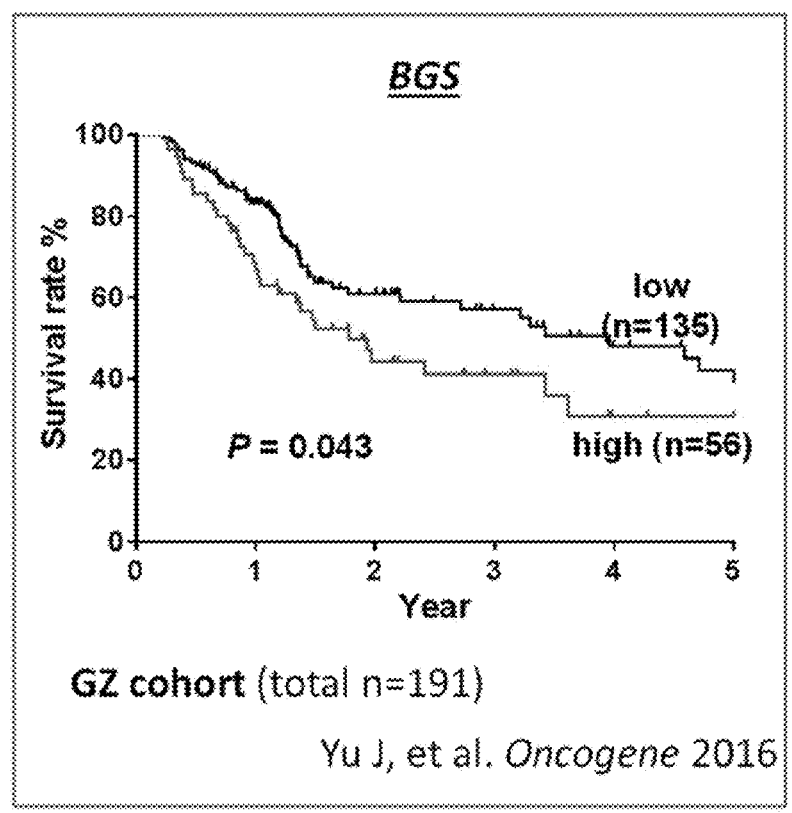

Quantification of REC8 Methylation for Prognostic Prediction Using the New qPCR Method Inventors' previous study using conventional BGS method has shown that methylated REC8 may serve as a prognostic biomarker for gastric cancer patients, with a high methylation level significantly associated with shortened survival of gastric cancer patients. To assess the application value of the new qPCR method in prognostic prediction, qPCR quantification using the new method was performed on 121 gastric tumor tissues with follow-up data. The qPCR scoring indicated that a high-methylation score of REC8 significantly correlated with shortened survival in gastric cancer patients (P=0.036; FIG. 13). This result demonstrates that the more convenient qPCR method is eligible to replace the conventional BGS method for prognostic prediction in gastric cancer.

Figure 14A:
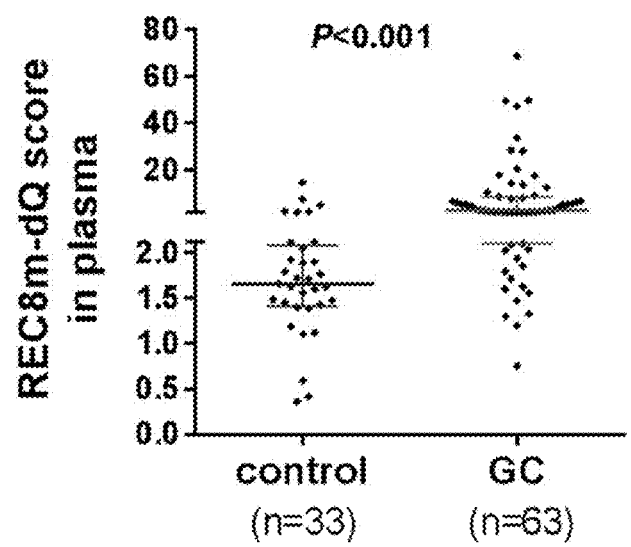
FIGS. 14A-14B. Methylated REC8 in plasma serves as a non-invasive diagnostic biomarker for gastric cancer.
Figure 14B:
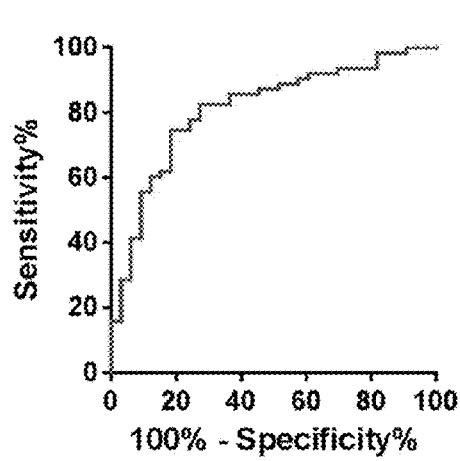

Quantification of REC8 Methylation for Non-Invasive Diagnosis Using the New qPCR Method As the methylation level of REC8 in tissue samples well discriminates gastric tumors from normal stomach, it is expected that detection of the methylated REC8 in cell-free circulating tumor DNA may serve as a new diagnostic biomarker for gastric cancer. To test this hypothesis, quantitative detection of cell-free methylated REC8 was performed in plasma samples from 63 gastric cancer patients and 33 non-cancer control subjects using the new qPCR method. The results showed a significantly higher level of REC8 methylation in plasma samples from gastric cancer patients than control subjects (FIG. 14A). The level of methylated REC8 in plasma significantly discriminated gastric cancer patients from control subjects with an area under ROC of 0.813 (P<0.001). At the best cutoff value that maximizes the sum of sensitivity and specificity, methylated REC8 diagnosed gastric cancer patients at a sensitivity of 74.6% and specificity of 81.8% (FIG. 14B). Therefore, methylated REC8 in plasma can serves as a non-invasive diagnostic biomarker for gastric cancer.

Discussion

With the newly developed qPCR-based method, quantitative detection of REC8 methylation could be applied to prognostic prediction, as well as non-invasive diagnosis, of gastric cancer. The well-designed primer-probe set targeting a well-selected region within REC8 promoter and the well-optimized protocol could be directly commercialized to be a kit for target quantitative detection of REC8 in DNA samples from different sources, such as tissue, plasma/serum, blood, stool, urine, etc.

Figure 15:
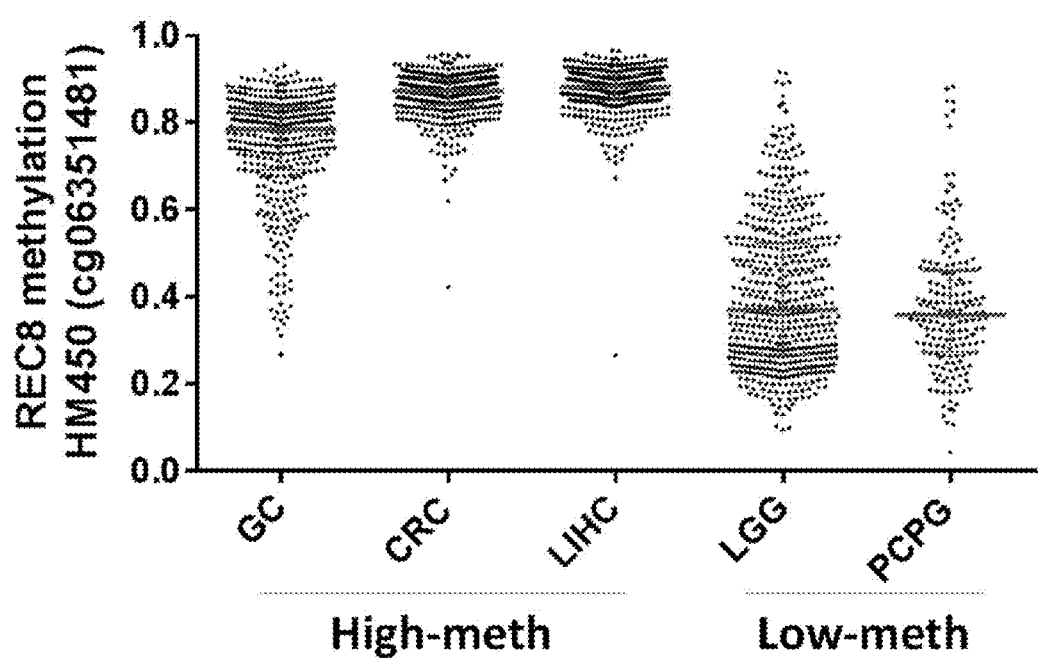
FIG. 15. HM450 methylation array data from TCGA study (downloaded from website: xena.ucsc.edu/) show that besides gastric cancer (GC), tumor tissues of some other cancer types are highly methylated at REC8 promoter, while some others are methylated at low levels. Shown are representative cancer types. CRC, colorectal cancer; LIHC, liver cancer; LGG, lower grade glioma; PCPG, Pheochromocytoma and Paraganglioma.

Further analysis on the methylation data by HM45K methylation array on other cancer types in TCGA study reveals that REC8 was not only aberrantly methylated in gastric tumor tissues but also some other cancer samples such as liver cancer and colorectal cancer (FIG. 15). Although the prognostic prediction and diagnostic application values of quantitative detection of REC8 methylation for other cancer types warrant further examination, the herein-described new method for quantitative detection of REC8 methylation has broad applications in other clinical settings.

All patents, patent applications, and other publications, including GenBank Accession Numbers, cited in this application are incorporated by reference in the entirety for all purposes.

TABLE 5

REC8 MEIOTIC RECOMBINATION PROTEIN [HOMO SAPIENS (HUMAN)]

Gene ID: 9985 mRNA sequence NM_005132.2 (SEQ ID NO: 1)
atctaatgaggagcgaggtgcggtgccccgaagcgctcgcttcccgcggtgcgatctagtcctgcagtaggcggcccggggccacacc
gcggccgcccaagccagtgcaaggcccaggggcctgacatcgctcccagcgctcgaggaccgaggcctgctgtggaggacaccgtgct
ccctcgggacctgctctggattccggcccggacgtccccttggagctctgcatctccaacctggaacccaacccagaagtctcaagat
gacgcatcacgtggcgtgcggatccactgagggtccacagagaggggcgcccatctcctgcgtctcagttatcctggtgagggaattc
tgtgccctaaagaattccgactcagatccgaacggggatctggtggaatcgagggtgaaagaccagagggacaATGTTCTACTATCCC
AACGTGCTTCAGCGCCACACCGGCTGCTTTGCCACCATCTGGCTGGCGGCGACTCGCGGCAGCCGGTTGGTGAAGCGCGAATACCTGA
GGGTGAATGTGGTGAAAACCTGCGAGGAAATCCTCAATTACGTGCTGGTACGAGTGCAACCCCCGCAGCCCGGCCTGCCGCGGCCCCG
CTTCTCCCTCTATCTCTCAGCCCAACTTCAGATCGGTGTGATCCGCGTCTATTCTCAACAATGCCAGTACCTCGTGGAGGACATCCAG
CACATCTTGGAGCGCCTCCACCGTGCCCAGCTGCAGATCCGAATAGATATGGAGACTGAGCTACCCAGCCTGCTGCTTCCTAACCACC
TGGCCATGATGGAGACCCTAGAAGATGCTCCAGATCCCTTTTTTGGGATGATGTCTGTGGATCCCAGACTTCCTAGTCCTTTCGATAT
CCCTCAGATTCGACACCTCTTAGAGGCTGCAATCCCAGAGAGAGTTGAAGAGATCCCTCCTGAAGTTCCTACAGAGCCCAGGGAGCCA
GAGAGGATTCCGGTCACTGTGCTGCCACCTGAGGCCATCACGATCCTGGAGGCAGAGCCCATACGGATGCTGGAGATTGAGGGTGAAC
GGGAGCTCCCAGAGGTCAGCCGCCGAGAACTGGACCTGCTGATCGCAGAGGAAGAAGAAGCTATCTTGTTAGAAATCCCGCGGCTCCC
ACCTCCAGCTCCTGCAGAGGTGGAAGGAATAGGAGAGGCACTGGGTCCTGAGGAGCTGAGGCTGACAGGCTGGGAACCTGGGGCCCTA
CTCATGGAGGTGACCCCCCCGGAGGAGCTGCGTCTGCCAGCCCCACCCAGCCCAGAGAGGAGGCCCCCAGTCCCCCCACCTCCTCGCC
GCCGCCGTCGTCGCCGGTTACTGTTCTGGGACAAGGAGACTCAGATCTCCCCGGAGAAATTCCAGGAACAACTGCAAACCAGAGCCCA
CTGCTGGGAATGTCCTATGGTGCAGCCGCCCGAGAGGACCATCAGAGGCCCTGCGGAGTTGTTCAGAACCCCAACTCTCTCTGGCTGG
CTACCCCCTGAACTACTGGGTCTCTGGACCCATTGTGCCCAGCCACCCCCAAAAGCCCTCAGGCGAGAGCTGCCTGAGGAGGCAGCCG
CTGAGGAGGAAAGGAGAAAGATTGAAGTTCCAAGTGAGATTGAGGTCCCGAGGGAGGCCCTGGAGCCCAGTGTTCCCCTTATGGTGTC
TTTAGAGATCTCCCTAGAGGCAGCTGAAGAGGAGAAGTCCCGCATCAGCCTCATCCCACCAGAAGAACGGTGGGCCTGGCCTGAGGTG
GAGGCGCCAGAAGCTCCTGCATTGCCCGTGGTGCCTGAACTCCCTGAGGTGCCCATGGAGATGCCTTTGGTGCTGCCCCCAGAGCTCG
AGCTGCTCTCACTGGAAGCAGTGCACAGGGCAGTGGCACTGGAGCTGCAGGCTAACAGGGAGCCCGACTTCAGCAGCCTGGTGTCACC
TCTCAGCCCCCGCAGGATGGCTGCCCGGGTCTTCTACCTGCTCCTGGTGCTCTCAGCGCAACAGATTCTTCACGTGAAACAAGAAAAG
CCATATGGTCGCCTCCTGATCCAGCCGGGGCCCAGATTCCACTGA ggttagagtccatttacaaagctgccaggaaaccggccactt
ctagtaaaccacgtcgtgcctcactgggtcctgcttacctcatttctgaatgtgcatttccagccttcttgctctcagagctattgac
aagcagaaaacaagctgcttttattacagtaaaaaaaaaaaaaaaaaaaaa Protein coding sequence (SEQ ID NO: 2)
ATGTTCTACTATCCCAACGTGCTTCAGCGCCACACCGGCTGCTTTGCCACCATCTGGCTGGCGGCGACTCGCGGCAGCCGGTTGGTGA
AGCGCGAATACCTGAGGGTGAATGTGGTGAAAACCTGCGAGGAAATCCTCAATTACGTGCTGGTACGAGTGCAACCCCCGCAGCCCGG
CCTGCCGCGGCCCCGCTTCTCCCTCTATCTCTCAGCCCAACTTCAGATCGGTGTGATCCGCGTCTATTCTCAACAATGCCAGTACCTC
GTGGAGGACATCCAGCACATCTTGGAGCGCCTCCACCGTGCCCAGCTGCAGATCCGAATAGATATGGAGACTGAGCTACCCAGCCTGC
TGCTTCCTAACCACCTGGCCATGATGGAGACCCTAGAAGATGCTCCAGATCCCTTTTTTGGGATGATGTCTGTGGATCCCAGACTTCC
TAGTCCTTTCGATATCCCTCAGATTCGACACCTCTTAGAGGCTGCAATCCCAGAGAGAGTTGAAGAGATCCCTCCTGAAGTTCCTACA
GAGCCCAGGGAGCCAGAGAGGATTCCGGTCACTGTGCTGCCACCTGAGGCCATCACGATCCTGGAGGCAGAGCCCATACGGATGCTGG TABLE 5-continued

REC8 MEIOTIC RECOMBINATION PROTEIN [HOMO SAPIENS (HUMAN)]

```
AGATTGAGGGTGAACGGGAGCTCCCAGAGGTCAGCCGCCGAGAACTGGACCTGCTGATCGCAGAGGAAGAAGAAGCTATCTTGTTAGA
AATCCCGCGGCTCCCACCTCCAGCTCCTGCAGAGGTGGAAGGAATAGGAGAGGCACTGGGTCCTGAGGAGCTGAGGCTGACAGGCTGG
GAACCTGGGGCCCTACTCATGGAGGTGACCCCCCCGGAGGAGCTGCGTCTGCCAGCCCCACCCAGCCCAGAGAGGAGGCCCCCAGTCC
CCCCACCTCCTCGCCGCCGCCGTCGTCGCCGGTTACTGTTCTGGGACAAGGAGACTCAGATCTCCCCGGAGAAATTCCAGGAACAACT
GCAAACCAGAGCCCACTGCTGGGAATGTCCTATGGTGCAGCCGCCCGAGAGGACCATCAGAGGCCCTGCGGAGTTGTTCAGAACCCCA
ACTCTCTCTGGCTGGCTACCCCCTGAACTACTGGGTCTCTGAACCATCATTGTGCCCAGCCACCCCCAAAAGCCCTCAGGCGAGAGCTGC
CTGAGGAGGCAGCCGCTGAGGAGGAAAGGAGAAAGATTGAAGTTCCAAGTGAGATTGAGGTCCCGAGGGAGGCCCTGGAGCCCAGTGT
TCCCCTTATGGTGTCTTTAGAGATCTCCCTAGAGGCAGCTGAAGAGGAGAAGTCCCGCATCAGCCTCATCCCACCAGAAGAACGGTGG
GCCTGGCCTGAGGTGGAGGCGCCAGAAGCTCCTGCATTGCCCGTGGTGCCTGAACTCCCTGAGGTGCCCATGGAGATGCCTTTGGTGC
TGCCCCCAGAGCTCGAGCTGCTCTCACTGGAAGCAGTGCACAGGGCAGTGGCACTGGAGCTGCAGGCTAACAGGGAGCCCGACTTCAG
CAGCCTGGTGTCACCTCTCAGCCCCCGCAGGATGGCTGCCCGGGTCTTCTACCTGCTCCTGGTGCTCTCAGCGCAACAGATTCTTCAC
GTGAAACAAGAAAAGCCATATGGTCGCCTCCTGATCCAGCCGGGGCCCAGATTCCACTGA genomic sequence (SEQ ID NO: 3)
hg38_dna range = chr14: 24171853-24180257
ACTAGAGGCGAGAACCGGAGCCCATTGGTCGGAACACCTCACAATGGACCCCAGCGGCGCGCAAAATCCTTATGATTGGTTTGCTGGC
TGCCTCGGGAGACCCTGTTGCCAGGATACTTGGCGTTCCCGACCCGACCCCCGTTCCCATTGGCTGTCAGGGCAAAAGCCGCCATCT
AATGAGGAGCGAGGTGCGGTGCCCCGAAGCGCTCGCTTCCCGCGGTGCGATCTAGTCCTGCAGTAGGCGGCCCGGGGCCACACCGCGG
CCGCCCAAGCCAGTGCAAGGCCCAGGGGCCTGACATCGCTCCCAGCGCTCGAGGACCCGAGGCCTGCTGTGGAGGACACCGTGCTCCCT
CGGGACCTGCTCTGGATTCCGGCCGGACGTCCCCTTGGAGCTCTGCATCTCCAACCTGGAACCCAACCCAGAAGTCTCAAGTTTGAC
GCATCACGTGGCGTGCGGATCCACTGAGGGTCCACAGAGAGGGGCGCCCATCTCCTGCGTCAGTTATCCTGGTAATTGTGTATCTG
CCCATTGTTCGTTGCCTCATTAACTTGGCTTTCTAGGTGCACCCACCTTGCCACCAGAGAAGTCCAAATCCTGACTTCTCTCCAAGGT
GTTGGGAATTCTGTGCCCTAAAGAATTCCGACTCAGATCCGAACGGGGATCTGGTGGAATCGAGGGTGAAAGACCAGAGGGACAATGT
TCTACTATCCCAACGTGCTTCAGCGCCACACCGGCTGCTTTGCCACCATCTGGTAAGGGCGGGGCCCGTTGGCGCGCGATGGCGGACG
CTGCCCGGGATCCCAGCCTGACAGCTCCCCCTCCATCCCCATTCTCCCACCTTCCCACCCACTTCAGGCTGGCGGCGACTCGCGGCA
GCCGGTTGGTGAAGCGCAATACCTGAGGGTGAATGTGGTGAAAACCTGGTAAGGCCCAGAAAAGGGAAGGAGGGCCTGGTGCGGGGG
GTGAGTTAGGGGATGGGGTGGCCAAGACTGTGGGCCCACTCCTGGACGCAGCGGTAATCAGGGCCATTGTTCCCCAGCGAGGAAATC
CTCAATTACGTGCTGGTACGAGTGCAACCCCCGCAGCCCGGCCTGCCGCGGCCCCGCTTCTCCCTCTATCTCTCAGCCCAACTTCAGA
TCGGTGTGATCCGCGTCTATTCTCAACAATGCCAGTACCTCGTGGGTAAGGCTGGGAACCCTCAAAGGTGGGGCGGGCTGAGCAGCTG
TCTGCTAAGCTGGCTGTCTACCTCGTCCTCCCTGCCCACAGAGGACATCCAGCACATCTTGGAGCGCCTCCACCGTGCCCAGCTGCAG
ATCCGAATAGATATGGAGACTGAGCTGAGTGTGCCCTGGGCTTTGATGGAACACCTGCTAGCTTGGCCTCAGCCTGGCTCAGCCT
CAGTCCTTCACGGCCTACATTCTCTCCCAGACCCAGCCTGCTGCTTCCTAAACCACCTGGCCATGATGGAGACCCTAGAAGATGCTCCA
GATCCCTTTTTTGGGATGATGTCTGTGGATCCCAGACTTCCTAGTCCTTTCGATATCCCTCAGGTAGGGCTCATTCCCCAAGACTCGT
GAATTGGCAATGCAGAAGGGGAGTGCTGTCCCTGTGTCACTCTGACATTGGGGTTGGGGAAGGAAGCTTACCACAGCTCTCTCCCACA
GGAGATGGTGCAGGGGGACTGCCAAGGTGGACCCATCCAGGCGAAGCCCCCTGTACTTACCTACTCAGGGCCAATCTGATCAGACGGT
TTCCCCACTGGAGGCAGCTCTTGTCCCCACTTGTCTCCACACTGTTTTCACTGCCAAGGCCCTAATCCAGGCTCTCATCTCTCTGCAC
TGGGCTTTCTTACCCCTGTCCTCCTCCATCTATTCCCAATACTCCTACAGCTTAATGTCACCCCCTTCCTTGGTTCCCCATTTGAACA
GTGGCTCCTGCTGCAAACAGATTACTAGCATTTGGGGCTCTCCATGCCCCATTTATTTCTTTTTTTATTTTATTACTATTATTATTAT
TATTTTTGAGACAGGATCTTGCTCTGTGGCCCAGGCTGGAGTGCAGTGGCACGATCTCAGCTTACTGCAACCTCTGCCTCCCCGGTTC
AAGCAATTCTCCTGCCTCAGCCTCCCGAGTAGCTGGGACTACAGGCATTTGCCACCATGCCCAACTGATTTCTCTGCCTCGGCCT
CAGGGTTTCACCATGCTGGCCAGGCTGGTTTCGAACCCCTGACCTCATGATCTGCCTGTCTCCTCCTCCTGAAGTGCTGGGATTACAG
ACATGAGCCACAGAGCCCGGCCCAATTTTTTTAGGGTTTCGCCTTATCGGCCAGGCTGGTCTCGAACTCCAGACCTCAGGTGATCCAC
CCACCCTGGCTTTCCAAAGTGCTAGGATTACAGACGTGAGCCATCGCGCTGGCCTATTATTATTATTTTTTTGAAATGGAGTCTCTGTC
ACCCAGGCTGGAGTGCAGTGGCATGATCTTGGCTCACTTCAACCTCCGCTTCCTCTGGTCAAGCGATTCTCCTGCCTCGGCCTCCCGA
ATAGCTGGGATTACAGATGCCTGCCACCATGCCCGGCTAATTTTTGTATCTTTAGTAGAGATGGAGTTTCATCATGTTGGTCAGACTG
GTCTTGAACTCCTGATCTCAGGCACTCCACCCGCCTCGGCCTCCCAAAGTGCTGGGATTACAGGTGTGAACCACCGTGCCTGGCACAT
ACCCCAGTTTAGAACTAGTCATCCCCAGACTTCTCTCTCAGTCCTCTGGGCATCTGTGGCTCCTAAACACTAGTTTGGCCCTTATGCC
TCAATGATGCCACATTCACATCTTTGCTTGTACTGTTTCCCTAGCCCATAATGGTCACCCCTCATCCTCTACAAGTCGGGTTCTACAT
ATTCTTACAGACCTGGCTCAAATGCTGCCCTTCTCTATGAAATATTTATCCCAGTCTTAGCCGGACCAAATGCAGTTTGGGAACTCA
GTACTTTGCTAGGGCCTTGTTTTACCCTTTGCCTTGACTCTTGTGGGGTTACATACAACCTTGTCTCCCACTAGACTTCCTTAAGAT
CAAGAATCTTTTCTGTTCACCTCTGTCAACCACAACACTTGCCAAGGATAACGATGCACTGCTGCTTGCACAAATTTTTTTTTTTTT
TTTTGAGACAGAGTCTTGCTCTGTCACCCAGGCTGGAGTGCAGTGGCTCAATCTCAGCTCACTGCAATCTCTGCTTCCCAGGTTCAAG
CAATTCTCCTGTCTCCGCCTCTCAAGTAGCTGGAATTACAGGCACTGCTACCAAGCCCGGCTAATTTTTGTATTTTTAGTAGAAATCA
GGTTTCACGATGTTGGCCAGGCTGGTCTGGAACTCCTGACATCAAGTGATCCACCCACCTCAGCCTCCCAAAGTGCTGGGATTACAGA
CATGAGCCACCGAGCCCGGCCTTCTTGCACAAATTGATGAGGGCTAGATAACTGGGGTGCGGGTTGGGGAGGGAGGTGAGAACAGGAA
CTGAGGAAAGAAGACCAGAGGGCGGGTGAGTTTACTGCAAGCTGATGTCAATGCAACAGGAATTAGGCATAAAAGGAGATTACCGTGC
ATTGTTGAAGAAGGCTGTGAAAAGTGGGAAAGCAGGGGGCTGAAGCTGAACCCTATCTTTGTTTCCAATCCCTCTCCAAAGATTCGA
CACCTCTTAGAGGCTGCAATCCCAGAGAGAGTTGAAGAGATCCCTCCTGAAGTTCCTACAGAGCCCAGGGAGCCAGGTCAGCAGAGAG
AACCTTCTTTCTGGTGAGAGGCATAGGCAGGCCCAAGAGCTGTAGAAATGACCATTTTTGAGCTTAAGAGCCAGGCCTTGTGAGGGGC
GCTTTTTTTTTTTCGAGGCAGAGTCTCACTCTGTTGCCCAGGCTACAGTGCAGTGGCACGATCTCGGCTCACTGCAAGCAATTGTC
CCGCCTCAGCCTCCCTAGTAGCTGGGATTACAGATGTGCACTACCATGCCCGGCGAATTTTTGTATTTTTAGTAGAGATGGGGTTTCA
CCATGTTGGCCAGGCTGGTCTCAAACTCCTGACCTCAGGTGATCCACCCGCCTCGGCCTCCCAAAGTGCTAGGATTACAGGTGTGAGC
CACCGTGCCTGGTGAGGGGCATTTTATGTGTATAACCTCATCAGTACCTCACAAGAGTCCTCTGAGGTCAGATTTCTTATCTTTTTT
TTTTTTGAGAGATGGGGTATCACTCTCTAGCCCAGGCTGGAGTACAGTGGTGCACTTTAGGCTCACTGCAACCTCCGCCTCCCGGATT
CAAGCAATTCTCCTTCCTAGTAGCTGGGATTACAGGCATGCACCACCACGCCCAGCTAATTTTCGTATTTTTAGTAGAGATGGGTTTT
TGCCATGTTGGCCAGGCTGGTCTCAAACTTCTGACCTCAGTTGATCCACCCACCTCAGCCTCCCAAAGTGCTGGGATTACAGGCGTGA
GCCACCACTACTCGGCTTTTTTTTTTTTTTTTCTTTTTTCCCAGGCTGGAGTGCAGTGGTATGATGATCATAGGTCACTGCAGCCTT
GACCTCCAGGGCTCAAGCAATCCTCCCACCTCAGCCTCCAGAGTAGCTGGGACCACAAGGATAAGCCACCACACCTGGCTAGTTTTA
AATTTTTTGTAGAGACAGGGTCTCGCTATGTTGCCCAGGCTGGCTCAAACTCCTGGGCTCAAGCGATCCAAAGTGTTGGGATTACAG
GTGTGAGCCACTTCGCCCAGCCTCCCCACTTTACCGATGAGGAAAGTGAGGCTCACAGTGGTTAAGCAGTGTACCCAGGGTCAGGATG
CCAGAGATTAGCCTGGGTCTGATTAGAATCCAGGTTACCTTGACTTCAGAGTCCATGCTTTTCCTTAACTGCATGGCTGTGGGAATTT
GGAAAGAAGCAGAGAGGCTAGTGACTCTCTTGTCCCTCCAGAGAGGATTCCGGTCACTGTGCTGCCACCTGAGGCCATCACGATCCTG
GAGGCAGAGCCCATACGGAGTGCTGGAGATTGAGGTGAGTTCCCCTGCACACAGGGCCTGAGGTCCAGCCCCCTTGCATGTACTTCTCT
CTGTCCCCAGAGTCCTGCCTTTTCTGTCTCCATTTCCCTATTCTCTGTCCCTGGCACTTGAGCACCCAGTGGCTTCCTTGAACCTGGC
CCTGTGGCATGCCTCTGGGATCCACTCTCCTGGATCCACTTGCCTTTTTCAGAAATATTATTGAATCCCCTCCCCTTGCTCTTCCTCT
CTGGACAGGGTGAACGGGAGCTCCCAGAGGTCAGCCGCCGAGAACTGGACCTGCTGATCGCAGAGGAAGAAGAAGCTATCTTGTTAGA
AAGTAGGTGTCTCCGGCAGCGTAGGGCCCGCTGGAGCTGGATAGTCAGACCCCTGGCGTGGGCATTCTGGGACTGGCAATGCTCCC
ATTTCTCTTTTTCTGTCCTCTGAACTCTGATTCTCTCCACAGTCCCGCGGCTCCCACCTCCAGCTCCTGCAGAGTAAGGGCAAGAA
```

TABLE 5-continued

REC8 MEIOTIC RECOMBINATION PROTEIN [*HOMO SAPIENS* (HUMAN)]

```
CTCCTAGACCAGGTAGGGTGTCAGTGCTGGGAAGGGTCTCCTCATTTCTCTTGCCCATTTCCCCTCAGGGTGGAAGGAATAGGAGAGG
CACTGGGTCCTGAGGAGCTGAGGCTGACAGGCTGGGAACCTGGGGCCCTACTCATGGGTGAGTGCCCACCATGCCCCAGGGGCTTTTC
TGGGGAGTACCTGGATACTGCTGCAGACAAGGGCTTTATATCCCAACTTGCTAAAGGGAGGACCCTGCAGTTTCTTGCCCTGGCATCTG
CAAGGGGTAAGGGGCTTATGGGACAGAGCCCCTTGGGTGTTGTTGCAGAGGTGACCCCCCGGAGGAGCTGCGTCTGCCAGCCCCACC
CAGCCCAGAGGTGAGTAGCCTCCCTTCTAATCCTCCTCCTCCTCCTCTTTGCCCTCCCCCACAAGGACTGCCTCCCCAAGCCCAGGGC
CACTGCTAGCTTTACAGGGGTCCTTAATGCAGATGATAAAAGATGCCCCTTTCTACGCCCCATCGTATCTGGCCTACGCTTCCCAGATG
GGTACCCTTATGCAAGGTATGAGCTGCTCAAGTGCATGGAGACCCCGCACAAGCCCTCTCCAGGTTCCTCTAGGGGCGGGTGTGGGGT
CCTGTTAGCAGTCCACCAGAATGACAGGAAAAGGAGTAATGGGCAGCCTTGCCCCTACCTGCCCTCCCCACTCAACAGAGGAGGCCCC
CAGTCCCCCACCTCCTCGCCGCCGCCGTCGTCGCCGGTTACTGTTCTGGGACAAGGAGACTCAGATCTCCCCGGAGAAATTCCAGGA
ACAACTGCAAACCAGAGCCCACTGCTGGGAATGTGTGAGTGCAGCCCAGGCTTTGCCGGGGAAGGGAGGGAGGCAGGGATGACCAGGG
GCACATGCAGGCTGAGCCTTCCAAACTCCTCAGGTGGGTGGGGGGAGGATTGGAACTTGATGAAAAATCTCCTCCATTCTCCAGAAA
ATGCAGGCGATGTGGGTTTGCACATATACAACTCTTCATGCTCCTTTAGTGACCCACCTGTCATACCCATGGGCACCAGGTTAAAAAG
TCCTTCTTTTAGCAATGAGCAGGGCAGGCAGGGTCATGAGCGCAAAAGCTGGGGAAGTCCAGAAGCCCCAGAACAGTGCATTGCAAAG
AGGCAAAGGGGCCCTGAGGAGTGGCTGCTTTATAATGGGGCTTCTGACCTTCCCCCACTACACAGCCTATGGTGCAGCCGCCCGAGAG
GACCATCAGAGGCCCTGCGGAGTTGTTCAGAACCCCAACTCTCTGTAAGAATGGTGGGGGTTGGGCACGAAGTATCCTCAAAACCAAT
TCCTCATTCCTGGTGCTCCTCACGCCTCAAACCCCGTGCCTACTACCCTCTTGTCCACAGCTGGCTGGCTACCCCTGAACTACTGGG
TCTCTGGACCCATTGTGCCCAGCCACCCCCAAAAGCCCTCAGGCGAGAGCTGCCTGAGGAGGCAGCCGCTGAGGAGGAAAGGAGAAAG
ATTGAAGTTCCAAGTGAGATTGAGGTAACTGCACCACCTGTTTACTGCATCGCCCCAGTGCCAGGGTCTGCCTGACCAGCTGGCTGCC
CTCTCCTGCTATGAGAGCCAACAGCACAGGCTCACTGGCCTTGTGACCCCCAAGTCCCAGATGCTTGGGGTCTTAGTTCTA
CTTCTCCCATCCCCAGGTCCCGAGGGAGGCCCTGGAGCCCAGTGTTCCCCTTATGGTGTCTTTAGGTAAGCACCTAGAGAAGAGGCGC
AGTGGGACCACACCCTAACCACTGTCCCAGGAAACTAGTATCCCAACTGCTGAAGCTGTTTTATGAGTGAAGGCGTGTGTGTGACA
TAAGGAAGCACGGACTGGTCCTCCTCAGCTCTCCCACCTATGTGCTTTTAACAAGTCACCGCACGGCTCTGCCATCTACTTACACCAG
GTGGCCACAAGGCCCTAACTGCCACCCAAGCAGACACCCACTAGCGCCTTTCCTCCCCAACAGAGATCTCCCTAGAGGCAGCTGAAG
AGGAGAAGTCCCGCATCAGCCTCATCCCACCAGAAGAACGGTGGTAAGCGGCCAGGCTCCGTGGGAGACCAGGGCCCACAGCCCTTGGC
CAGGTGGTGGAAACAGCTGCTGGGATGGGTATGCCCCTTGTCACTGTCACAGCTGCCACCTTCCCTACTCTCTCATGTCCTCCTAGGG
CCTGGCCTGAGGTGGAGGCGCCAGAAGCTCCTGCATTGCCCGTGGTGCCTGAACTCCCTGAGGTGCCCATGGAGATGCCTTTGGTGCT
GCCCCCAGAGCTCGAGCTGCTCTCACTGGAAGCAGTGCACAGGTACCAGGGAGGTGGCACCTTGATGGGGTGGACCCGGGCTGAAGCC
TCTGCTAATGGTTCTTGATCCCTATAGGGCAGTGGCACTGGAGCTGCAGGCTAACAGGGAGCCCGACTTCAGCAGCCTGGTGTCACCT
CTCAGCCCCGCAGGATGGCTGCCCGGGTCTTCTACCTGCTCCTGGGTGAGTGTATGCATGTGTGTGTGTATGTGGGGCAGGGACA
CAGAGACCAGAGGCCCGTACAGGGACTCCCCCGACCTGCCCTCTCCTCGCCTCTTGACCAGTGCTCTCAGCGCAACAGATTCTTCACG
TGAAACAAGAAAAGCCATATGGTCGCCTCCTGATCCAGCCGGGGCCCAGATTCCACTGAGGTTAGAGTCCATTTACAAAGCTGCCAGG
AAACCGGCCACTTCTAGTAAACCACGTCGTGCCTCACTGGGTCCTGCTTACCTCATTTCTGAATGTGCATTTCCAGCCTTCTTGCTCT
CAGAGCTATTGTTCAAGCAGAAAACAAGCTGCTTTTATTACAGTA

REC8 protein sequence NP_005123.2 (SEQ ID NO: 4)
MFYYPNVLQRHTGCFATIWLAATRGSRLVKREYLRVNVVKTCEEILNYVLVRVQPPQPGLPRPRFSLYLSAQLQIGVIRVYSQQCQYL
VEDIQHILERLHRAQLQIRIDMETELPSLLLPNHLAMMETLEDAPDPFFGMMSVDPRLPSPFDIPQIRHLLEAAIPERVEEIPPEVPT
EPREPERIPVTVLPPEAITILEAEPIRMLEIEGERELPEVSRRELDLLIAEEEEAILLEIPRLPPPAPAEVEGIGEALGPEELRLTGW
EPGALLMEVTPPEELRLPAPPSPERRPVPPPPRRRRRRLLFWDKETQISPEKFQEQLQTRAHCWECPMVQPPERTIRGPAELFRTP
TLSGWLPPELLGLWTHCAQPPPKALRRELPEEAAAEEERRKIEVPSEIEVPREALEPSVPLMVSLEISLEAAEEEKSRISLIPPEERW
AWPEVEAPEAPALPVVPELPEVPMEMPLVLPPELELLSLEAVHRAVALELQANREPDFSSLVSPLSPRRMAARVFYLLLVLSAQQILH
VKQEKPYGRLLIQPGPRFH
```

Primer Sequences Used in Example 1

| Name | sequence (5'->3') | Amplicon Size |
|---|---|---|
| REC8-BGS-F | GTAAAATTTTTATGATTGGTTTGTTG (SEQ ID NO: 9) | 232 bp |
| REC8-BGS-R | CCCCTAAACCTTACACTAACT (SEQ ID NO: 10) | |

REC8 BGS target

Unconverted DNA target

>hg38_dna range = chr14: 24171913-24172144
5'pad = 0 3'pad = 0 strand = +
repeatMasking = none

SEQ ID NO: 5
GCAAAATCCTTATGATTGGTTTGCTGGCTGCCTCGGGAGACCCTGTTGCC

AGGATACTTGGCGTTCCCGACCCGACCCCCGTTCCCCATTGGCTGTCAGG

GCAAAAGCCGCCATCTAATGAGGAGCGAGGTGCGGTGCCCCGAAGCGCTC

GCTTCCCGCGGTGCGATCTAGTCCTGCAGTAGGCGGCCCGGGGCCACACC

GCGGCCGCCCAAGCCAGTGCAAGGCCCAGGGG

Bisulfite converted target

SEQ ID NO: 6
GtaaaattttttatgattggtttgttggttgttttCGggagattttgttgtt aggatatttggCGttttCGattCGattttCattttttattggttgttaggg taaaagtCGttatttaatgaggagCGaggtgCGgtgtttCGaagCGttCG ttttttCGtggtgCGatttagttttgtagtaggCGgttCGggttatatCG CGgtCGtttaagttagtgtaaggtttagggg Primer and Probe Sequences Used in Example 2

| Name | Sequence (5'->3') | Amplicon Size |
|---|---|---|
| Forward | GAGGAAATTTTTAATTAYGTGTTGGT (SEQ ID NO: 11; Y = C/T) | 163 bp |
| Reverse | TTTAAAAATTCCCAACCTTACCC (SEQ ID NO: 12) | |
| M-probe | TGTGATTCGCGTTTATTTTTAATAAT (SEQ ID NO: 13) | |
| U-probe | TGTGATTTGTGTTTATTTTTAATAATGTTAGTAT (SEQ ID NO: 14) | |

REC8 Meth-qPCR target

Unconverted DNA target

>hg38_dna range = chr14: 24172900-24173062
5'pad = 0 3'pad = 0 strand = +
repeatMasking = none

SEQ ID NO: 7
GAGGAAATCCTCAATTACGTGCTGGTACGAGTGCAACCCCCGCAGCCCGG

CCTGCCGCGGCCCCGCTTCTCCCTCTATCTCTCAGCCCAACTTCAGATCG

GTGTGATCCGCGTCTATTCTCAACAATGCCAGTACCTCGTGGGTAAGGCT

GGGAACCCTCAAA

Bisulfite converted target

SEQ ID NO: 8
gaggaaatttttaattaCGtgttggtaCGagtgtaattttCGtagttCGg tttgtCGCGgtttCGttttttttttattttttagtttaattttagatCG gtgtgattCGCGtttatttttaataatgttagtatttCGtgggtaaggtt gggaattttaaa

LIST OF REFERENCES

1 Torre L A, Bray F, Siegel R L, Ferlay J, Lortet-Tieulent J, Jemal A (2015). Global cancer statistics, 2012. *C A: a cancer journal for clinicians* 65: 87-108.
2 Wang S, Cheng Y, Du W, Lu L, Zhou L, Wang H et al (2013). Zinc-finger protein 545 is a novel tumour suppressor that acts by inhibiting ribosomal RNA transcription in gastric cancer. *Gut* 62: 833-841.
3 Xu L, Li X, Chu E S, Zhao Go M Y, Tao Q et al (2012). Epigenetic inactivation of BCL6B, a novel functional tumour suppressor for gastric cancer, is associated with poor survival. *Gut* 61: 977-985.
4 Yu J, Cheng Y Y, Tao Q, Cheung K F, Lam C N, Geng H et al (2009). Methylation of protocadherin 10, a novel tumor suppressor, is associated with poor prognosis in patients with gastric cancer. *Gastroenterology* 136: 640-651 e641.
5 Yu J, Liang Q Y, Wang J, Cheng Y, Wang S, Poon T C et al (2013). Zinc-finger protein 331, a novel putative tumor suppressor, suppresses growth and invasiveness of gastric cancer. *Oncogene* 32: 307-317.
6 Camargo M C, Kim W H, Chiaravalli A M, Kim K M, Corvalan A H, Matsuo K et al (2014). Improved survival of gastric cancer with tumour Epstein-Barr virus positivity: an international pooled analysis. *Gut* 63: 236-243.
7 Zhao J, Liang Q, Cheung K F, Kang W, Lung R W, Tong J H et al (2013). Genome-wide identification of Epstein-Barr virus-driven promoter methylation profiles of human genes in gastric cancer cells. *Cancer* 119: 304-312.
8 Cancer Genome Atlas Research Network; Bass A J T V, Shmulevich I, Reynolds S M, Miller M, Bernard B, Hinoue T, Laird P W, Curtis C, Shen H, et al. (2014). Comprehensive molecular characterization of gastric adenocarcinoma. *Nature* 513: 202-209.
9 Liang Q, Yao X, Tang S, Zhang J, Yau T O, Li X et al (2014). Integrative identification of Epstein-Barr virus-associated mutations and epigenetic alterations in gastric cancer. *Gastroenterology* 147: 1350-1362 e1354.
10 Hino R, Uozaki H, Murakami N, Ushiku T, Shinozaki A, Ishikawa S et al (2009). Activation of DNA methyltransferase 1 by EBV latent membrane protein 2A leads to promoter hypermethylation of PTEN gene in gastric carcinoma. *Cancer Res* 69: 2766-2774.
11 Sudo M, Chong J M, Sakuma K, Ushiku T, Uozaki H, Nagai H et al (2004). Promoter hypermethylation of E-cadherin and its abnormal expression in Epstein-Barr virus-associated gastric carcinoma. *Int J Cancer* 109: 194-199.
12 Zhao J, Liang Q, Cheung K F, Kang W, Dong Y, Lung R W et al (2013). Somatostatin receptor 1, a novel EBV-associated CpG hypermethylated gene, contributes to the pathogenesis of EBV-associated gastric cancer. *Br J Cancer* 108: 2557-2564.
13 Nasmyth K (2001). Disseminating the genome: joining, resolving, and separating sister chromatids during mitosis and meiosis. *Annu Rev Genet* 35: 673-745.
14 Liu D X, Shen X P, Zhu G W, Xing M Z (2015). REC8 is a novel tumor suppressor gene epigenetically robustly targeted by the PI3K pathway in thyroid cancer. *Oncotarget* 6: 39211-39224.
15 Wockner L F, Morris C P, Noble E P, Lawford B R, Whitehall V L J, Young R M et al (2015). Brain-specific epigenetic markers of schizophrenia. *Transl Psychiat* 5.
16 Okamoto Y, Sawaki A, Ito S, Nishida T, Takahashi T, Toyota M et al (2012). Aberrant DNA methylation associated with aggressiveness of gastrointestinal stromal tumour. *Gut* 61: 392-401.
17 Budczies J, Klauschen F, Sinn B V, Gyorffy B, Schmitt W D, Darb-Esfahani S et al (2012). Cutoff Finder: a comprehensive and straightforward Web application enabling rapid biomarker cutoff optimization. *PloS one* 7: e51862.
18 Mikeska T, Candiloro I L, Dobrovic A (2010). The implications of heterogeneous DNA methylation for the accurate quantification of methylation. *Epigenomics* 2: 561-573.
19 Du W, Jiang P, Mancuso A, Stonestrom A, Brewer M D, Minn A J et al (2013). TAp73 enhances the pentose phosphate pathway and supports cell proliferation. *Nat Cell Biol* 15: 991-1000.
20 Kim M O, Lee Y J, Park J H, Ryu J M, Yun S P, Han H J (2012). PKA and cAMP stimulate proliferation of mouse embryonic stem cells by elevating GLUT1 expression mediated by the NF-kappaB and CREB/CBP signaling pathways. *Biochim Biophys Acta* 1820: 1636-1646.
21 Medina-Ramirez C M, Goswami S, Smirnova T, Bamira D, Benson B, Ferrick N et al (2011). Apoptosis inhibitor ARC promotes breast tumorigenesis, metastasis, and chemoresistance. *Cancer Res* 71: 7705-7715.
22 Ying J, Srivastava Hsieh W S, Gao Z, Murray P, Liao S K et al (2005). The stress-responsive gene GADD45G is a functional tumor suppressor, with its response to environmental stresses frequently disrupted epigenetically in multiple tumors. *Clin Cancer Res* 11: 6442-6449.
23 Liu J Y, Qian D, He L R, Li Y H, Liao Y J, Mai S J et al (2013). PinX1 suppresses bladder urothelial carcinoma cell proliferation via the inhibition of telomerase activity and p16/cyclin D1 pathway. *Mol Cancer* 12: 148.
24 Regel I, Eichenmuller M, Joppien S, Liebl J, Haberle B, Muller-Hocker J et al (2012). IGFBP3 impedes aggressive growth of pediatric liver cancer and is epigenetically silenced in vascular invasive and metastatic tumors. *Mol Cancer* 11: 9.
25 Kabbout M, Garcia M M, Fujimoto J, Liu D D, Woods D, Chow C W et al (2013). ETS2 mediated tumor suppressive function and MET oncogene inhibition in human non-small cell lung cancer. *Clin Cancer Res* 19: 3383-3395.

26 Pruitt S C, Bailey K J, Freeland A (2007). Reduced Mcm2 expression results in severe stem/progenitor cell deficiency and cancer. *Stem Cells* 25: 3121-3132.
27 Deep Jain A K, Ramteke A, Ting H, Vijendra K C, Gangar S C et al (2014). SNAI1 is critical for the aggressiveness of prostate cancer cells with low E-cadherin. *Mol Cancer* 13: 37.
28 Zhang Z, Zhang B, Li W, Fu L, Zhu Z, Dong J T (2011). Epigenetic Silencing of miR-203 Upregulates SNAI2 and Contributes to the Invasiveness of Malignant Breast Cancer Cells. *Genes Cancer* 2: 782-791.
29 Arseneault R, Chien A, Newington J T, Rappon T, Harris R, Cumming R C (2013). Attenuation of LDHA expression in cancer cells leads to redox-dependent alterations in cytoskeletal structure and cell migration. *Cancer Lett* 338: 255-266.
30 Feng W H, Kraus R J, Dickerson S J, Lim H J, Jones R J, Yu X et al (2007). ZEB1 and c-Jun levels contribute to the establishment of highly lytic Epstein-Barr virus infection in gastric AGS cells. *J Virol* 81: 10113-10122.
31 Zhao J, Jin H, Cheung K F, Tong J H, Zhang S, Go M Y et al (2012). Zinc finger E-box binding factor 1 plays a central role in regulating Epstein-Barr virus (EBV) latent-lytic switch and acts as a therapeutic target in EBV-associated gastric cancer. *Cancer* 118: 924-936.
32 Yu J, Leung W K, Ebert M P, Ng E K, Go M Y, Wang H B et al (2002). Increased expression of survivin in gastric cancer patients and in first degree relatives. *Br J Cancer* 87: 91-97.
33 Cerami E, Gao J, Dogrusoz U, Gross B E, Sumer S O, Aksoy B A et al (2012). The cBio cancer genomics portal: an open platform for exploring multidimensional cancer genomics data. *Cancer Discov* 2: 401-404.
34 Gao J, Aksoy B A, Dogrusoz U, Dresdner Gross B, Sumer S O et al (2013). Integrative analysis of complex cancer genomics and clinical profiles using the cBioPortal. *Sci Signal* 6: pl1.
35 Yu J, Liang Q, Wang J, Wang K, Gao J, Zhang J, Zeng Y, Chiu P W, Ng E K, Sung J J. REC8 functions as a tumor suppressor and is epigenetically downregulated in gastric cancer, especially in EBV-positive subtype. *Oncogene* 2017; 36:182-193.
36 DeLong E R, DeLong D M, Clarke-Pearson D L. Comparing the areas under two or more correlated receiver operating characteristic curves: a nonparametric approach. Biometrics 1988; 44:837-45.

What is claimed is:

1. A method for detecting the methylation status of REC8 gene, comprising the steps of:
   (1) treating genomic DNA obtained from a biological sample taken from a subject with a bisulfate;
   (2) performing an amplification reaction to amplify the treated genomic DNA from step (1) using a primer comprising the nucleotide sequence of SEQ ID NO:11 or 12;
   (3) analyzing the product of the amplification reaction from step (2) to determine the methylation status of REC8 gene.

2. The method of claim 1, wherein the biological sample is a tissue sample, a blood, plasma or serum sample, a stool sample, or a urine sample.

3. The method of claim 1, wherein the subject is suspected of having or at risk of developing gastric, liver, or colon cancer.

4. The method of claim 1, wherein step (3) comprises determining the nucleotide sequence of the product of the amplification reaction from step (2).

5. The method of claim 1, wherein step (3) comprises hybridizing the product of the amplification reaction from step (2) with a methylation probe or with a non-methylation probe.

6. The method of claim 5, wherein the methylation probe comprises the nucleotide sequence of SEQ ID NO:13.

7. The method of claim 5, wherein the non-methylation probe comprises the nucleotide sequence of SEQ ID NO:14.

8. The method of claim 1, wherein the amplification reaction in step (2) is a polymerase chain reaction (PCR).

9. The method of claim 8, wherein the PCR is a quantitative PCR (qPCR).

10. The method of claim 8, wherein primers comprising the nucleotide sequence of SEQ ID NOs:11 and 12 are used in the PCR.

* * * * *

SEQUENCE LISTING

<160> NUMBER OF SEQ ID NOS: 14

<210> SEQ ID NO 1
<211> LENGTH: 2253
<212> TYPE: DNA
<213> ORGANISM: Homo sapiens

<400> SEQUENCE: 1

```
atctaatgag gagcgaggtg cggtgcccg aagcgctcgc ttcccgcggt gcgatctagt      60
cctgcagtag gcggcccggg gccacaccgc ggccgcccaa gccagtgcaa ggcccagggg    120
cctgacatcg ctcccagcgc tcgaggaccg aggcctgctg tggaggacac cgtgctccct    180
cgggacctgc tctggattcc ggcccggacg tccccttgga gctctgcatc tccaacctgg    240
aacccaaccc agaagtctca agtttgacgc atcacgtggc gtgcggatcc actgagggtc    300
cacagagagg ggcgcccatc tcctgcgtct cagttatcct ggtgttggga attctgtgcc    360
ctaaagaatt ccgactcaga tccgaacggg gatctggtgg aatcgagggt gaaagaccag    420
agggacaatg ttctactatc ccaacgtgct tcagcgccac accggctgct ttgccaccat    480
ctggctggcg gcgactcgcg gcagccggtt ggtgaagcgc gaatacctga gggtgaatgt    540
ggtgaaaacc tgcgaggaaa tcctcaatta cgtgctggta cgagtgcaac ccccgcagcc    600
cggcctgccg cggccccgct tctccctcta tctctcagcc caacttcaga tcggtgtgat    660
ccgcgtctat tctcaacaat gccagtacct cgtggaggac atccagcaca tcttggagcg    720
cctccaccgt gcccagctgc agatccgaat agatatggag actgagctac ccagcctgct    780
gcttcctaac cacctggcca tgatggagac cctagaagat gctccagatc ccttttttgg    840
gatgatgtct gtggatccca gacttcctag tcctttcgat atccctcaga ttcgacacct    900
cttagaggct gcaatcccag agagagttga agagatccct cctgaagttc ctacagagcc    960
cagggagcca gagaggattc cggtcactgt gctgccacct gaggccatca cgatcctgga   1020
ggcagagccc atacggatgc tggagattga gggtgaacgg gagctcccag aggtcagccg   1080
ccgagaactg gacctgctga tcgcagagga agaagaagct atcttgttag aaatcccgcg   1140
gctcccacct ccagctcctg cagaggtgga aggaatagga gaggcactgg gtcctgagga   1200
```

```
gctgaggctg acaggctggg aacctggggc cctactcatg gaggtgaccc ccccggagga    1260
gctgcgtctg ccagccccac ccagcccaga gaggaggccc ccagtccccc cacctcctcg    1320
ccgccgccgt cgtcgccggt tactgttctg ggacaaggag actcagatct ccccggagaa    1380
attccaggaa caactgcaaa ccagagccca ctgctgggaa tgtcctatgg tgcagccgcc    1440
cgagaggacc atcagaggcc ctgcggagtt gttcagaacc ccaactctct ctggctggct    1500
acccccctgaa ctactgggtc tctgacccca ttgtgcccag ccaccccaa aagccctcag    1560
gcgagagctg cctgaggagg cagccgctga ggaggaaagg agaaagattg aagttccaag    1620
tgagattgag gtcccgaggg aggccctgga gcccagtgtt cccttatgg tgtctttaga    1680
gatctcccta gaggcagctg aagaggagaa gtcccgcatc agcctcatcc caccagaaga    1740
acggtgggcc tggcctgagg tggaggcgcc agaagctcct gcattgcccg tggtgcctga    1800
actccctgag gtgcccatgg agatgccttt ggtgctgccc ccagagctcg agctgctctc    1860
actggaagca gtgcacaggg cagtggcact ggagctgcag gctaacaggg agcccgactt    1920
cagcagcctg gtgtcacctc tcagcccccg caggatggct gcccgggtct tctacctgct    1980
cctggtgctc tcagcgcaac agattcttca cgtgaaacaa gaaaagccat atggtcgcct    2040
cctgatccag ccggggccca gattccactg aggttagagt ccatttacaa agctgccagg    2100
aaaccggcca cttctagtaa accacgtcgt gcctcactgg gtcctgctta cctcatttct    2160
gaatgtgcat ttccagcctt cttgctctca gagctattgt tcaagcagaa aacaagctgc    2220
ttttattaca gtaaaaaaaa aaaaaaaaaa aaa                                 2253

<210> SEQ ID NO 2
<211> LENGTH: 1644
<212> TYPE: DNA
<213> ORGANISM: Homo sapiens

<400> SEQUENCE: 2
atgttctact atcccaacgt gcttcagcgc acaccggct gctttgccac catctggctg     60
gcggcgactc gcggcagccg gttggtgaag cgcgaatacc tgagggtgaa tgtggtgaaa    120
acctgcgagg aaatcctcaa ttacgtgctg gtacgagtgc aaccccgca gcccggcctg    180
ccgcggcccc gcttctccct ctatctctca gcccaacttc agatcggtgt gatccgcgtc    240
tattctcaac aatgccagta cctcgtggag gacatccagc acatcttgga gcgcctccac    300
cgtgcccagc tgcagatccg aatagatatg gagactgagc tacccagcct gctgcttcct    360
aaccacctgg ccatgatgga gaccctagaa gatgctccag atccctttt tgggatgatg    420
tctgtggatc ccagacttcc tagtcctttc gatatccctc agattcgaca cctcttagag    480
gctgcaatcc cagagagagt tgaagagatc cctcctgaag ttcctacaga gcccagggag    540
ccagagagga ttccggtcac tgtgctgcca cctgaggcca tcacgatcct ggaggcagag    600
cccatacgga tgctggagat tgagggtgaa cgggagctcc cagaggtcag ccgccgagaa    660
ctggacctgc tgatcgcaga ggaagaagaa gctatcttgt tagaaatccc gcggctccca    720
cctccagctc ctgcagaggt ggaaggaata ggagaggcac tgggtcctga ggagctgagg    780
ctgacaggct gggaacctgg ggccctactc atgggagtga ccccccggga ggagctgcgt    840
ctgccagccc cacccagccc agagaggagg cccccagtcc cccacctcc tcgccgccgc    900
cgtcgtcgcc ggttactgtt ctgggacaag gagactcaga tctccccgga gaaattccag    960
gaacaactgc aaaccagagc ccactgctgg gaatgtccta tggtgcagcc gcccgagagg   1020
```

| | |
|---|---|
| accatcagag gccctgcgga gttgttcaga acccaactc tctctggctg ctaccccct | 1080 |
| gaactactgg gtctctggac ccattgtgcc cagccacccc caaaagccct caggcgagag | 1140 |
| ctgcctgagg aggcagccgc tgaggaggaa aggagaaaga ttgaagttcc aagtgagatt | 1200 |
| gaggtcccga gggaggccct ggagcccagt gttcccctta tggtgtcttt agagatctcc | 1260 |
| ctagaggcag ctgaagagga aagtcccgc atcagcctca tcccaccaga agaacggtgg | 1320 |
| gcctggcctg aggtggaggc gccagaagct cctgcattgc ccgtggtgcc tgaactccct | 1380 |
| gaggtgccca tggagatgcc tttggtgctg cccccagagc tcgagctgct ctcactggaa | 1440 |
| gcagtgcaca gggcagtggc actggagctg caggctaaca gggagcccga cttcagcagc | 1500 |
| ctggtgtcac ctctcagccc ccgcaggatg gctgcccggg tcttctacct gctcctggtg | 1560 |
| ctctcagcgc aacagattct tcacgtgaaa caagaaaagc catatggtcg cctcctgatc | 1620 |
| cagccggggc ccagattcca ctga | 1644 |

<210> SEQ ID NO 3
<211> LENGTH: 8405
<212> TYPE: DNA
<213> ORGANISM: Homo sapiens

<400> SEQUENCE: 3

| | |
|---|---|
| actagaggcg agaaccggag cccattggtc ggaacacctc acaatggacc ccagcggcgc | 60 |
| gcaaaatcct tatgattggt ttgctggctg cctcgggaga ccctgttgcc aggatacttg | 120 |
| gcgttcccga cccgaccccc gttccccatt ggctgtcagg gcaaaagccg ccatctaatg | 180 |
| aggagcgagg tgcggtgccc cgaagcgctc gcttcccgcg gtgcgatcta gtcctgcagt | 240 |
| aggcggcccg gggccacacc gcggccgccc aagccagtgc aaggcccagg ggcctgacat | 300 |
| cgctcccagc gctcgaggac cgaggcctgc tgtggaggac accgtgctcc ctcgggacct | 360 |
| gctctggatt ccggcccgga cgtccccttg gagctctgca tctccaacct ggaacccaac | 420 |
| ccagaagtct caagtttgac gcatcacgtg gcgtgcggat ccactgaggg tccacagaga | 480 |
| ggggcgccca tctcctgcgt ctcagttatc ctggtaattg tgtatctgcc cattgttcgt | 540 |
| tgcctcatta acttggcttt ctaggtgcac ccaccttgcc accagagaag tccaaatcct | 600 |
| gacttctctc caaggtgttg ggaattctgt gccctaaaga attccgactc agatccgaac | 660 |
| ggggatctgg tggaatcgag ggtgaaagac cagagggaca atgttctact atcccaacgt | 720 |
| gcttcagcgc cacaccggct gctttgccac catctggtaa gggcggggcc cgttggcgcg | 780 |
| cgatggcgga cgctgcccgg gatcccagcc tgacagctcc cctccatcc ccattctccc | 840 |
| accttcccca cccacttcag gctggcggcg actcgcggca gccggttggt gaagcgcgaa | 900 |
| tacctgaggg tgaatgtggt gaaaacctgg taaggcccag aaaagggaag gagggcctgg | 960 |
| tgcgggggt gagttagggg atggggtggc caagactgtg ggcccactcc tggacgcagc | 1020 |
| ggtaatcagg gcgcattgtt ccccagcgag gaaatcctca attacgtgct ggtacgagtg | 1080 |
| caacccccgc agcccggcct gccgcggccc cgcttctccc tctatctctc agcccaactt | 1140 |
| cagatcggtg tgatccgcgt ctattctcaa caatgccagt acctcgtggg taaggctggg | 1200 |
| aaccctcaaa ggtggggcgg gctgagcagc tgtctgctaa gctggctgtc tacctcgtcc | 1260 |
| tccctgccca cagaggacat ccagcacatc ttggagcgcc tccaccgtgc ccagctgcag | 1320 |
| atccgaatag atatggagac tgagctgtga gtgtgccctg ggcctttgat ggaacacctg | 1380 |
| ctagcttggc ctcagcctgg ctcagcctca gtccttcacg gcctacattc tctcccagac | 1440 |
| ccagcctgct gcttcctaac cacctggcca tgatggagac cctagaagat gctccagatc | 1500 |

```
cctttttttgg gatgatgtct gtggatccca gacttcctag tcctttcgat atccctcagg   1560
tagggctcat tccccaagac tcgtgaattg gcaatgcaga aggggagtgc tgtccctgtg   1620
tcactctgac attggggttg gggaaggaag cttaccacag ctctctccca caggagatgg   1680
tgcaggggga ctgccaaggt ggacccatcc aggcgaagcc ccctgtactt acctactcag   1740
ggccaatctg atcagacggt ttccccactg gaggcagctc ttgtcccac ttgtctccac    1800 actgttttca ctgccaaggc cctaatccag gctctcatct ctctgcactg ggctttctta   1860
cccctgtcct cctccatcta ttcccaatac tcctacagct taatgtcacc cccttccttg   1920
gttccccatt tgaacagtgg ctcctgctgc aaacagatta ctagcatttg gggctctcca   1980
tgccccattt atttctttt ttattttatt actattatta ttattatttt tgagacagga    2040
tcttgctctg tgcccaggc tggagtgcag tggcacgatc tcagcttact gcaacctctg    2100
cctccccggt tcaagcaatt ctcctgcctc agcctcccga gtagctggga ctacaggcat   2160
ttgccaccat gcccaactga ttttgtattt ttagttgaga cagggtttca ccatgctggc   2220
caggctggtt tcgaacccct gacctcatga tctgcctgtc tcctcctcct gaagtgctgg   2280
gattacagac atgagccaca gagcccggcc caatttttt agggtttcgc cttatcggcc    2340
aggctggtct cgaactccag acctcaggtg atccaccac cctggctttc caaagtgcta    2400
ggattacaga cgtgagccat cgcgctggcc tattattatt attttttgaa atggagtctc   2460
tgtcacccag gctggagtgc agtggcatga tcttggctca cttcaacctc cgcttcctct   2520
ggtcaagcga ttctcctgcc tcggcctccc gaatagctgg gattacagat gcctgccacc   2580
atgcccggct aattttttgta tctttagtag agatggagtt tcatcatgtt ggtcagactg   2640
gtcttgaact cctgatctca ggcactccac ccgcctcggc ctcccaaagt gctgggatta   2700
caggtgtgaa ccaccgtgcc tggcacatac cccagtttag aactagtcat ccccagactt   2760
ctctctcagt cctctgggca tctgtggctc ctaaacacta gtttggccct tatgcctcaa   2820
tgatgccaca ttcacatctt tgcttgtact gtttccctag cccataatgg tcacccctca   2880
tcctctacaa gtcgggttct acatattctt acagacctgg ctcaaatgct gcccttctct   2940
atgaaatatt tatcccagtc ttagccggaa ccaaatgcag tttgggaact cagtactttg   3000
ctagggcctt gttttaccct ttgccttgac tcttgtgggg ttacatacaa ccttgtctcc   3060
ccactagact tccttaagat caagaatctt ttctgttcac ctctgtcaac cacaacactt   3120
gccaaggata acgatgcact gctgcttgca caaattttt tttttttttt ttgagacaga   3180
gtcttgctct gtcacccagg ctggagtgca gtggctcaat ctcagctcac tgcaatctct   3240
gcttcccagg ttcaagcaat tctcctgtct ccgcctctca gtagctggaa ttacaggca    3300 ctgctaccaa gcccggctaa tttttgtatt tttagtagaa atcaggtttc acgatgttgg   3360
ccaggctggt ctggaactcc tgacatcaag tgatccaccc acctcagcct cccaaagtgc   3420
tgggattaca cacatgagcc accgagcccg gccttcttgc acaaattgat gagggctaga   3480
taactggggt gcgggttggg gagggaggtg agaacaggaa ctgaggaaag aagaccagag   3540
ggcgggtgag tttactgcaa gctgatgtca atgcaacaag aattaggcat aaaaggagat   3600
taccgtgcat tgttgaagaa ggctgtgaaa agtgggaaag caggggctg aagctgaacc    3660 ctatcttttg tttccaatcc ctctccaaag attcgacacc tcttagaggc tgcaatccca   3720
gagagagttg aagagatccc tcctgaagtt cctacagagc ccaggagcc aggtcagcag    3780 agagaacctt cttctggtg agaggcatag gcaggcccaa gagctgtaga aatgaccatt    3840
```

```
tttgagctta agagccaggc cttgtgaggg gcgctttttt ttttttttcga ggcagagtct    3900
cactctgttg cccaggctac agtgcagtgg cacgatctcg gctcactgca agcaattgtc    3960
ccgcctcagc ctccctagta gctgggatta cagatgtgca ctaccatgcc cggcgaattt    4020
ttgtatttttt agtagagatg gggtttcacc atgttggcca ggctggtctc aaactcctga    4080
cctcaggtga tccacccgcc tcggcctccc aaagtgctag gattacaggt gtgagccacc    4140
gtgcctggtg aggggcattt tatgtgtata acctcatcag tacctcacaa gagtcctctg    4200
aggtcagatt tcttatcctt tttttttttt gagagatggg gtatcactct ctagcccagg    4260
ctggagtaca gtggtgcact ttaggctcac tgcaacctcc gcctcccgga ttcaagcaat    4320
tctccttcct agtagctggg attacaggca tgcaccacca cgcccagcta attttcgtat    4380
ttttagtaga gatgggtttt tgccatgttg gcaggctgg tctcaaactt ctgacctcag    4440
ttgatccacc cacctcagcc tcccaaagtg ctgggattac aggcgtgagc caccatactc    4500
ggcttttttt tttttttttt cttttttttcc caggctggag tgcagtggta tgatgatcat    4560
aggtcactgc agccttgacc tccagggctc aagcaatcct cccacctcag cctccagagt    4620
agctgggacc acaaggataa gccaccacac ctggctagtt tttaaatttt ttgtagagac    4680
agggtctcgc tatgttgccc aggctggcct caaactcctg ggctcaagcg atccaaagtg    4740
ttgggattac aggtgtgagc cacttcgccc agcctcccca ctttaccgat gaggaaagtg    4800
aggctcacag tggttaagca gtgtacccag ggtcaggatg ccagagatta gcctgggtct    4860
gattagaatc caggttacct tgacttcaga gtccatgctt ttccttaact gcatggctgt    4920
gggaatttgg aaagaagcag agaggctagt gactctcttg tccctccaga gaggattccg    4980
gtcactgtgc tgccacctga ggccatcacg atcctggagg cagagcccat acggatgctg    5040
gagattgagg tgagttcccc tgcacacagg gcctgaggtc cagccccctt gcatgtactt    5100
ctctctgtcc ccagagtcct gccttttctg tctccatttc cctattctct gtccctggca    5160
cttgagcacc cagtggcttc cttgaacctg gccctgtggc atgcctctgg gatccactct    5220
cctggatcca cttgccttttt tcagaaatat tattgaatcc cctccccttg ctcttcctct    5280
ctggacaggt gaacgggag ctcccagagg tcagccgccg agaactggac ctgctgatcg    5340
cagaggaaga agaagctatc ttgttagaaa gtaggtgtct ccggcagcgt agggcccgcc    5400
tggagctgga tagtcagacc cctggcgtgg gcattctggg actgggcaat gctcccattt    5460
ctcttttttct gtcctctgaa ctctgattct ctctccacag tcccgcggct cccacctcca    5520
gctcctgcag agtaagggca agaactccta gaccaggtag ggtgtcagtg ctgggaaggg    5580
tctcctcatt tctcttgccc atttcccctc agggtggaag gaataggaga ggcactgggt    5640
cctgaggagc tgaggctgac aggctgggaa cctggggccc tactcatggg tgagtgccca    5700
ccatgcccca gggcttttc tgggagtacc tggatactgc tgcagacaag gctttatat    5760
cccaacttgc taaagggagg accctgcagt ttcttgccct ggcatctgca aggggtaagg    5820
ggcttatggg acagagcccc ttgggtgttg ttgcagaggt gaccccccg gaggagctgc    5880
gtctgccagc cccacccagc ccagaggtga gtagcctccc ttctaatcct cctcctcctc    5940
ctctttgccc tcccccacaa ggactgcctc cccaagccca gggccactgc tagcttacag    6000
gggtccttaa tgcagatgat aaaagatgcc cctttctacg ccccatcgta tctggcctac    6060
gcttcccaga tgggtaccct tatgcaaggt atgagctgct caagtgcatg gagacccgc    6120
acaagccctc tccaggttcc tctaggggcg ggtgtgtgggg cctgttagca gtccaccaga    6180
atgacaggaa aaggagtaat gggcagcctt gcccctacct gccctcccca ctcaacagag    6240
```

```
gaggccccca gtccccccac ctcctcgccg ccgccgtcgt cgccggttac tgttctggga    6300
caaggagact cagatctccc cggagaaatt ccaggaacaa ctgcaaacca gagcccactg    6360
ctgggaatgt gtgagtgcag cccaggcttt gccggggaag ggagggaggc agggatgacc    6420
aggggcacat gcaggctgag ccttccaaac tcctcaggtg ggtgggggga ggattgggaa    6480
cttgatgaaa aatctcctcc attctccaga aaatgcaggc gatgtgggtt tgcacatata    6540
caactcttca tgctccttta gtgacccacc tgtcataccc atgggcacca ggttaaaaag    6600
tccttctttt agcaatgagc agggcaggca gggtcatgag cgcaaaagct ggggaagtcc    6660
agaagcccca gaacagtgca ttgcaaagag gcaaggggc cctgaggagt ggctgcttta    6720
taatggggct tctgaccttc ccccactaca cagcctatgg tgcagccgcc cgagaggacc    6780
atcagaggcc ctgcggagtt gttcagaacc ccaactctct gtaagaatgg tgggggttgg    6840
gcacgaagta tcctcaaaac caattcctca ttcctggtgc tcctcacgcc tcaaaccccg    6900
tgcctactac cctcttgtcc acagctggct ggctaccccc tgaactactg ggtctctgga    6960
cccattgtgc ccagccaccc ccaaaagccc tcaggcgaga gctgcctgag gaggcagccg    7020
ctgaggagga aaggagaaag attgaagttc caagtgagat tgaggtaact gcaccacctg    7080
tttactgcat cgccccagtg ccagggtctg cctgaccagc tggctgccct ctcctgctat    7140
gagagccaac agcacaggct cactggcctt gtgccttctg aggcccaagt cccagatgct    7200
tggggtctta gttctacttc tcccatcccc aggtcccgag ggaggccctg gagcccagtg    7260
ttccccttat ggtgtcttta ggtaagcacc tagagaagag gcgcagtggg accacaccct    7320
aaccactgtc ccaggaaact agtatcccaa ctgctgaagc tgttttatga gtgaaggcgt    7380
gtgtgtgtga cataaggaag cacggactgg tcctcctcag ctctcccacc tatgtgcttt    7440
taacaagtca ccgcacggct ctgccatcta cttacaccag gtggccacaa ggccctaact    7500
gccacccaag cagacaccca ctagcgcctt tcctccccca acagagatct ccctagaggc    7560
agctgaagag gagaagtccc gcatcagcct catcccacca gaagaacggt ggtaagcggc    7620
caggctccgt gggagccagg gcccacagcc cttggccagg tggtggaaac agctgctggg    7680
atgggtatgc cccttgtcac tgtcacagct gccaccttcc ctactctctc atgtcctcct    7740
agggcctggc ctgaggtgga ggcgccagaa gctcctgcat tgcccgtggt gcctgaactc    7800
cctgaggtgc ccatggagat gcctttggtg ctgcccccag agctcgagct gctctcactg    7860
gaagcagtgc acaggtacca gggaggtggc accttgatgg ggtggacccg ggctgaagcc    7920
tctgctaatg gttcttgatc cctataggc agtggcactg gagctgcagg ctaacaggga    7980
gcccgacttc agcagcctgg tgtcacctct cagcccccgc aggatggctg cccgggtctt    8040
ctacctgctc ctgggtgagt gtatgcatgt gtgtgtgtgt atgtggggca gggacacaga    8100
gaccagaggc ccgtacaggg actcccccga cctgccctct cctcgcctct tgaccagtgc    8160
tctcagcgca acagattctt cacgtgaaac aagaaaagcc atatggtcgc ctcctgatcc    8220
agccggggcc cagattccac tgaggttaga gtccatttac aaagctgcca ggaaaccggc    8280
cacttctagt aaaccacgtc gtgcctcact gggtcctgct tacctcatttt ctgaatgtgc    8340 atttccagcc ttcttgctct cagagctatt gttcaagcag aaaacaagct gcttttatta    8400
cagta                                                               8405
```

<210> SEQ ID NO 4
<211> LENGTH: 547
<212> TYPE: PRT

<213> ORGANISM: Homo sapiens

<400> SEQUENCE: 4

```
Met Phe Tyr Tyr Pro Asn Val Leu Gln Arg His Thr Gly Cys Phe Ala
1               5                   10                  15

Thr Ile Trp Leu Ala Ala Thr Arg Gly Ser Arg Leu Val Lys Arg Glu
            20                  25                  30

Tyr Leu Arg Val Asn Val Val Lys Thr Cys Glu Glu Ile Leu Asn Tyr
        35                  40                  45

Val Leu Val Arg Val Gln Pro Pro Gln Pro Gly Leu Pro Arg Pro Arg
    50                  55                  60

Phe Ser Leu Tyr Leu Ser Ala Gln Leu Gln Ile Gly Val Ile Arg Val
65                  70                  75                  80

Tyr Ser Gln Gln Cys Gln Tyr Leu Val Glu Asp Ile Gln His Ile Leu
                85                  90                  95

Glu Arg Leu His Arg Ala Gln Leu Gln Ile Arg Ile Asp Met Glu Thr
            100                 105                 110

Glu Leu Pro Ser Leu Leu Pro Asn His Leu Ala Met Met Glu Thr
        115                 120                 125

Leu Glu Asp Ala Pro Asp Pro Phe Phe Gly Met Met Ser Val Asp Pro
    130                 135                 140

Arg Leu Pro Ser Pro Phe Asp Ile Pro Gln Ile Arg His Leu Leu Glu
145                 150                 155                 160

Ala Ala Ile Pro Glu Arg Val Glu Glu Ile Pro Pro Glu Val Pro Thr
                165                 170                 175

Glu Pro Arg Glu Pro Glu Arg Ile Pro Val Thr Val Leu Pro Pro Glu
            180                 185                 190

Ala Ile Thr Ile Leu Glu Ala Glu Pro Ile Arg Met Leu Glu Ile Glu
        195                 200                 205

Gly Glu Arg Glu Leu Pro Glu Val Ser Arg Arg Glu Leu Asp Leu Leu
    210                 215                 220

Ile Ala Glu Glu Glu Glu Ala Ile Leu Leu Glu Ile Pro Arg Leu Pro
225                 230                 235                 240

Pro Pro Ala Pro Ala Glu Val Glu Gly Ile Gly Glu Ala Leu Gly Pro
                245                 250                 255

Glu Glu Leu Arg Leu Thr Gly Trp Glu Pro Gly Ala Leu Leu Met Glu
            260                 265                 270

Val Thr Pro Pro Glu Glu Leu Arg Leu Pro Ala Pro Pro Ser Pro Glu
        275                 280                 285

Arg Arg Pro Pro Val Pro Pro Pro Arg Arg Arg Arg Arg Arg
    290                 295                 300

Leu Leu Phe Trp Asp Lys Glu Thr Gln Ile Ser Pro Glu Lys Phe Gln
305                 310                 315                 320

Glu Gln Leu Gln Thr Arg Ala His Cys Trp Glu Cys Pro Met Val Gln
                325                 330                 335

Pro Pro Glu Arg Thr Ile Arg Gly Pro Ala Glu Leu Phe Arg Thr Pro
            340                 345                 350

Thr Leu Ser Gly Trp Leu Pro Pro Glu Leu Leu Gly Leu Trp Thr His
        355                 360                 365

Cys Ala Gln Pro Pro Lys Ala Leu Arg Arg Glu Leu Pro Glu Glu
    370                 375                 380

Ala Ala Ala Glu Glu Glu Arg Arg Lys Ile Glu Val Pro Ser Glu Ile
385                 390                 395                 400
```

```
Glu Val Pro Arg Glu Ala Leu Glu Pro Ser Val Pro Leu Met Val Ser
            405                 410                 415
Leu Glu Ile Ser Leu Glu Ala Ala Glu Glu Lys Ser Arg Ile Ser
        420                 425                 430
Leu Ile Pro Pro Glu Glu Arg Trp Ala Trp Pro Glu Val Glu Ala Pro
            435                 440                 445
Glu Ala Pro Ala Leu Pro Val Val Pro Glu Leu Pro Glu Val Pro Met
        450                 455                 460
Glu Met Pro Leu Val Leu Pro Pro Glu Leu Glu Leu Ser Leu Glu
465                 470                 475                 480
Ala Val His Arg Ala Val Ala Leu Glu Leu Gln Ala Asn Arg Glu Pro
            485                 490                 495
Asp Phe Ser Ser Leu Val Ser Pro Leu Ser Pro Arg Arg Met Ala Ala
            500                 505                 510
Arg Val Phe Tyr Leu Leu Leu Val Leu Ser Ala Gln Gln Ile Leu His
            515                 520                 525
Val Lys Gln Glu Lys Pro Tyr Gly Arg Leu Leu Ile Gln Pro Gly Pro
        530                 535                 540
Arg Phe His
545

<210> SEQ ID NO 5
<211> LENGTH: 232
<212> TYPE: DNA
<213> ORGANISM: Homo sapiens

<400> SEQUENCE: 5
gcaaaatcct tatgattggt tgctggctg cctcgggaga ccctgttgcc aggatacttg    60
gcgttcccga cccgacccc gttccccatt ggctgtcagg gcaaaagccg ccatctaatg   120
aggagcgagg tgcggtgccc cgaagcgctc gcttcccgcg gtgcgatcta gtcctgcagt   180
aggcggcccg gggccacacc gcggccgccc aagccagtgc aaggcccagg gg          232

<210> SEQ ID NO 6
<211> LENGTH: 232
<212> TYPE: DNA
<213> ORGANISM: Artificial Sequence
<220> FEATURE:
<223> OTHER INFORMATION: Synthetic construct

<400> SEQUENCE: 6
gtaaaatttt tatgattggt tgttggttg ttcgggaga ttttgttgtt aggatatttg     60
gcgttttcga ttcgattttc gtttttatt ggttgttagg gtaaaagtcg ttatttaatg   120
aggagcgagg tgcggtgttt cgaagcgttc gttttttcgtg gtgcgattta gttttgtagt  180
aggcggttcg gggttatatc gcggtcgttt aagttagtgt aaggtttagg gg          232

<210> SEQ ID NO 7
<211> LENGTH: 163
<212> TYPE: DNA
<213> ORGANISM: Homo sapiens

<400> SEQUENCE: 7
gaggaaatcc tcaattacgt gctggtacga gtgcaacccc cgcagcccgg cctgccgcgg    60
ccccgcttct ccctctatct ctcagcccaa cttcagatcg gtgtgatccg cgtctattct   120
caacaatgcc agtacctcgt gggtaaggct gggaaccctc aaa                    163
```

<210> SEQ ID NO 8
<211> LENGTH: 163
<212> TYPE: DNA
<213> ORGANISM: Artificial Sequence
<220> FEATURE:
<223> OTHER INFORMATION: Synthetic construct

<400> SEQUENCE: 8
gaggaaattt ttaattacgt gttggtacga gtgtaatttt cgtagttcgg tttgtcgcgg    60
tttcgttttt tttttattt tttagtttaa ttttagatcg gtgtgattcg cgtttatttt   120
taataatgtt agtatttcgt gggtaaggtt gggaattttt aaa                    163

<210> SEQ ID NO 9
<211> LENGTH: 26
<212> TYPE: DNA
<213> ORGANISM: Artificial Sequence
<220> FEATURE:
<223> OTHER INFORMATION: Synthetic construct

<400> SEQUENCE: 9
gtaaaatttt tatgattggt ttgttg                                        26

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
cccctaaacc ttacactaac t                                             21

<210> SEQ ID NO 11
<211> LENGTH: 26
<212> TYPE: DNA
<213> ORGANISM: Artificial Sequence
<220> FEATURE:
<223> OTHER INFORMATION: Synthetic construct

<400> SEQUENCE: 11
gaggaaattt ttaattaygt gttggt                                        26

<210> SEQ ID NO 12
<211> LENGTH: 23
<212> TYPE: DNA
<213> ORGANISM: Artificial Sequence
<220> FEATURE:
<223> OTHER INFORMATION: Synthetic construct

<400> SEQUENCE: 12
tttaaaaatt cccaacctta ccc                                           23

<210> SEQ ID NO 13
<211> LENGTH: 26
<212> TYPE: DNA
<213> ORGANISM: Artificial Sequence
<220> FEATURE:
<223> OTHER INFORMATION: Synthetic construct

<400> SEQUENCE: 13
tgtgattcgc gtttattttt aataat                                        26

<210> SEQ ID NO 14
<211> LENGTH: 34
<212> TYPE: DNA

```
<213> ORGANISM: Artificial Sequence
<220> FEATURE:
<223> OTHER INFORMATION: Synthetic construct

<400> SEQUENCE: 14
tgtgatttgt gtttattttt aataatgtta gtat                                    34
```